United States Patent [19]

Ulmer

[11] Patent Number: 5,674,743
[45] Date of Patent: Oct. 7, 1997

[54] METHODS AND APPARATUS FOR DNA SEQUENCING

[75] Inventor: Kevin M. Ulmer, Cohasset, Mass.

[73] Assignee: SEQ, Ltd., Princeton, N.J.

[21] Appl. No.: 463,831

[22] Filed: Jun. 5, 1995

Related U.S. Application Data

[62] Division of Ser. No. 376,761, Jan. 23, 1995, which is a continuation of Ser. No. 12,862, Feb. 1, 1993, abandoned.

[51] Int. Cl.$^6$ ............................................. C12M 3/00
[52] U.S. Cl. .......................... 435/287.2; 435/288.7; 422/82.08; 436/94; 436/172
[58] Field of Search ..................... 435/287.2, 288.7; 422/82.08; 436/94, 172

[56] References Cited

U.S. PATENT DOCUMENTS

| | | | |
|---|---|---|---|
| 3,872,312 | 3/1975 | Hirschfield | 250/458 |
| 4,166,105 | 8/1979 | Hirschfield | 424/8 |
| 4,676,274 | 6/1987 | Brown | 137/806 |
| 4,683,195 | 7/1987 | Mullis et al. | 435/6 |
| 4,683,202 | 7/1987 | Mullis | 435/9 |
| 4,793,705 | 12/1988 | Shera | 356/318 |
| 4,795,699 | 1/1989 | Tabor et al. | 435/5 |
| 4,863,849 | 9/1989 | Melamede | 435/6 |
| 4,889,818 | 12/1989 | Gelfand et al. | 435/194 |
| 4,893,886 | 1/1990 | Ashkin et al. | 350/1.1 |
| 4,962,037 | 10/1990 | Jett et al. | 435/6 |
| 4,983,038 | 1/1991 | Ohki et al. | 356/246 |
| 5,079,169 | 1/1992 | Chu et al. | 436/172 |
| 5,171,534 | 12/1992 | Smith et al. | 422/82.05 |
| 5,288,644 | 2/1994 | Beavis et al. | 436/94 |
| 5,322,796 | 6/1994 | Ishikawa | 436/94 |
| 5,374,527 | 12/1994 | Grossman | 435/6 |
| 5,405,747 | 4/1995 | Jett et al. | 435/6 |
| 5,547,839 | 8/1996 | Dower et al. | 435/6 |

OTHER PUBLICATIONS

Maxam and Gilbert, 1977, "A new method for sequencing DNA," Proc. Natl. Acad. Sci. USA 74:560–564.
Church and Gilbert, 1984, "Genomic sequencing," Proc. Natl. Acad. Sci. USA 81:1991–1995.
Saluz and Jost, 1987, "A Laboratory Guide To Genomic Sequencing. The direct sequencing of native uncloned DNA," *Biomethods*, vol. 1, Birkhäuser, Boston.
Frommer et al., 1992, "A genomic sequencing protocol that yields a positive display of 5-methylcytosine residues in individual DNA strands," Proc. Natl. Acad. Sci. USA 89:1827–1831.

(List continued on next page.)

*Primary Examiner*—David A. Redding
*Attorney, Agent, or Firm*—Pennie & Edmonds

[57] ABSTRACT

The present invention provides a method and apparatus for automated DNA sequencing. The method of the invention includes the steps of: a) using a processive exonuclease to cleave from a single DNA strand the next available single nucleotide on the strand; b) transporting the single nucleotide away from the DNA strand; c) incorporating the single nucleotide in a fluorescence-enhancing matrix; d) irradiating the single nucleotide to cause it to fluoresce; e) detecting the fluorescence; f) identifying the single nucleotide by its fluorescence; and g) repeating steps a) to f) indefinitely (e.g., until the DNA strand is fully cleaved or until a desired length of the DNA is sequenced). The apparatus of the invention includes a cleaving station for the extraction of DNA from cells and the separation of single nucleotides from the DNA; a transport system to separate the single nucleotide from the DNA and incorporate the single nucleotide in a fluorescence-enhancing matrix; and a detection station for the irradiation, detection and identification of the single nucleotides. The nucleotides are advantageously detected by irradiating the nucleotides with a laser to stimulate their natural fluorescence, detecting the fluorescence spectrum and matching the detected spectrum with that previously recorded for the four nucleotides in order to identify the specific nucleotide.

27 Claims, 13 Drawing Sheets

OTHER PUBLICATIONS

Sanger and Coulson, 1975, "A rapid method for determining sequences in DNA by primed synthesis with DNA polymerase," J. Mol. Biol. 94:441–448.

Sanger et al., 1977, "DNA sequencing with chain–terminating inhibitors," Proc. Natl. Acad. Sci. USA 74:5463–5467.

Elder et al., 1986, "Automatic reading of DNA sequencing gel autoradiographs using a large format digital scanner," Nucl. Acids Res. 14:417–424.

Smith et al., 1986, "Fluorescence detection in automated DNA sequence analysis," Nature 321:674–679.

Smith et al., 1985, "The synthesis of oligonucleotides containing an aliphatic amino group at the 5' terminus: synthesis of fluorescent DNA primers for use in DNA sequence analysis," Nucl. Acids Res. 13:2399–2412.

Prober et al., 1987, "A system for rapid DNA sequencing with fluorescent chain–terminating dideoxynucleotides," Science 238:336–341.

Endo et al., 1991, "Human genome analysis system," Nature 352:89–90.

Wada, 1987, "Automated high–speed DNA sequencing," Nature 325:771–772.

Kostichka et al., 1992, "High speed automated DNA sequencing in ultrathin slab gels," Bio/Technology 10:78–81.

Drossman et al., 1990, "High–Speed separations of DNA sequencing reactions by capillary electrophoresis," Anal. Chem. 62:900–903.

Chen et al., 1991, "Single–color laser–induced fluorescence detection and capillary gel electrophoresis for DNA sequencing," SPIE: Optical Methods for Ultrasensitive Detection and Analysis: Techniques and Applications 1435:161–167.

Gebhart, 1992, "Genomyx seeks to find niche in science and business of gene sequencing," Genet. Eng. News 12:15.

Church and Kieffer–Higgins, 1988, "Multiplex DNA sequencing," Science 240:185–188.

Gillevet, 1990, "Chemiluminescent multiplex DNA sequencing," Nature 348:657–658.

Yang and Youvan, 1989, "A prospectus for multispectral–multiplex DNA sequencing," Bio/Technology 7:576–580.

McCormick and Amendola, 1978, "Cytospectrometers for subcellular particles and macromolecules: design considerations," in *Theory, Design and Biomedical Applications of Solid State Chemical Sensors*, Cheung et al. (eds.), CRC Press, West Palm Beach, pp. 219–250.

Strezoska et al., 1991, "DNA sequencing by hybridization: 100 bases read by a non–gel–based method," Proc. Natl. Acad. Sci. USA 88:10089–10093.

Bains, 1992, "Setting a sequence to sequence a sequence," Bio/Technology 10:757–58.

Beer and Moudrianakis, 1962, "Determination of base sequence in nucleic acids with the electron microscope: visibility of a marker," Proc. Acad. Sci. USA 48:409–416.

Binning et al., 1982, "Surface studies by scanning tunneling microscopy," Phys. Rev. Lett. 49:57–61.

Binnig and Röhrer, 1984, "Scanning tunnelling microscopy," in *Trends in Physics*, J. Janta and J. Pantoflicek (eds.), European Physical Society, The Hague, pp. 38–46.

Driscoll et al., 1990, "Automic–scale imaging of DNA using scanning tunnelling microscopy," Nature 346:294–296.

Dunlap and Bustamante, 1989, "Images of single–stranded nucleic acids by scanning tunnelling microscopy," Nature 342:204–206.

Clemmer and Beebe, 1991, "Graphite: a mimic for DNA and other biomolecules in scanning tunneling microscope studies," Science 251:640–642.

Hansma et al., 1991, "Progress in sequencing deoxyribonucleic acid with an atomic force microscope," J. Vac. Sci. Technol. B 9:1282–1284.

Cantor et al., 1964, "Exoenzyme kinetics with applications to the determination of nucleotide sequences," Biopolymers 2:51–63.

Chen and Sigman, 1987, "Chemical conversion of a DNA–binding protein into a site–specific nuclease," Science 237:1197–1201.

Le Doan et al., 1987, "Sequence–specific recognition, photocrosslinking and cleavage of the DNA double helix by an oligo–[$\alpha$]–thymidylate covalently linked to an azidoproflavine derivative," Nucleic Acids Res. 15:7749–7760.

Praseuth et al., 1988, "Sequence–specific binding and photocrosslinking of $\alpha$ and $\beta$ oligodeoxynucleotides to the major groove of DNA via triple–helix formation," Proc. Natl. Acad. Sci. USA 85:1349–53.

Jett et al., 1989, "High–speed DNA sequencing: an approach based upon fluorescence detection of single molecules," J. Biomolecular Structure & Dynamics 7(2):301–309.

Jett et al, 1989, "An approach for DNA sequencing at 1000 bases per second," in *Book of Abstacts, Sixth Conversation in Biomolecular Stereodynamics*, SUNY at Albany, Jun. 06–10, 1989, p. 157.

Davis et al., 1991, "Rapid DNA sequencing based upon single molecule detection," GATA 8(1):1–7.

Shera et al., 1990, "Detection of single fluorescent molecules," Chemical Phys. Lett. 174(6):553–557.

Soper et al., 1991, "Single–molecule detection of rhodamine 6G in ethanolic solutions using continuous wave laser excitation," Anal. Chem. 63:432–437.

Martin and Davies, 1986, "Automated DNA sequencing: progress and prospects," Bio/Technology 4:890–895.

Bains, 1990, "Alternative routes through the genome," Bio/Technology 8:1251.

Hunkapiller et al., 1991, "Large–scale and automated DNA sequence determination," Science 254:59–67.

Zimmern and Kaesberg, 1978, "3'–terminal nucleotide sequence of encephalomyocarditis virus RNA determined by reverse transcriptase and chain–terminating inhibitors," Proc. Natl. Acad. Sci. USA 75:4257–4261.

Mills and Kramer, 1979, "Structure–independent nucleotide sequence analysis," Proc. Natl. Acad. Sci. USA 76:2232–2235.

Peattie, 1979, "Direct chemical method for sequencing RNA," Proc. Natl. Acad. Sci. USA 76:1760–1764.

Donis–Keller et al., 1977, "Mapping adenines, guanines, and pyrimidines in RNA," Nucl. Acids Res. 4:2527–2538.

Simoncsits et al., 1977, "New rapid gel sequencing method for RNA," Nature 269:833–836.

Axelrod et al., 1978, "Specific termination of RNA polymerase synthesis as a method of RNA and DNA sequencing," Nucl. Acids Res. 5:3549–3563.

Kramer and Mills, 1978, "RNA sequencing with radioactive chain–terminating ribonucleotides," Proc. Natl. Acad. Sci. USA 75:5334–5338.

Greenlees et al., "High resolution laser spectroscopy with minute samples," Opt. Commun. 23:236–239.

Pan et al., 1980, "Detection of individual atoms in helium buffer gas and observation of their real–time motion," Opt. Lett. 5:459–461.

Nagourney et al., 1986, "Shelved optical electron amplifier: observation of quantum jumps," Phys. Rev. Lett. 56:2797–2799.

Bergquist et al., 1986, "Observation of quantum jumps in a single atom," Phys. Rev. Lett. 57:1699–1702.

Robinson, 1986, "Quantum jumps seen in a single ion," Science 234:24–25.

Hirschfeld, 1977, "Real time measurement and observation of viruses in biological fluids," SPIE: Multidisciplinary Microscopy 104:16–20.

Hirschfeld, 1976, "Optical microscopic observation of single small molecules," Applied Optics 15:2965–2966.

Dovichi et al., 1983, "Attogram detection limit for aqueous dye samples by laser–induced fluorescence," Science 219:845–847.

Dovichi et al., 1983, "An approach to single molecule detection by laser–induced fluorescence," SPIE: Laser–Based Ultrasensitive Spectroscopy and Detection V 426:71–73.

Trkula et al., 1984, "Prospects for single-molecule detection in liquids by laser–induced fluorescence," in *Analytical Chemistry Symposium Series*, vol. 19, pp. 53–55.

Dovichi et al., 1984, "Laser–induced fluorescence of flowing samples as an approach to single-molecule detection in liquids," Anal. Chem. 56:348–354.

Zarrin and Dovichi, 1985, "Sub-picoliter detection with the sheath flow cuvette," Anal. Chem. 57:2690–2692.

Nguyen et al., 1987, "Ultrasensitive laser–induced fluorescence detection in hydrodynamically focused flows," J. Opt. Soc. Am. B 4:138–143.

Mathies and Stryer, 1986, "Single-molecule fluorescence detection: a feasibility study using phycoerythrin," in *Applications of Fluorescence in the Biomedical Sciences*, Alan R. Liss, Inc., pp. 129–140.

Nguyen et al., 1987, "Detection of single molecules of phycoerythrin in hydrodynamically focused flows by laser–induced fluorescence," Anal. Chem. 59:2158–2161.

Peck et al., 1989, "Single-molecule fluorescence detection: autocorrelation criterion and experimental realization with phycoerythrin," Proc. Natl. Acad. Sci. USA 86:4087–4091.

Rigler and Widengren, 1990, "Ultrasensitive detection of single molecules by fluorescence correlation spectroscopy," in *BioScience*, B. Klinge & C. Owmar (eds.), pp. 180–183.

Orrit and Bernard, 1990, "Single pentacene molecules detected by fluorescence excitation in a p–terphenyl crystal," Phys. Rev. Lett. 65:2716–2719.

Ambrose and Moerner, 1991, "Fluorescence spectroscopy and spectral diffusion of single impurity molecules in a crystal," Nature 349:225–227.

Ambrose et al., 1991, "Detection and spectroscopy of single pentacene molecules in a p–terphenyl crystal by means of fluorescence excitation," J. Chem. Phys. 95:7150–7163.

Moerner and Ambrose, 1991, "Finding a single molecule in a haystack: laser spectroscopy of solids from √N to N = 1," SPIE: Optical Methods For Ultrasensitive Detection Analysis: Techniques and Applications 1435:244–250.

Soper et al., 1991, "Rapid sequencing of DNA based on single molecule detection," SPIE: Optical Methods for Ultrasensitive Detection and Analysis: Techniques and Applications 1435:168–178.

Borresen, 1967, "The fluorescence of guanine and guanosine. Effects of temperature and viscosity on fluorescence polarization and quenching," Acta Chemica Scand. 21:920–936.

Eastman and Rosa, 1968, "The fluorescence of adenine. The effects of solvent and temperature on the quantum yield," Photochem. & Photobiol. 7:189–201.

Guéron et al., 1974, "Excited states of nucleic acids," in *Basic Principles in Nucleic Acid Chemistry*, Paul O.P. Ts'O (ed.) pp. 311–398.

Maniatis et al., 1982, "Large–scale isolation of plasmid DNA," in Molecular Cloning, A Laboratory Manual, Cold Spring Harbor Laboratory, Cold Spring Harbor, New York, pp. 86–96, and 280–81.

Gyllenstein and erlich, 1988, "Generation of single–stranded DNA by the polymerase chain reaction and its application to direct sequencing of the HLA–DQA locus," Proc. Natl. Acad. Sci. USA 85:7652–7656.

Ochman et al., 1988, "Genetic applications of an inverse polymerase chain reaction," Genetics 120:621–623.

Loh et al., 1989, "Polymerase chain reaction with single-sided specificity: analysis of T cell receptor ∂ chain," Science 243:217–220.

Buican et al., 1989, "Optical trapping, cell manipulation, and robotics," SPIE: New Technologies In Cytometry 1063:190–197.

Ashkin and Dziedzic, 1987, "Optical trapping and manipulation of viruses and bacteria," Science 235:1517–1520.

Schut et al., 1991, "Experimental and theoretical investigations on the validity of the geometrical optics model for calculating the stability of optical traps," Cytometry 12:479–485.

Preston, 1987, "High–resolution leukocyte analyzers: retrospective and prospective," Applied Optics 26:3258–3265.

Buican et al., 1987, "Automated single–cell manipulation and sorting by light trapping," Applied Optics 26:5311–5316.

Gasser and Laemmli, 1987, "Improved methods for the isolation of individual and clustered mitotic chromosomes," Exp. Cell Res. 173:85–98.

Tao et al., 1987, "Direct gene transfer into human cultured cells facilitated by laser micropuncture of the cell membrane" Proc. Natl. Acad. Sci. USA 84:4180–4184.

Steubing et al., 1991, "Laser induced cell fusion in combination with optical tweezers: the laser cell fusion trap," Cytometry 12:505–510.

Zimmerman, 1986, "Electrical breakdown, electropermeabilization and electrofusion," Rev. Physiol. Biochem. Pharmacol. 105:175–256.

Zeidler, 1988, "Automated chromosome analysis," Nature 334–635.

Monajembashi et al., 1986, "Microdissection of human chromosomes by a laser microbeam," Exp. Cell Res. 167:262–265.

Lüdecke et al., 1989, "Cloning defined regions of the human genome by microdissection of banded chromosomes and enzymatic amplification," Nature 338:348–350.

Seeger et al., 1991, "Application of laser optical tweezers in immunology and molecular genetics," Cytometry 12:497–504.

Paulson and Laemmli, 1977, "The structure of histone–depleted metaphase chromosomes," Cell 12:817–828.

Adolph et al., 1977, "Role of nonhistone proteins in metaphase chromosome structure," Cell 12:805–816.

Lewis and Laemmli, 1982, "Higher order metaphase chromosome structure: evidence for metalloprotein interactions," Cell 29:171–181.

Yanagida et al., 1986, "Video-connected fluorescence microscopy of large DNA molecules, chromatin, and chromosomes," in *Applications of Fluorescence in the Biomedical Sciences*, Taylor, D.L. et al. (eds.), Alan R. Liss, Inc., New York, pp. 321–345.

Laemmli, 1975, "Characterization of DNA condensates induced by poly(ethylene oxide) and polylysine," Proc. Natl. Acad. Sci. USA 72:4288–4292.

Hiraoka et al., 1987, "The use of a charge-coupled device for quantitative optical microscopy of biological structures," Science 238:36–41.

Richards, 1989, "DNA molecules observed," Nature 338:461–462.

Smith et al., 1989, "Observation of individual DNA molecules undergoing gel electrophoresis," Science 243:203–206.

Schwartz and Koval, 1989, "Conformational dynamics of individual DNA molecules during gel electrophoresis," Nature 338:520–522.

Morikawa and Yanagida, 1981, "Visualization of individual DNA molecules in solution by light microscopy: DAPI staining method," J. Biochem. 89:693–696.

Matsumoto et al., 1981, "Light microscopic structure of DNA in solution studied by the 4',6-diamidino-2-phenylindole staining method," J. Mol. Biol. 152:501–516.

Yanagida et al., 1983, "Dynamic behaviors of DNA molecules in solution studied by fluorescence microscopy," C.S.H. Symp. Quant. Biol. 47:177–187.

Hirschfield, 1976, "Optical microscopic observation of single small molecules," Applied Optics 15:2965–2966.

Greider and Blackburry, 1987, "The telomere terminal transferase of tetrahymena is a ribonucleoprotein enzyme with two kinds of primer specificity," Cell 51:887–898.

Kato et al., 1967, "Deoxynucleotide-polymerizing enzymes of calf thymus gland," J. Biol. Chem. 242:2780–2789.

Urdea et al., PCT Publication WO 90/13667, published Nov. 15, 1990.

Tomalia and Wilson, European Patent Publication EP 247629 A2, published Dec. 2, 1987.

Kishino and Yanagida, 1988, "Force measurements by micromanipulation of a single actin filament by glass needles," Nature 334:74–76.

Holzwarth et al., 1987, "Transient orientation of linear DNA molecules during pulsed-field gel electrophoresis," Nucl. Acids Res. 15:10031–10044.

Smith et al., 1989, "Observation of individual DNA molecules undergoing gel electrophoresis," Science 243:203–206.

Schwartz and Koval, 1989, "Conformational dynamics of individual DNA molecules during gel electrophoresis," Nature 338:520–522.

Bustamante, 1991, "Direct observation and manipulation of single DNA molecules using fluorescence microscopy," Annu. Rev. Biophys. Biophys. Chem. 20:415–446.

Hjertén, 1985, "High-performance electrophoresis elimination of electroendosmosis and solute absorption," J. Chromatog. 347:191–198.

Brody et al., 1986, "Processivity and kinetics of the reaction of exonuclease I from *Escherichia coli* with polydeoxyribonuclotides," J. Biol. Chem. 261:7136–7143.

Little, 1967, "An exonuclease induced by bacteriophage λ," J. Biol. Chem. 242:679–686.

Carter and Radding, 1971, "The role of exonuclease and β protein of phage λ in genetic recombination," J. Biol. Chem. 246:2502–2512.

Little, 1981, "Structural analysis of nucleic acids," in *Gene Amplification and Analysis*, vol. 2, Chirikjian and Papas (eds.), Elsevier/North-Holland, New York. pp. 135–145.

Joseph and Kolodner, 1983, "Exonuclease VIII of *Escherichia coli*. II. Mechanism of action," J. Biol. Chem. 258:10418–10424.

Thomas and Olivera, 1978, "Processivity of DNA exonucleases," J. Biol. Chem. 253(2):424–429.

Das and Fujimura, 1980, "Mechanism of 3'→5' exonuclease associated with phage T5-induced DNA polymerase: processiveness and template specificity," Nucl. Acids Res. 8:657–671.

Becerra and Wilson, 1984, "Properties of a novel oligonucleotide-releasing bidirectional DNA exonuclease from mouse myeloma," Biochem. 23:908–914.

Joannes et al., 1985, "DNA filter retention assay for exonuclease activities. Application to the analysis of processivity of phage T5 induced 5'-exonuclease," Biochem. 24:8043–8049.

Brody et al., 1986, "Processivity and kinetics of the reaction of exonuclease I from *Escherichia coli* with polydeoxyribonucleotides," J. Biol. Chem. 261:7136–7143.

McLaren et al., 1991, "mRNA degradation by processive 3'-5' exoribonucleases in vitro and the implications for prokaryotic mRNA decay in vivo," J. Mol. Biol. 221:81–95.

Klee and Singer, 1968, "The processive degradation of individual polyribonucleotide chains," J. Biol. Chem. 243:923–927.

Nossal and Singer, 1968, "The processive degradation of individual polyribonucleotide chains. I. *Escherichia coli* ribonuclease II," J. Biol. Chem. 243:913–922.

Little, 1984, "Microminiature refrigeration," Rev. Sci. Instrum. 55:661–680.

Zarrin et al., 1985, "Sub-picoliter detection with the sheath flow culvette," Anal. Chem. 57:2690–2692.

Shapiro, 1988, "How a flow cytometer works," in *Practical Flow Cytometry*, Alan R. Liss, Inc., Chap. 4, pp. 21–86.

Pinkel and Stovel, "Flow chambers and sample handling," *Flow Cytometry: Instrumentation and Data Analysis*, Van Dilla et al. (eds.), Academic Press, Chap. 3, pp. 77–128.

Steen, 1990, "Characteristics of Flow Cytometers," in *Flow Cytometry and Sorting*, 2nd Edition, Melamed, et al. (eds.), pp. 11–25.

Cheng et al., 1990, "Interaction of capillary zone electrophoresis with a sheath flow cuvette detector," Anal. Chem. 62:496–503.

Little, 1990, "Advances in Joule-Thomson cooling," in *Advances in Cryogenic Engineering*, vol. 35, R.W. Fast (ed.), Plenum Press, New York. pp. 1305–1314.

Kroener and Luyet, 1966, "The temperature of the glass transition in aqueous solutions of glycerol and ethylene clycol," Biodynamica 10:33–40.

Kroener and Luyet, 1966, "Discontinuous change in expansion coefficient at the glass transition temperature in aqueous solutions of glycerol," Biodynamica 10:41–45.

Luyet and Kroener, 1966, "Formation of cracks during the vitrification of glycerol solutions and disappearance of the cracks during rewarming," Biodynamica 10:47–52.

Luyet and Rasmussen, 1967, "Study of differential thermal analysis of the temperatures of instability of rapidly cooled solutions of polyvinyl-pyrrolidone," Biodynamica 10:137–147.

Luyet and Rasmussen, 1968, "Study by differential thermal analysis of the temperatures of instability of rapidly cooled solutions of glycerol, ethylene glycol, sucrose and glucose," Biodynamica 10:167–191.

Rasmussen and MacKenzie, 1968, "Phase diagram for the system water–dimethylsulphoxide," Nature 220:1315–1317.

Rasmussen and MacKenzie, 1971, "The glass transition in amorphous water. Application of the measurements to problems arising in cryobiology," J. Phys. Chem. 75:967–973.

MacFarlane et al., 1986, "Devitrification in aqueous solution glasses in high heating rates," Cryo–Letters 7:73–80.

Fox and Coulter, 1980, "Enhanced light collection in a flow cytometer," Cytometry 1:21–25.

Steinkamp et al., 1973, "A new multiparameter separator for microscopic particles and biological cells," Rev. Sci. Intrum. 44:1301–1310.

Stockman et al., 1990, "Modelling viscous segregation in immiscible fluids using lattice–gas automata," Nature 348:523–525.

Karagiannis et al., 1988, "Interface determination in bio-component extrusion," Polymer Engineering and Science 28:982–988.

Wu and Dovichi, 1989, "High–sensitivity fluorescence detector for fluorescein isothiocyanate derivatives of amino acids separated by capillary zone electrophoresis," J. Chromatog. 480:141–155.

Skogen–Hagenson et al., 1977, "A high efficiency flow cytometer," J. Histochem. Cytochem. 25:784–789.

Watson, 1989, "Flow cytometry chamber with $4\pi$ light collection suitable for epifluorescence microscopes," Cytometry 10:681–688.

Watson, 1985, "A method for improving light collection by 600% from square cross section flow cytometry chambers," Br. J. Cancer 51:433–435.

Leif and Wells, 1987, "Optical analysis of the AMAC IIIS transducer," Applied Optics 26:3244–3248.

Avnir et al., 1984, "The nature of the silica cage as reflected by spectral changes and enhanced photostability of trapped rhodamine 6G," J. Phys. Chem. 88:5956–5959.

Gromov et al., 1985, "Efficient plastic–host dye lasers," J. Opt. Soc. Am. B 2:1028–1031.

Rodchenkova et al., 1986, "Effect of polymer matrix on spectral and lasing characteristics of rhodamine 6G," Opt. Spectrosc. (USSR) 60:35–37.

Bondar et al., 1987, "Photostability of laser dyes in polyurethane under excitation by light of different intensities," Opt. Spectrosc. (USSR) 62:798–800.

Reisfeld, 1987, "Criteria and prospects of new lasers based on fluorescent dyes in glasses," Journal de Physique 48:C7–423–426.

Reisfeld et al., 1988, "Perylene dye in a composite sol–gel glass —a new solid-state tunable laser in the visible range," SPIE: French–Israeli Workshop on Solid State Lasers 1182:230–239.

Merrill et al., 1979, "Investigations in high–precision sorting," J. Histochem. Cytochem. 27:280–283.

Schildkraut et al., 1979, "A system for storage and retrieval of individual cells following flow cytometry," J. Histochem. Cytochem. 27:289–292.

Stovel and Sweet, 1979, "Individual cell sorting," J. Histochem. Cytochem. 27:284–288.

Guéron et al., 1974, "Excited States of Nucleic Acids," in *Basic Principles in Nucleic Acid Chemistry*, vol. 1, Academic Press, New York, pp. 311–398.

Howorth et al., 1989, "GaAs/ALAs super lattice photocathodes," SPIE: New Methods in Microscopy and Low Light Imaging 1161:189–196.

Tsuchiya et al., 1986, "Two–dimensional sweeps expanding capability and application of streak cameras," SPIE: High Speed Photography, Videography and Photonics IV 693:125–133.

Urakami et al., 1986, "Characterization of photon–counting streak camera," SPIE: High Speed Photography, Videography and Photonics IV 693:98–104.

Kume et al., 1988, "Ultrafast microchannel plate photomultipliers," Applied Optics 27:1170–1178.

Cheng et al., 1978, "Intensified CCD readout system for ultrafast streak cameras," J. Appl. Phys. 49:5421–5426.

O'Connor and Phillips, 1984, *"Time–Correlated Single Photon Counting"*, Academic Press, New York.

Rigler et al., 1984, "Picosecond Single Photon Fluorescence Spectroscopy of Nucleic Acids," *Springer Series in Chemical Physics*, vol. 38, pp. 472–476.

Laws et al., 1984, "Gating circuit for single photon–counting fluorescence lifetime instruments using high repetition pulsed light sources," Rev. Sci. Instrum. 55:1564–1568.

Williams, 1989, "Polarized One–and Two–Photon Fluorescence Excitation Spectroscopy on Selected Nucleic Acid Bases," Doctoral Thesis, Montana State University.

Nebel and Beigang, 1991, "External frequency conversion of cw mode–locked $Ti:AI_2O_3$ laser radiation," Optics Lett. 16:1729–1731.

Acugen™ System Report 88–106, EG&G Biomolecular, 1988.

Turmel et al., 1992, "Sequencing up to 800 bases manually using pulsed field," in *Genome Mapping & Sequencing*, Cold Spring Harbor Laboratory, Abstract #112.

Turmel et al., 1992, "Manual sequencing using pulsed field," Electrophoresis (in press), pp. 1–9.

Brennan et al., 1990, "New methods to sequence DNA by mass spectrometry," SPIE:New Technologies in Cytometry and Molecular Biology 1206:60–77.

Brennan et al., 1990, "New methods to sequence DNA by mass spectrometry," in *Biological Mass Spectrometry*, A.L. Burlingame and J.A. McCloskey (eds.) Elsevier, Amsterdam, pp. 159–177.

Hurst et al., 1979, "Resonance ionization spectroscopy and one–atom detection," Rev. Mod. Phys. 51: pp. 767–819.

Arlinghaus et al., 1991, "Applications of resonance ionization spectroscopy for semiconductor, environmental and biomedical analysis, and for DNA sequencing," SPIE:Optical Methods for Ultrasensitive Detection and Analysis: Technique and Application 1435: pp. 26–35.

Jacobson et al., 1991, "An approach to the use of stable isotopes for DNA sequencing," Genomics 9: pp. 51–59.

Parr et al., 1992, "Matrix–assisted laser desorption/ionization mass spectrometry of synthetic oligodeoxyribonucleotides," Rapid. Commu. Mass. Spec. 6: pp. 369–372.

Gray et al., 1991, "Investigation of the utility of x–ray diffraction in DNA sequences analysis," DOE Human Genome Program Report of the Second Contractor–Grantee Workshop, Feb. 17–20 Santa Fe, New Mexico, p. 56 and p. 80.

Luo and Tian, 1988, "Low temperature synthesis of monolithic silica glass from the system $Si(OC_2H_5)_4$–$H_2O$–HCl–$HOCH_2CH_2OH$ by the sol–gel method," J. Non–Crystalline Solids 100:254–262.

Morgan and Callis, 1979, "Photochemistry and photophysics of guanine–containing dinucleosides," Photochemistry and Photobiology 29: pp. 1107–1113.

Bernet et al., 1991, "Streak cameras applied to spatial chronometry," SPIE: Ultrahigh–and High Speed Photography, Videography and Photonics 1539: pp. 89–99.

Malmstadt et al., 1972, "Photon counting for spectrophotometry," Anal. Chem. 44: pp. 63A.

Birch et al., 1988, "Multiplexed time–correlated single photon counting," SPIE: Time–Resolved Laser Spectroscopy in Biochemistry 909: pp. 8–14.

Knutson, 1988, "Fluorescence detection: schemes to combine speed, sensitivity and spatial resolution," SPIE: Time Resolved Laser Spectroscopy in Biochemistry 909:51–60.

Beechem, 1990, "Time–resolved fluorescence studies of the protein folding process: new instrumentation, analysis, and experimental approaches," SPIE: Time Resolved Laser Spectroscopy in Biochemistry II 1204:686–698.

Mathies and Huang, 1992, "Capillary array electrophoresis: an approach to high–speed, high–throughput dNA sequencing," Nature 359:167–169.

Dyson, 1992, "The future of physics," in *From Eros to Gaia*, Pantheon Books, New York, pp. 151–159.

Neuhauser et al., 1980, "Localized visible Ba+ mono–ion oscillator," Phys. Rev. A, 22:1137–1140.

Jett, et al., 1988, "Advanced concepts for base sequencing in DNA," in The Human Genome Initiative of the U.S. Department of Energy, DOE/ER–0382, p. 33.

Jett et al., 1990, "Advanced concepts for base sequencing in DNA," in Human Genome 1989–90 Program Report, DOE/ER–0446P, p. 94.

Davis et al., 1991, "Rapid DNA sequencing based upon single molecule detection," in DOE Human Genome Program Report of the Second Contractor–Grantee Workshop, U.S. Dept. of Energy, S 21, p. 24.

Soper et al., 1991, "Single molecule detection of nucleotides tagged with fluorescent dyes," in DOE Human Genome Program Report of the Second Contractor–Grantee Workshop, U. S. Dept. of Energy, p. 87, p. 103.

Parker, 1991, "Los Alamos, firm join in gene mapping," Albuquerque Journal, Friday, Mar. 22, 1991.

Jett et al., 1992, "Rapid DNA sequencing based on fluorescence detection of single molecules," in Human Genome 1991–92 Program Report, DOE/ER–0544P, pp. 129–130.

Harding and Keller, 1992, "Single–molecule detection as an approach to rapid DNA sequencing," Trends in Biotechnology, 10:55–57.

Ward et al., 1969, "Fluorescence studies of nucleotides and polynucleotides. I. Formycin, 2–amino purine riboside, 2,6–diaminopurine riboside, and their derivatives," J. of Biol. Chem., 244:1228–1237.

Ward and Reich, 1969, "Biochemical studies of the nucleoside analogue, formycin," J. Biol. Chem. 244:3243–3250.

Ward et al., 1972, "Fluorescence studies of nucleotides and polynucleotides. III. Diphosphopyridine nucleotide analogues which contain fluorescent purines," J. Biol. Chem. 247:705–719.

Ward et al. 1972, "Fluorescence studies of nucleotides and polynucleotides," J. Biol. Chem. 247:4014–4020.

Glazer and Rye, 1992, "Stable dye–DNA intercalation complexes as reagents for high–sensitivity fluorescence detection," Nature 359:859–861.

Smith et al., 1992, "Direct mechanical measurements of the elasticity of single DNA molecules by using magnetic beads," Science 258:1122–1126.

Committee on Mapping and Sequencing the Human Genome Board on Basic Biology Commission on Life Sciences National Research Coucil, 1988 Mapping and Sequencing the Human Genome, National Acadamy Press, pp. 56–74.

Leonard and Tolman, 1975, "Fluorescent nucleosides and nucleotides," in *Chemistry, Biology, and Clinical Uses of Nucleoside Analogs*, A. Bloch (ed.), Ann. of the New York Academy of Sciences, 255:43–58.

Brauner, 1991, "Two–phase liquid—liquid annular flow," Int. J. Multiphase Flow, 17:59–76.

Brauner and Maron, 1992, "Flow pattern transitions in two–phase liquid—liquid flow in horizontal tubes," Int. J. Multiphase Flow, 18:123–140.

Fisher and Johns, 1976, "Pyrimidine photohydrates," in *Photochemistry and Photobiology of Nucleic Acids*, S.Y. Wang (ed.), Academic Press, New York, vol. 1, pp. 169–224.

Weber et al., 1989, "Structural origins of high–affinity biotin binding to streptavidin," Science, 243:85–88.

Hendrickson et al., 1989, "Crystal structure of core streptavidin determined from multiwavelength anomalous diffraction of synchrotron radiation," Proc. Natl. Acad. Sci. USA 86:2190–2194.

Ahlers et al., 1989, "Specific recognition and formation of two–dimensional streptavidin domains in monolayers: applications to molecular devices," Thin Solid Films, 180:93–99.

Sano and Cantor, 1990, "Expression of a cloned streptavidin gene in *Escherichia coli* ", Proc. Natl. Acad. Sci. USA 87:142–146.

Sano and Cantor, 1991, "A streptavidin–protein A chimera that allows one–step production of a variety of specific antibody conjugates," Bio/Technology 9:1378–1381.

Hirschfeld, 1976, "Quantum efficiency independence of the time integrated emission from a fluorescent molecule," Applied Optics 15:3135–3139.

Yakushi et al., 1982, "Cryostat for microspectroreflectometry by use of a microminiature refrigerator," Rev. Sci. Instrum. 53:1292–1293.

Misawa et al., 1993, "Laser manipulation and assembling of polymer latex particles in solution," Macromolec. in press.

States and Botstein, 1991, "Molecular sequence accuracy and the analysis of protein coding regions," Proc. Natl. Acad. Sci. USA 88:5518–5522.

Edington, 1993, "Breaking open the bottlenecks in genomic DNA sequencing," Bio/Technology 11:39–42.

Courtney and Wilson, 1991, "Multichannel time–correlated single photon counting: spectroscopy and time–gated imaging using a resistive anode photomultiplier tube," Rev. Sci. Instrum. 62(9):2100–2104.

Schematic diagram of a gel

METHODS AND APPARATUS FOR DNA SEQUENCING

This is a division of application Ser. No. 08/376,761, filed Jan. 23, 1995, which is a continuation of application Ser. No. 08/012,862 filed Feb. 1, 1993 now abandoned.

1. INTRODUCTION

Considerable interest has been developing in the past few years to sequence the entire human genome (i.e., all of the genetic material in a human cell). The task, however, is enormous because it involves the sequencing of at least 3,000,000,000 base pairs, an effort which is likely to take ten or more years and cost $3,000,000,000 if undertaken using conventional technology (1993 Edgington, Bio/Technology 11:39–42, which is incorporated herein by reference).

The Committee on Mapping and Sequencing the Human Genome of the National Research Council in their 1988 report entitled, Mapping and Sequencing the Human Genome (which is incorporated herein by reference), stated that, "No foreseeable technology will be able to automate DNA sequencing comprehensively." The present invention is a method and apparatus for comprehensively automating this effort with substantial improvements in speed and cost. The invention is applicable to the sequencing of genetic material from any source, human or otherwise.

2. BACKGROUND OF THE INVENTION

2.1. DNA AND RNA

Deoxyribonucleic acid (DNA) is the primary genetic material of most organisms. Ribonucleic acid (RNA) is the primary genetic material in certain viruses. Additionally, a form of RNA known as messenger RNA (mRNA) is found in all cells and comprises copies of portions of the primary genetic information found in the DNA. In its natural state, DNA is found in the form of a pair of complementary chains of nucleotides which are interconnected as a double helix (see FIG. 1). A nucleotide in turn is compesed of a nitrogenous base (see FIGS. 2 and 3), which identifies the nucleotide, linked by an N-glycosidic bond to a five-carbon sugar. RNA differs from DNA in that in DNA the nucleotide sugar is deoxyribose, while in RNA, the sugar is ribose. A phosphate group serves to link the nucleotides together, formihg the backbone of a single strand of DNA (see FIG. 2). Normally, the nitrogenous base is one of the following: adenine, guanine, thymine and cytosine (respectively denoted A, G, T, and C), or uracil (U) in place of thymidine in RNA (see FIG. 3). The order of the four nucleotides, A, G, T and C, in the chain is often referred to as the sequence of the DNA and can be specified simply by setting down the symbols A, G, T and C in the order in which these four nucleotides appear in the DNA strand.

The two chains (or strands) of a DNA double helix are held together by hydrogen bonding between the nitrogenous bases of their individual nucleotides. This hydrogen bonding is specific in-that adenine in one strand must pair with thymine (or uracil in RNA) in the other strand, and guanine with cytosine. The sequence of bases in one strand of DNA is thus complementary to the sequenceon the other strand.

A DNA chain has polarity: one end of the chain has a free 5'—OH (or phosphate) group (termed "the 5' end") and the other a free 3'—OH (or phosphate) group ("the 3' end"). By convention, the nucleotide sequence is written or read left-to-right in the direction from the 5' end to the 3' end. The two strands of a DNA double helix have opposite polarities. Thus the 5' end of one strand pairs with the 3' end of the Other strand and the complementarity of the two strands is revealed by comparing one strand read,in the 5' to 3' direction with the other strand read in the 3' to 5' direction.

Genetic information is encoded in the particular sequence (order of occurrence) of nucleotides along a DNA molecule and DNA sequencing is the process of determining that order in a particular DNA molecule.

2.2. ENZYMES USED IN DNA SEQUENCING

Two classes of enzyme activity which have been employed in certain methods used to sequence DNA are DNA polymerase and exonuclease activity.

A DNA polymerase is an enzyme that has the ability to catalytically synthesize new strands of DNA in vitro. The DNA polymerase carries out this synthesis by moving along a preexisting single DNA strand ("the template") and creating a new strand, complementary to the preexisting strand, by incorporating single nucleotides one at a time into the new strand following the base-pairing rule described above.

In contrast to polymerase activity, exonuclease activity refers to the ability of an enzyme (an exonuclease) to cleave off a nucleotide at the end of a DNA strand. Enzymes are known which can cleave successive nucleotides in the single DNA strand of a single-chain DNA molecule, working from the 5' end of the strand to the 3' end; such enzymes are termed single-stranded 5' to 3' exonucleases. Other enzymes are known which perform this operation in the opposite direction (single-stranded 3' to 5' exonucleases). There also exist enzymes which can cleave successive nucleotides from the end of a single strand of a double-stranded DNA molecule. These enzymes are termed double-stranded 5' to 3' or 3' to 5' exonucleases, depending on the direction in which they proceed along the strand. Exonucleases are also characterized as being distributive or processive in their action. Distributive exonucleases dissociate from the DNA following each internucleotide bond cleavage, whereas processive exonucleases will hydrolyze many internucleotide bonds without dissociating from the DNA.

2.3. SEQUENCING OF DNA

Approaches to DNA sequencing have varied widely. Use of these enzymes or other chemical methods, as described below, has made it possible to sequence small portions of the human genome. Despite these successes, most of the human genome remains unexplored. Of the 3,000,000,000 base pairs in the human genome, only about 20 million base pairs have been sequenced (GenBank® Release 74—December 1992).

2.3.1. SEQUENCING LADDER METHODS

Many techniques for sequencing DNA have involved generating fragments of labeled DNA, the lengths of which are sequence-dependent, and separating the fragments according. to their lengths by electric field-induced migration in a gel, so as to be able to discern the DNA sequence from the appearance of the separated fragments. Such a pattern of sequence-dependent fragment lengths is known as a sequencing ladder. The fragments can be generated by either: (a) cleaving the DNA in a base-specific manner (see FIG. 4), or (b) synthesizing, a copy of the DNA wherein the synthesized strand terminates in a base-specific manner (see FIG. 5).

The Maxam-Gilbert technique for sequencing (Maxam and Gilbert, 1977, Proc. Natl. Acad. Sci. USA 74:560, which is incorporated herein by reference) involves the specific chemical cleavage of DNA. According to this technique, four samples of the same labeled DNA are each subjected to a different chemical reaction to effect preferential cleavage of the DNA molecule at one or two nucleotides of a specific base identity. By adjusting the conditions to obtain only partial cleavage, DNA fragments are thus generated in each sample whose lengths are dependent upon the position within the DNA base sequence of the nucleotide(s) which are subject to such cleavage. Thus, after partial cleavage is performed, each sample contains DNA fragments of different lengths each of which ends with the same one or two of the four nucleotides. In particular, in one sample each fragment ends with a C, in another sample each fragment ends with a C or a T, in a third sample each ends with a G, and in a fourth sample each ends with an A or a G. The fragments so generated are then separated from one another by electric field-induced migration in a polyacrylamide gel. The four individual sets of fragments produced by cleavage using chemical reactions of different specificity are run side-by-side, in separate lanes of the gel. The DNA fragments are then visualized, and sequence is determined by the observing the position in the gel of the generated fragments.

FIG. 4 schematically depicts the visualization of DNA fragments that are generated by cleaving the labelled DNA having the sequence 5'-AAGTACT-3'-label. The fragments from the four samples are run side-by-side in the four lanes of the gel identified by G, A+G, C, T+C where G identifies the sample in which all the fragments end with guanine nucleotides, A+G identifies the sample in which all the fragments end with either an adenine or a guanine nucleotide, C identifies the sample in which all the fragments end with a cytosine nucleotide, and T+C identifies the sample in which all the fragments end with either a thymine or a cytosine nucleotide. The distance the fragments migrate in the gel is a monotonic function of their length. Thus, after the migrating fragments are visualized, the order of the nucleotides in the labelled DNA molecule can be read directly from the vertical position of the fragments in the gel. The fragments that end with adenine that appear in the A+G lane, and the fragments that end with thymine that appear in the T+C lane, can be distinguished from the fragments in the same lanes that end with guanine and cytosine, respectively, by noting that the fragments that end with guanine and cytosine also appear at the same vertical position in the G and C lanes, respectively.

In the DNA of many organisms, a significant fraction of the cytosines are methylated in vivo at the 5 position to give 5-methylcytosine. Such methylation is involved in the regulation of gene expression and in genetic imprinting. Church and Gilbert (1984, Proc. Natl. Acad. Sci. USA 81:1991-1995; incorporated herein by reference) and Saluz and Jost (1987, "A Laboratory Guide to Genomic Sequencing," BioMethods, Vol. 1, Birkhäuser, Boston; incorporated herein by reference) devised a modification of the Maxam and Gilbert chemical cleavage method to provide a means for directly determining the position of 5-methylcytosine in genomic DNA. In this method, genomic DNA is chemically cleaved, then completely digested with a restriction enzyme and separated by gel electrophoresis, resulting in a complex mixture of superimposed sequencing ladders. The DNA bands forming the rungs of the sequencing ladder are next transferred and cross linked to a nylon membrane. A specific ladder from the mixture is then recognized by hybridizing the membrane with a labeled oligonucleotide probe which uniquely recognizes the sequence immediately adjacent to a particular restriction site. Frommet et al. (1992, Proc. Natl. Acad. Sci. USA 89:1827-1831, which is incorporated herein by reference) have recently developed an alternative genomic DNA sequencing method wherein cytosines in the sample DNA are converted to uracil by bisulfite treatment which leaves 5-methylcytosine unmodified. Comparison of the sequence of modified and unmodified DNA reveals the positions in the sequence of 5'-methylcytosine. Such genomic sequencing methods can only be carried out with genomic DNA. The methylation pattern is lost during gene cloning in microorganisms in vivo, and during DNA copying or amplification in vitro.

The plus/minus DNA sequencing method (Sanger and Coulson, 1975, J. Mol. Biol. 94:441-448, which is incorporated herein by reference) involves: (a) use of DNA polymerase to generate complementary $^{32}$P-labeled DNA oligonucleotides of different lengths; (b) (the "minus" system) in four separate reaction vessels, reaction of one half of the generated DNA with DNA polymerase and three out of the four nucleotide precursors; and (c) (the "plus" system) in four separate reaction vessels, reaction of the remaining half of the generated DNA with DNA polymerase and only one of each of the four nucleotide precursors. Each reaction mixture generated in steps (b) and (c) is subjected to a denaturing polyacrylamide gel electrophoresis. The generated fragments are separated from one another by migration in the polyacrylamide gel; the shorter the fragment, the greater the migration. After visualization of the DNA in the gel by detection of its label, the sequence of the DNA can be determined by observing the position in the gel of the generated fragments.

The dideoxy method of sequencing was published in 1977 by Sanger and his colleagues (Sanger et al., 1977, Proc. Natl. Acad. Sci. USA 74:5463, which is incorporated herein by reference). In contrast to the method of Maxam and Gilbert which relies on specific chemical cleavage to generate fragments with lengths which are sequence-dependent, the Sanger dideoxy method relies on enzymatic activity of a DNA polymerase to synthesize fragments with lengths that are sequence-dependent. The Sanger dideoxy method utilizes an enzymatically active fragment of the DNA polymerase termed E. coli DNA polymerase I, to carry out the enzymatic synthesis of new DNA strands. The newly synthesized DNA strands consist of fragments of sequence-dependent length, generated through the use of inhibitors of the DNA polymerase which cause base-specific termination of synthesis. Such inhibitors are dideoxynucleotides which, upon their incorporation by the DNA polymerase, destroy the ability of the enzyme to further elongate the DNA chain due to their lack of a suitable 3'—OH necessary in the elongation reaction. When a dideoxy nucleotide whose base can appropriately hydrogen bond with the template DNA is thus incorporated by the enzyme, synthesis of the growing DNA strand halts. Thus DNA fragments are generated by the DNA polymerase, the lengths of which are dependent upon the position within the DNA base sequence of the nucleotide whose base identity is the same as that of the incorporated dideoxynucleotide. The fragments so generated can then be separated in a gel as in the Maxam-Gilbert procedure, visualized, and the sequence determined.

For example, for the case of a template DNA molecule having the sequence 5'-GCCATCG-3'-label, FIG. 5 depicts the visualization of the DNA fragments that are generated by the dideoxy method after terminating synthesis at each of the nucleotides G, A, C and T. Since the distance a fragment migrates in the gel is a monotonic function of its length, the sequence of the DNA molecule can be read directly from the gel after the fragments are visualized.

Sanger and colleagues utilized an *E. coli* DNA polymerase I fragment termed the Klenow fragment. After the disclosure of the original Sanger dideoxy technique, the enzyme used in most dideoxy sequencing was the Klenow fragment. Other enzymes with DNA polymerase activity that have been used in sequencing include AMV reverse transcriptase and T7 DNA polymerase Tabor and Richardson, U.S. Pat. No. 4,795,699, which is incorporated herein by reference).

DNA sequencing methods have been automated to varying degrees. In the manual methods, radioactive labels such as $^{32}P$ are typically used identify the bands of the sequencing ladder by autoradiographic imaging on X-ray film. Digital imaging systems and pattern recognition software have been developed by several groups for automatic interpretation and data entry from such autoradiographs (Elder et al., 1986, Nucl. Acids Res. 14:417-424, which is incorporated herein by reference). Real-time recording of the sequencing ladder during gel electrophoresis was made possible by positioning β-emission detectors at the bottom of the gel (EG&G Biomolecular ACUGEN™ Sequencer, Acugen™ System Report 88-106, EG&G Biomolecular), or by employing fluorescent labeling techniques in combination with real-time fluorescence detection during electrophoresis. Smith et al. (1986, Nature 321:674, which is incorporated herein by reference) disclose a method for partial automation of DNA sequencing, which involves use of four different color fluorophores bound to the primer (Smith et al., 1985, Nucl. Acids Res. 13:2399-2412, which is incorporated herein by reference) used for synthesis in one of four reaction vessels, each containing a different dideoxynucleotide in the Sanger dideoxy method. The reaction mixtures are combined and subjected to electrophoresis, during which the separated DNA fragments are identified by a fluorescent detection apparatus, and the sequence information acquired directly by computer. In an alternative approach, the dideoxy nucleotide chain terminators have each been chemically linked to different succinylfluorescein fluorescent dyes which can be distinguished by their fluorescent emission, allowing the four sequencing reactions to be run in a single tube (Prober et al., 1987, Science 238:336, which is incorporated herein by reference). Japanese scientists and engineers are participating in the development of a completely automated DNA sequencing system, employing the Sanger dideoxy method of sequencing (Endo et al., 1991, Nature 352:89-90; Wada et al., 1987, Nature 325:771-772, which are incorporated herein by reference).

Ladder-based sequencing methods are currently the most widely utilized, and variations on the Sanger method of generating the sequencing ladder are used predominantly. The throughput and cost of ladder-based sequencing methods are currently limited by three major factors: (1) the number of resolvable bases in a single ladder, (2) the time required to separate the fragments and generate the ladder, and (3) the number of ladders which can be run in parallel. Numerous efforts are presently underway to further improve each of these aspects and to thereby enhance the performance of ladder-based sequencing methods. Conventional DNA sequencing gels are typically ~300–500 micrometers thick. With such gels it is usually possible to obtain 300–500 bases of sequence from a single sequencing ladder. The limit depends on the ability to resolve a band containing fragments which are N nucleotides long from those containing fragments which are N+1 or N-1 nucleotides in length. Increased resolution can be achieved by employing thinner gels, typically ~25-100 micrometer, either in ultrathin slab gels (Kostichka et al., 1992, Bio/Technology 10:78-81) or in capillary gels (Drossman et al., 1990, Anal. Chem. 62:900-903, which are incorporated herein by reference). It has recently been demonstrated that such gels are capable of resolving >1,000 bases, and further improvements are projected to achieve ~2,000 bases. One approach to further increase the resolution of the gel is to employ programmed pulse-field techniques (C. Turmel, E. Brassard, R. Forsyth, J. Randell, D. Thomas, J. Noolandi (1992) "Sequencing up to 800 bases manually using pulsed field", IN: Genome Mapping & Sequencing, Cold Spring Harbor Laboratory, Abstract #112; C. Turmel, E. Brassard, J. Noolandi (1992) Electrophoresis (in press), which are incorporated herein by reference). Because ultrathin gels can be cooled more efficiently, they can be operated at much higher voltages per unit length, thereby reducing the time required to effect the separation of the sequencing ladder. Multiple capillaries can be run in parallel or a greater number of samples can be loaded in slab gels to further increase throughput. Both capillary and ultrathin slab gels have been demonstrated to have some degree of reusability. In order to achieve the improved performance offered by ultrathin gels, it is necessary to reduce the number of DNA molecules loaded onto the gel, which therefore reduces the number of the DNA molecules in each band or rung of the sequencing ladder. This requires more sensitive detection methods which have included the use of sheath-flow cuvette fluorescence techniques (1991 Chen et al., SPIE Vol. 1435, *Optical Methods for Ultrasensitive Detection and Analysis: Techniques and Applications*, p. 161-167, which is incorporated herein by reference), confocal fluorescence microscopy (1992 Mathies and Huang, "Capillary array electrophoresis: an approach to high-speed, high throughput DNA sequencing," Nature 359:167-169, which is incorporated herein by reference), mass spectrometry (1990 T. Brennan, J. Chakel, P. Bente, M. Field, "New Methods to Sequence DNA by Mass Spectrometry," SPIE Vol. 1206, *New Technologies in Cytometry and Molecular Biology*, pp. 60-77; 1990 T. Brennan, J. Chakel, P. Bente, M. Field, "New Methods to Sequence DNA by Mass Spectrometry," IN: A. L. Burlingame and J. A. McCloskey (Eds.) *Biological Mass Spectrometry*, Elsevier, Amsterdam, pp. 159-177, which are incorporated herein by reference), and resonance ionization spectroscopy (RIS) (1979 G. S. Hurst, M. G. Payne, S. D. Kramer, J. P. Young, "Resonance ionization spectroscopy and one-atom detection", Rev. Mod Phys. 51:767-819; 1991 H. F. Arlinghaus, M. T. Spaar, N. Thonnard, A. W. McMahon, K. B. Jacobson, "Application of resonance ionization spectroscopy for semiconductor, environmental and biomedical analysis, and for DNA sequencing," SPIE Vol. 1435, *Optical Methods for Ultrasensitive Detection and Analysis: Techniques and Applications*, pp. 26-35; 1991 K. B. Jacobson, H. F. Arlinghaus, H. W. Schmitt, R. A. Sachleben, G.M. Brown, N. Thonnard, F. V. Sloop, R. S. Foote, F. W. Latimer, R. P. Woychik, M. W. England, K. L. Burchett, D. A. Jacobson, "An Approach to the Use of Stable Isotopes for DNA Sequencing," Genomics 9:51-59, which are incorporated herein by reference).

Another improvement which was developed from the original genomic sequencing methods is known as multiplex sequencing (Church and Kieffer-Higgins, 1988, Science 240:185-188, which is incorporated herein by reference). In multiplex sequencing, multiple sequencing reactions are pooled and electrophoresed together in a single gel to generate multiple superimposed sequencing ladders which are then transferred and bound to a nitrocellulose membrane. The membrane is then probed with an oligonucleotide which is specific for only one of the pools in order to reveal the corresponding ladder. By repeatedly stripping the membrane of probe and rehybridizing with different oligonhcleotides it is possible to obtain the sequence from each of the individual reactions. Although originally developed using radioactive isotopes to label the probes and therefore requiring lengthy autoradiographic exposures in order to visualize the ladder, newer multiplex sequencing protocols have been devised which employ chemiluminescent detection of the probes (Gillevet, 1990, Nature 348:657–658, which is incorporated herein by reference) or fluorescence detection (Yang and Youvan, 1989, Bio/Technology 7:576–580, which is incorporated herein by reference).

Mass spectrometry offers the potential of further improving ladder-based sequencing by also eliminating the electrophoresis step and replacing it with mass separation of conventional sequencing reaction mixtures using time-of-flight methods which require only milliseconds. Matrix-assisted laser desorption/ionization is currently being explored to generate mass ions as large as ~300,000 daltons without fragmentation which might permit the determination of ~600 bases. (1992 M. C. Fitzgerald, G. R. Parr, L. M. Smith, "DNA Sequence Analysis by Mass Spectrometry?" IN: Genome Mapping & Sequencing, Cold Spring Harbor Laboratory, Abstract #113; 1992 G. R. Parr, M. C. Fitzgerald, L. M. Smith, "Matrix-Assisted Laser Desorption/Ionization Mass Spectrometry of Synthetic Oligodeoxyribonucleotides," Rapid. Commu. Mass. Spec. 6:369–372, which are incorporated herein by reference.) Such an approach was described by McCormick and Amendola as early as 1978 (in Theory, Design and Biomedical Applications of Solid State Chemical Sensors, Cheung. et al. (eds.), CRC Press, West Palm Beach, pp. 219–250, which is incorporated herein by reference).

2.3.2. SEQUENCING BY HYBRIDIZATION

A fundamentally different approach to sequencing involves the determination of all of the oligonucleotide sequences contained within a longer sequence. The method is based on the ability of short oligonucleotides to match or hybridize perfectly through base-pairing with their complementary sequence in another DNA molecule (Strezoska et al., 1991, Proc. Natl. Acad. Sci. USA 88:10089–10093; Bains, 1992, Bio/Technology 10:757–58, which are incorporated herein by reference). Under appropriate conditions, only perfect matches are formed and even single base differences prevent successful hybridization. The method can be practiced either with the sample DNA immobilized on an appropriate solid support and the hybridizing oligonucleotides in solution, or with the oligonucleotide probes bound to the solid support and the sample DNA in solution. By establishing which oligonucleotides bind perfectly to the DNA, it is possible to reconstruct the sequence of the DNA. Repeat sequences in the sample DNA which are longer than the length of the oligonucleotide probes employed, result in branch points in the DNA sequence which must be resolved by other methods, therefore limiting the general utility of this method.

2.3.3. SEQUENCING BY MICROSCOPY

Beer and Moudrianakis (1962, Proc. Natl. Acad. Sci. USA 48:409–416, which is incorporated herein by reference) proposed a method for sequencing single DNA molecules, wherein base-specific labeling with heavy elements would allow subsequent electron microscopic observation and identification of the individual bases. Despite almost ten years of subsequent effort, this approach was never successfully reduced to practice. A proposal was made by McCormick and Amendola (1978, in Theory, Design and Biomedical Applications of Solid State Chemical Sensors, Cheung et al. (eds.), CRC Press, West Palm Beach, pp. 219–250, which is incorporated herein by reference) to sequence single DNA molecules by transporting a linearly-extended DNA molecule using a microminiature, iterative system of electrostatic quadrupole lenses past a microminiaturized radial array of electron guns and detectors. Such a design was never realized in practice, but presaged the development of the scanning tunneling microscope (STM) by Binnig and Rohrer (1982, Phys. Rev. Lett. 49:57, which is incorporated herein by reference) and its application to sequencing. Binnig and Rohrer themselves were the first to report images of DNA molecules made with the STM (1984, in Trends in Physics, J. Janta and J. Pantoflicek (eds.), European Physical Society, The Hague, pp. 38–46, which is incorporated herein by reference), and numerous scientific publications have appeared in the past decade purporting to show images of DNA (Driscoll et al., 1990, Nature 346:294–296 and Dunlap and Bustamante, 1989, Nature 342:204–206, which are incorporated herein by reference). Many of these reports have recently been shown to have likely been artifacts of the highly ordered pyrolytic graphite substrate (Clemmer and Beebe, 1991, Science 251:640–642). Research effort continues on microscopy-based approaches to sequencing, including a wider range of techniques such as atomic force microscopy (Hansma et al., 1991, J. Vac. Sci. Technol. B 9:1282–1284, which is incorporated herein by reference) and near-field microscopy (1992 E. Betzig, J. K. Trautman "Near-Field Optics: Microscopy, Spectroscopy, and Surface Modification Beyond the Diffraction Limit," Science 257-189-195, which is incorporated herein by reference). X-ray diffraction techniques have also been proposed for use in DNA sequencing (1991 J. W. Gray, J. Trebes, D. Peters, U. Weier, D. Pinkel, T. Yorkey, J. Brase, D. Birdsall, R. Rill, "Investigation of the Utility of X-ray Diffraction in DNA Sequence Analysis," DOE Human Genome Program, Report of the Second Contractor-Grantee Workshop, Feb. 17–20, 1991, Santa Fe, New Mexico, P56, page 80, which is incorporated herein by reference).

2.3.4. BASE-AT-A-TIME METHODS

Nucleotide Incorporation

Melamede (U.S. Pat. No. 4,863,849, which is incorporated herein by reference) discloses an automatable process, for determining the nucleotide sequence of DNA and RNA involving the determination of whether a specific one of the four nucleotides is incorporated by polymerase at the nucleotide residue 3' of the primer terminus.

Nucleotide Cleavage

In an early approach, Cantor et al. (1964, Biopolymers 2:51–63, which is incorporated herein by reference) mathematically analyzed the kinetics of exoenzyme digestion of linear polymers and proposed the use Of exonuclease under non steady-state conditions to sequentially remove terminal nucleotides from a population of RNA molecules. By monitoring the evolution of the resulting mononucleotides with time, they calculated that it should be possible to determine the base sequence of oligomers up to 25 nucleotides.

Synchronization

The experimental difficulty with such an approach is that there is no means available for synchronizing the hydrolytic action of the individual exonuclease molecules. The cleavage of an internucleotide bond is a stochastic process and there is therefore a time distribution for cleavage of each bond rather than a discrete time interval. The consequence is that each individual DNA chain is hydrolyzed at a slightly different rate. Even though all of the DNA molecules start with identical terminal nucleotides, they quickly evolve to a mixed population having different terminal nucleotides as some chains are degraded more slowly or rapidly than others. The ability to derive sequence information by such terminal cleavage is therefore limited by the point at which the terminal nucleotides have become sufficiently random within the population of DNA molecules to mask the signal from those chains which are still synchronous.

One solution to this synchronization problem would be to devise an exonuclease wherein internucleotide bond cleavage is triggered by a very short light pulse. The hydrolytic action of the exonuclease would thus be synchronized to an external source. Enzymes with similar properties are known in the art. Photoreactivating enzyme (EC 4.1.99.3 Deoxyribodipyrimidine photolyase) binds to UV-induced dimers formed between adjacent pyrimidines in DNA, cleaving the cyclobutane dimers upon absorption of near-UV light. Photoinitiated nuclease activity has not been described, but a DNA-binding protein, the trp repressor, has been successfully converted to a site-specific nuclease by chemical modification (Chen and Sigman, 1987, Science 237:1197–1201, which is incorporated herein by reference) and oligonucleotides have been chemically modified to incorporate photosensitizers which permit the photoinduced cleavage of DNA (Le Doan et al., 1987, Nucleic Acids Res. 15:7749–7760; Praseuth et al., 1988, Proc. Natl. Acad. Sci. USA 85:1349–53, which are incorporated herein by reference).

An alternative solution to the synchronization problem would be to avoid the issue altogether by going to the limit of a single DNA molecule, rather than sequencing a population of molecules. In a lecture given at the dedication of Jadwin and Fine Halls, Princeton University, Mar. 17, 1970, Freeman Dyson outlined a proposed method for rapidly sequencing single DNA molecules one base at a time (1992 Dyson, *From Eros to Gaia*, Pantheon Books, New York, p. 155, which is incorporated herein by reference). Dyson proposed to isolate a single DNA molecule, attach one end to a solid support, and extend the molecule under the influence of an electric field in vacuo. Single nucleotides are then removed one by one in sequence from the loose end of the chain, ionized and directed into a mass spectrometer which sorts the nucleotides into four channels labeled adenine, cytosine, guanine and thymine. Counters in each channel automatically record the sequence in which the nucleotide arrives. Jett et al. (U.S. Pat. No. 4,962,037; 1989, J. Biomolecular Structure and Dynamics 7(2):301–309; 1989, Book of Abstracts, Sixth Conversation in Biomolecular Stereodynamics, SUNY at Albany, Jun. 6–10, 1989, p. 157; and Davis et al., 1991, GATA 8(1):1–7, which are incorporated herein by reference) disclose a quite similar method for DNA or RNA sequencing, involving the sequencing of single nucleic acid molecules containing nucleotides tagged with a fluorescent dye, which molecules are suspended in a flow stream and subjected to exonuclease digestion to liberate single nucleotides sequentially. The nucleotides are transported by the moving flow stream in an orderly train and identified by fluorescent detection methods. Shera et al. (U.S. Pat. No. 4,793,705; 1990, Chemical Physics Letters 174(6):553–557, which are incorporated herein by reference) and Soper et al. (1991, Anal. Chem. 63:432–437, which is incorporated herein by reference) describe single molecule detection systems, for use, e.g., in detecting a fluorescently labeled nucleotide.

2.3.5. REVIEWS

Current methods, prospects for automation, and novel methods of DNA sequencing are reviewed by Martin and Davies (1986, Bio/Technology 4:890–895), by Bains (1990, Bio/Technology 8:1251–1256) and by Hunkapiller et al., (1991, Science, 254:59 which are incorporated herein by reference).

2.4. RNA SEQUENCING METHODS

RNA sequencing methods are also known. Zimmern and Kaesberg (1978, Proc. Natl. Acad. Sci. USA 75:4257–4261, which is incorporated herein by reference) disclose the use of AMV reverse transcriptase with dideoxy-nucleotides to sequence encephalomyocarditis virus RNA. Mills and Kramer (1979, Proc. Natl. Acad. Sci. USA 76:2232–2235, which is incorporated herein by reference) describe the use of Qβ replicase and the nucleotide analog inosine for sequencing RNA in a chain-termination mechanism. Direct chemical methods for sequencing RNA are also known (Peattie, 1979, Proc. Natl. Acad. Sci. USA 76:1760–1764, which is incorporated herein by reference). Other methods include those of Donis-Keller et al. (1977, Nucl. Acids Res. 4:2527–2538), Simonesits et al. (1977, Nature 269:833–836), Axelrod et al. (1978, Nucl. Acids Res. 5:3549–3563), and Kramer et al. (1978, Proc. Natl. Acad. Sci. USA 75:5334–5338, which are incorporated herein by reference).

2.5. SINGLE-MOLECULE DETECTION

Interest in analytical techniques for optical detection and measurement of spectral properties of single atoms and molecules goes back more than two decades. Initial success was achieved with very dilute atomic and molecular beams in vacuo where background emissions and scattering are most easily minimized. A more challenging problem has been the detection of single molecules in condensed phases.

2.5.1. IN VACUO

Initial success in the optical detection of single atoms was reported by Greenless et al. (1977, Opt. Commun. 23:236–239, which is incorporated herein by reference). Further improvements in optical trapping and laser cooling extended these results to other atomic and ionic systems (Pan et al., 1980, Opt. Lett. 5:459–461; 1980 Neuhauser et al., Phys. Rev. A, 22:1137–1140, which are incorporated herein by reference). By 1986 quantum jumps in single trapped and laser-cooled barium and mercury ions were reported by Nagourney et al. (1986, Phys. Rev. Lett. 56:2797) and by Bergquist et al. (1986, Phys. Rev. Lett. 57:1699–1702, which are incorporated herein by reference). Nagourney reported that the blinking of the fluorescence from a single ion was clearly visible to the naked eye (Robinson, 1986, Science 234:24–25, which is incorporated herein by reference).

2.5.2. IN LIQUID

In liquids, fluorescent detection of single molecules is made more difficult by background fluorescence from other molecules present in the excitation volume, and by both Rayleigh and Raman scattering from the solvent molecules in the excitation volume. One approach to minimizing the background is therefore to reduce the excitation volume. Hirschfeld (1977, SPIE: Multidisciplinary Microscopy 104:16–20, which is incorporated herein by reference) employed the use of attenuated total reflection illumination to limit the dimensions of the excitation volume to the depth of penetration of the evanescent wave field in the sample (~λ/20). Single molecules of γ-globulin were fluorescently tagged by binding to one molecule of polyethyleneimine (~20,000 MW) with ~80 fluorescein isothiocyanate groups attached (Hirschfeld, U.S. Pat. No. 4,166,105, which is incorporated herein by reference) and detected by spreading at a concentration of ~1 molecule/100 µ² and recording photon counts collected by a microscope objective which was scanned across the sample (Hirschfeld, 1976, Applied Optics 15:2965–2966, which is incorporated herein by reference). Hirschfeld (U.S. Pat. No. 3,872,312, which is incorporated herein by reference) also applied spatial filtering either to the excitation light source or to the fluorescent emission as a means of limiting the excitation volume.

Another approach to minimizing excitation volume is to employ hydrodynamically focused flow in a sheath-flow cuvette in combination with focused laser excitation and spatial filtering of the fluorescent emission. Dovichi et al. (1983, Science 219:845–847, which is incorporated herein by reference) used such an approach to detect ~35,000 molecules of the fluorescent dye Rhodamine 6G, and projected improvements which would permit single molecule detection. Subsequent refinement of the technique (Dovici et al., 1983, SPIE: Laser-based Ultrasensitive Spectroscopy and Detection V 426:71–73; Trkula et al., 1984, in Analytical Chemistry Symposium Series, Vol. 19, pp. 53–55; Dovichi et al., 1984, Anal. Chem. 56:348–354; Zarrin and Dovichi, 1985, Anal. Chem. 57:2690–2692; Nguyen et al., 1987, J. Opt. Soc. Am. B 4:138–143; Mathies and Stryer, 1986, in Applications of Fluorescence in the Biomedical Sciences, Alan R. Liss, Inc., pp. 129–140, which are incorporated herein by reference) resulted in the successful detection of single molecules of the highly-fluorescent protein phycoerythrin containing 34 bilin chromophores by both Nguyen et al. (1987, Anal. Chem. 59:2158–2161) and Peck et al. (1989, Proc. Natl. Acad. Sci. USA 86:4087–4091, which are incorporated herein by reference). Yet further improvements resulted in single fluorophore detection for single molecules of Rhodamine 6G in ethanol by Soper et al. (1991, Anal. Chem. 63:432–437, which is incorporated herein by reference). The additional use of pulsed laser excitation with time-correlated single photon counting detection to further eliminate the background from prompt scattering permitted the detection of single molecules of Rhodamine 6G in water by Shera et al. (1990, Chem. Phys. Lett. 174:553–557, which is incorporated herein by-reference).

Riglet and Widengren (1990, in Bioscience, B. Klinge & C. Owmar (eds.), pp. 180–183, which is incorporated herein by reference) used the diffraction limited Gaussian beam waist of a laser focused in a drop of dilute aqueous dye solution to define an excitation volume of only ~6 femtoliters. Using continuous laser excitation and autocorrelation of the fluorescence, they were able to detect the diffusion of single Rhodamine 6G molecules through this excitation volume.

2.5.3. IN SOLID

Detection of single molecules in a solid matrix is similar to detection in liquid, with the added complexity that the individual molecular sites provide heterogeneous local environments which affect the optical properties of the molecule. An approach similar to that of Riglet and Wedengren was employed by Orrit and Bernard (1990, Phys. Rev. Lett. 65:2716–2719, which is incorporated herein by reference) to detect the fluorescence from single molecules of pentacene in ultrathin p-terphenyl crystals. Further refinements of the method by Ambrose and Moerner (1991, Nature 349:225–227; 1991, J. Chem. Phys. 95:7150–7163; 1991, SPIE: Optical Methods for Ultrasensitive Detection and Analysis: Techniques and Applications 1435:244–250, which are incorporated herein by reference) have permitted the recording of the fluorescence excitation spectra of individual pentacene molecules by scanning the p-terphenyl crystal with the tightly focused laser beam.

2.6. NATIVE NUCLEOTIDE FLUORESCENCE

In the base-at-a-time single DNA molecule sequencing method proposed by Jett et al. (U.S. Pat. No. 4,962,037; 1989, J. Biomolecular Structure and Dynamics 7(2):301–309; 1989, Book of Abstracts, Sixth Conversation in Biomolecular Stereodynamics, SUNY at Albany, Jun. 6–10, 1989, p. 157; Davis et al., 1991, GATA 8(1):1–7; Soper et al., 1991, SPIE: Optical Methods for Ultrasensitive Detection and Analysis: Techniques and Applications 1435:168–178, which are incorporated herein by reference) it is repeatedly noted that the individual free and bound bases found in DNA have intrinsic fluorescence, quantum yields $<10^{-3}$ at room temperature, thus necessitating the use of tagged nucleotides wherein fluorescent dyes are covalently attached to the individual bases. The method further requires that these dye-tagged nucleotides first be efficiently and accurately incorporated into a synthetic copy of the DNA template by a suitable polymerase, and then subsequently cleaved with high efficiency by a suitable exonuclease. The considerable, if not insurmountable, difficulty in explicitly defining a compatible set of dyes, linker chemistry, polymerase and exonuclease have thus far prevented the successful reduction to practice of their approach, despite a considerable research effort which has been funded at a level in excess of $1 million per year for many years (1988 Jett et al., "Advanced Concepts for Base Sequencing in DNA" In: *The Human Genome Initiative of the U.S. Department of Energy*, DOE/ER-0382, p. 33; 1990 Jett et al., "Advanced Concepts for Base Sequencing in DNA" In: *Human Genome 1989–90 Program Report*, DOE/ER-0446P, p. 94; 1991 Davis et al., "Rapid DNA Sequencing Based Upon Single Molecule Detection", S21, p. 24 and Soper et al., "Single Molecule Detection of Nucleotides Tagged with Fluorescent Dyes", P87 p. 103, In: *DOE Human Genome Program: Report of the Second Contractor-Grantee Workshop*, U.S. Dept. of Energy; 1991 Parker, "Los Alamos, Firm Join in Gene Mapping", *Albuquerque Journal*, Friday, Mar. 22, 1991; 1992 Jett et al., "Rapid DNA Sequencing Based on Fluorescence Detection of Single Molecules", In: *Human Genome 1991–92 Program Report*, DOE/ER-0544P, p. 129; 1992 Harding and Keller, "Single-molecule detection as an approach to rapid DNA sequencing", *Trends in Biotechnology*, 10:55–57, which are incorporated herein by reference).

However, conditions under which the native nucleotides have quantum yields equivalent to highly fluorescent dyes are known in the prior art. For example, Børresen (1967, Acta Chemica Scand. 21:920–936, which is incorporated herein by reference) reports a quantum yield of fluorescence of 0.93 for guanosine excited at 286 nm in 1:9 (v/v) water:methanol 0.01 N $H_2SO_4$ at 147° K. The major factors contributing to the significant increase in quantum yield are protonation of the base, increase in the viscosity of the solvent and decrease in temperature. A detailed investigation of the effects of both solvent and temperature on the fluorescence quantum yield of adenine was conducted by Eastman and Rosa (1968, Photochem. Photobiol. 7:189–201, which is incorporated herein by reference). They also observed a correlation between quantum yield and the viscosity of the solvent with the highest quantum yields recorded from the most viscous solvent tested, glycerol. The authors also noted that an even more viscous solvent matrix, polyvinyl alcohol, yielded observable fluorescence at room temperature. They concluded that the most cohesive and rigid solvent matrix. (i.e., the solvent with the maximum extent uf intrasolvent hydrogen bonding) produced the highest quantum yield by restricting the mobility of the nucleotide, thereby reducing the opportunity for internal conversion and non-radiative deexcitation. Guéron et al. (1974, in Basic Principles in Nucleic Acid Chemistry, Paul O. P. Ts'O (ed.), pp. 311–398, which is incorporated herein by reference) recorded a three order of magnitude increase in the quantum yield of fluorescence for neutral TMP (thymidine monophosphate) in ethylene glycol:water as the temperature was decreased from room temperature to 77° K.

2.7. FLUORESCENT NUCLEOTIDE ANALOGS

Intermediate between the enhancement of native nucleotide fluorescence described supra and the use of dye-tagged nucleotides as proposed by Jett (U.S. Pat. No. 4,962,037 which is incorporated herein by reference) in which fluorescent dyes are covalently attached to nucleotide bases by means of linker arms, is the use of fluorescent nucleotide analogs (1975 Leonard and Tolman, In: *Chemistry, Biology, and Clinical Uses of Nucleoside Analogs*, A. Bloch (ed), Annals of the New York Academy of Sciences, Vol. 255, p. 43–58, which is incorporated herein by reference). Such analogs are obtained by simple chemical modifications of the basic ring structure of the purine or pyrimidine core of the native nucleotides, or by different chemical substitutions on the rings. The resulting nucleotide analogs are similar in size and shape to the native nucleotides, in contrast with the considerable additional mass and steric constraints involved in linkers and covalent attachment of dyes. As a natural consequence of this general conservation of molecular size and shape among the nucleotide analogs, many are substrates for a variety of DNA or RNA polymerases and can be incorporated into polynucleotides. Similarly, many exonucleases can remove such nucleotide analogs when they have been incorporated into polynucleotides. For those analogs where the chemical modifications do not seriously disrupt the normal hydrogen bonding pattern of native nucleotides, the fidelity of such enzymatic incorporation of analogs is maintained. Some nucleotide analogs are highly fluorescent in aqueous solution at room temperature, in contrast with the native nucleotides. In other cases, the fluorescence of nucleotide analogs increases with decreasing temperature, as observed for native nucleotides, but with increased quantum yields of fluorescence over their native nucleotide counterparts.

Ward et al. have studied the fluorescence properties of a number of nucleotide analogs, as well as their incorporation into and removal from polynucleotides (1969 J. Biol. Chem. 244:1228–1237; 1969 J. Biol. Chem. 244:3243–3250; 1972 J. Biol. Chem. 247:705–719; 1972 J. Biol. Chem. 247:4014–4020, which are incorporated herein by reference). The analogs investigated included formycin, 2-aminopurine, 2,6-diaminopurine, and 7-deazanebularin.

3. SUMMARY OF THE INVENTION

The present invention is a method and apparatus for automated DNA sequencing. As used herein, the term "DNA" or "deoxyribonucleic acid" shall be construed as collectively including DNA containing classical nucleotides, DNA containing one or more modified nucleotides (e.g., dye-tagged nucleotides containing a chemically or enzymatically modified base, sugar, and/or phosphate), DNA containing one or more nucleotide analogs, and combinations of the above, except where clearly or expressly defined otherwise. As used herein, the term "nucleotide" shall be construed as collectively including all of the forms of nucleotides described supra, except where clearly or explicitly stated otherwise. In general, the method of the invention comprises the steps of cleaving from a single DNA strand the next available single nucleotide on the strand, transporting the single nucleotide away from the DNA strand and identifying the single cleaved nucleotide. Preferably, the method of the invention comprises the steps of: a) using a processive exonuclease to cleave from a single DNA strand the next available single nucleotide on the strand; b) transporting the single nucleotide away from the DNA strand; c) incorporating the single nucleotide in a fluorescence-enhancing matrix; d) irradiating the single nucleotide to cause it to fluoresce; e) detecting the fluorescence; f) identifying the single nucleotide by its fluorescence; and g) repeating steps a) to f) indefinitely (e.g., until the DNA strand is fully cleaved or until a desired length of the DNA is sequenced). In the preferred embodiment of the present inventioin, the necleotide is not bound to a fluorescent molecule (e.g., fluorescein and other dyes); rather the fluorescence of the nucleotide itself is detected.

In an alternative embodiment of the invention, the natural fluorescent activity of a nucleotide analog cleaved from the DNA is detected; such analogs include but are not limited to 2-aminopurine, formycin, 2,6-diaminopurine, 7-deazanebularin. In another alternative embodiment of the invention, the fluorescence of dye-tagged nucleotides is detected. In yet another embodiment of the invention, sequencing is accomplished by detecting the fluorescence of various combinations of native nucleotides, nucleotide analogs and dye-tagged nucleotides.

Advantageously, the DNA strand is positioned in a flowing aqueous solution and the cleaved nucleotide is transported from the DNA strand by the flowing solution. The flowing solution is then injected into a flowing sheath solution such as propane that is immiscible with the aqueous solution. The flowing solutions are then cooled to a temperature in the range of 170° to 85° K., vitrifying the aqueous solution but not the sheath solution, before the nucleotide is irradiated. This greatly enhances the natural fluorescent activity of the nucleotide.

Specific apparatus for implementing the invention comprises a cleaving station, a transport system and a detection station. The cleaving station preferably includes equipment for the extraction and purification of DNA from cells. Such equipment advantageously comprises a sample chamber for sorting and isolating cells as well as a culture chamber. Following known methods, an appropriate culture medium can be introduced into the culture chamber to cause a cell to undergo DNA replication but to arrest the cell replication cycle in metaphase at a point where the cell can be disrupted and the chromosomes of the cell released. The equipment also comprises a microchannel leading from the culture chamber to additional chambers for isolating the individual chromosomes. The chromosome chambers, in turn, are connected to the cleaving station by a microchannel.

The cleaving station itself is a progressively narrower capillary channel with means for immobilizing the DNA strand in an aqueous solution that flows through the channel and means for introducing a processive exonuclease into the channel at the downstream end of the strand. Illustratively, the DNA strand is immobilized by attaching its upstream end to a substrate and suspending the substrate along the central axis of the capillary channel. For example, the substrate can be a microsphere that is suspended in the entrance to the channel by a focused laser beam. Advantageously, the exonuclease is introduced through a side channel that enters the capillary channel at a point where the downstream end of the DNA strand is suspended.

The transport system illustratively includes means for flowing an aqueous solution past the suspended DNA strand so as to entrain the nucleotides as they are cleaved and means for injecting the nucleotide-bearing aqueous solution into a flowing sheath solution. Advantageously, the system also includes means for hydrodynamically focusing the aqueous solution within the flowing sheath solution as well as means for cooling the aqueous solution and the sheath solution to a temperature of about 170° to 85° K., thereby vitrifying the aqueous solution and providing a fluorescence-enhancing matrix for nucleotide detection.

The detection station comprises a source of radiation which preferably is a high repetition rate pulsed laser for stimulating natural fluorescence from the nucleotides, a detection system for detection of fluorescence from the nucleotides, and means for identifying the nucleotide from the detected fluorescence. Advantageously the nucleotide is identified by a best fit comparison of features of the time-resolved spectrum of the detected fluorescence with previously recorded spectra of the four nucleotides.

4. DESCRIPTION OF THE FIGURES

These and other objects, features and advantages of the invention will be more readily apparent from the following detailed description of the invention in which.

Figure 8:
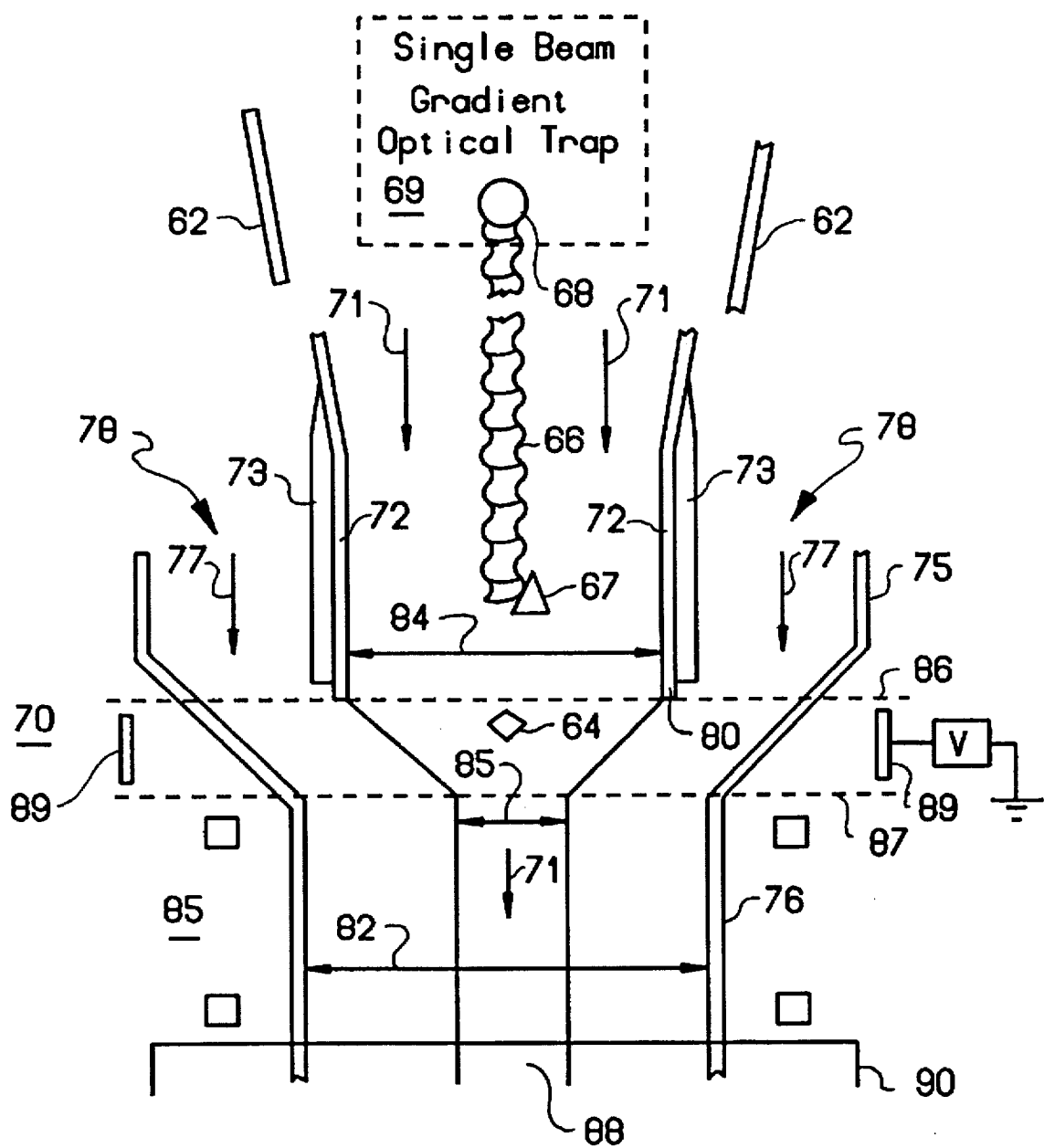
FIG. 8 depicts certain details of the embodiment of FIG. 7.
Figure 9:
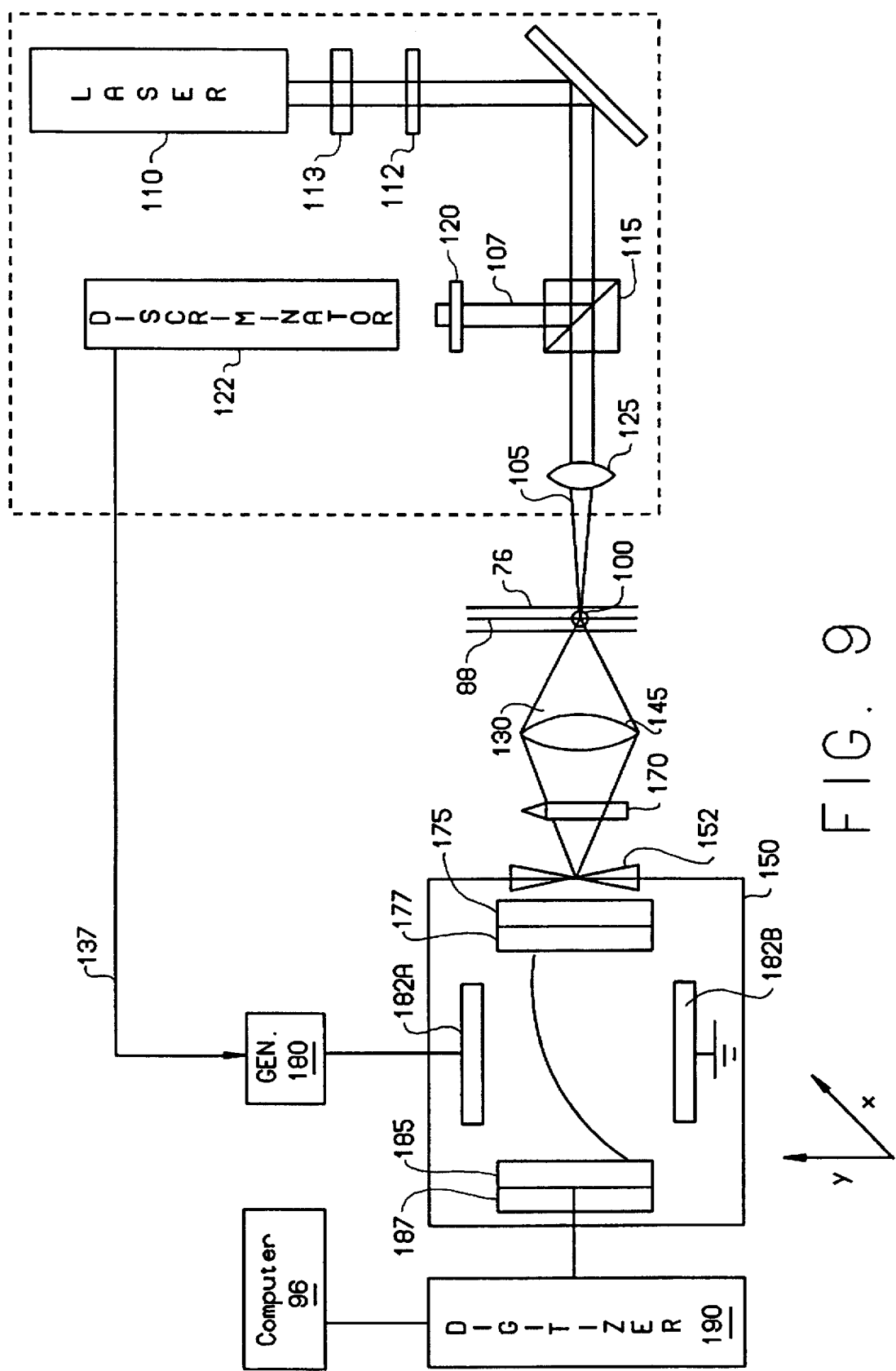
FIG. 9 depicts certain other details of the embodiment of FIG. 7.
Figure 14:
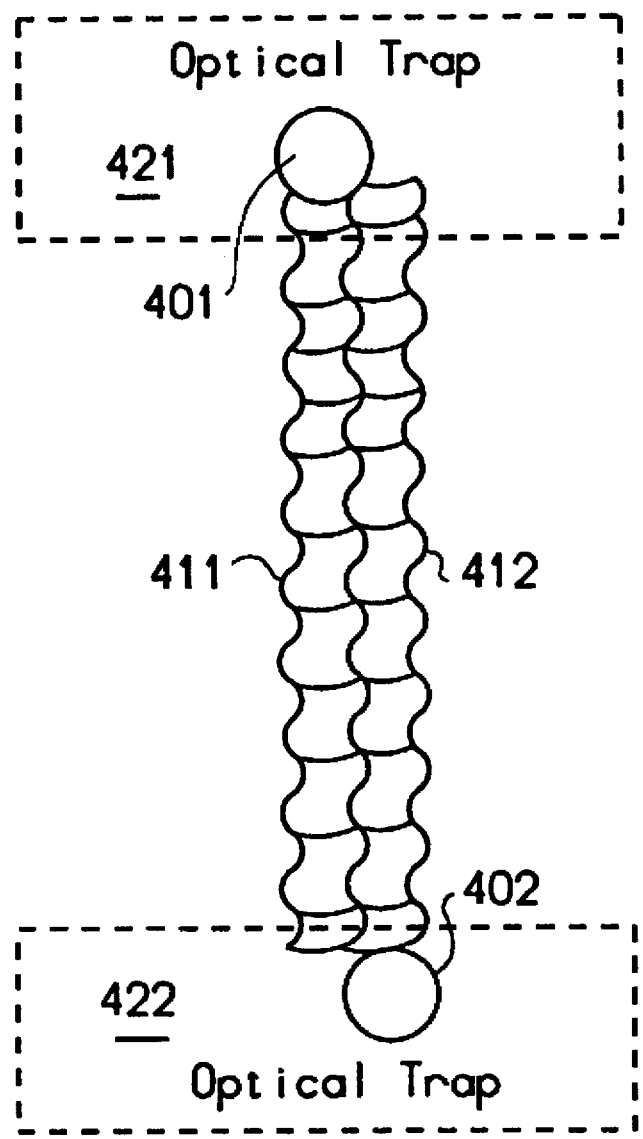
Figure 15:
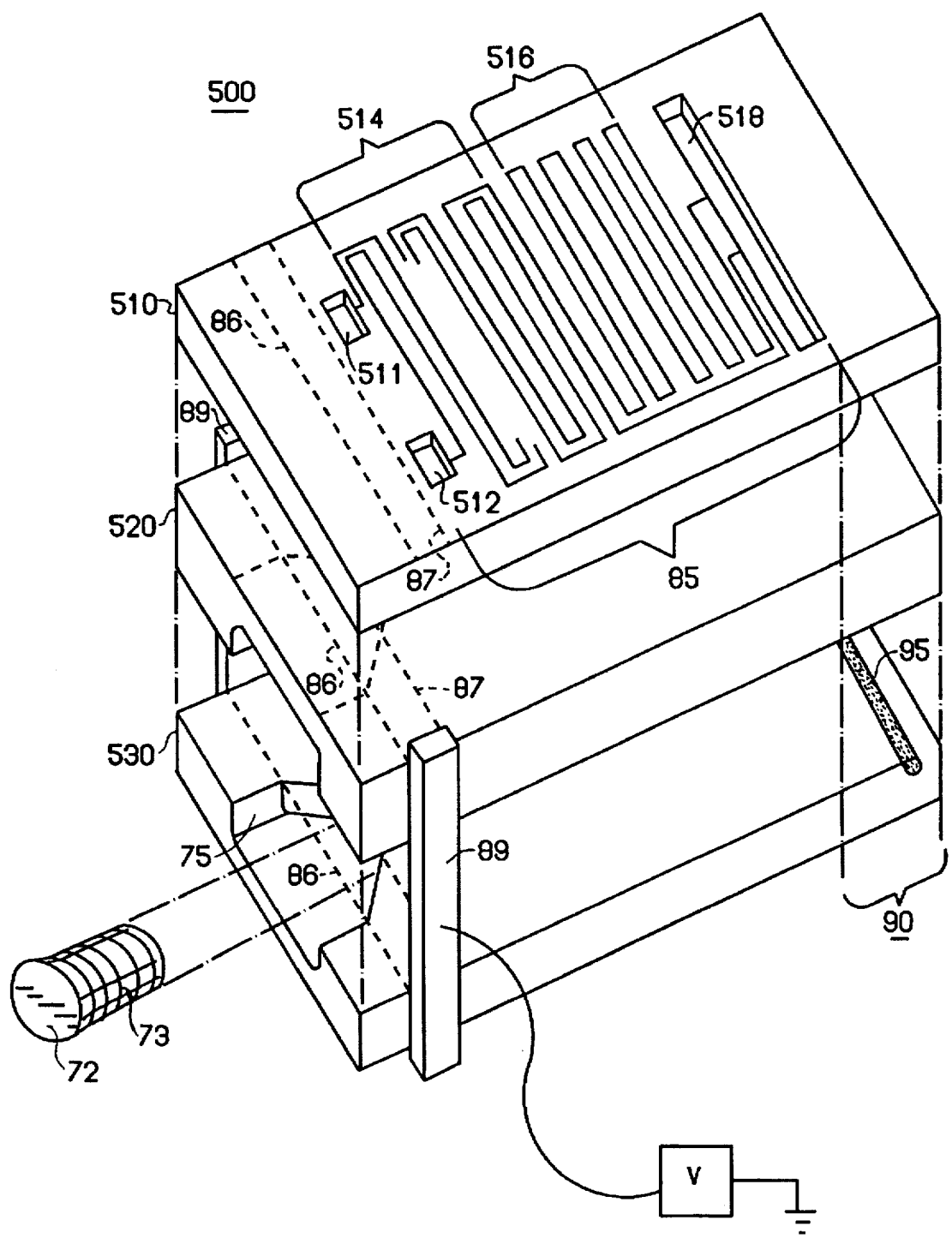

FIG. 14 provides an illustration useful in understanding a portion of the disclosure; and FIG. 15 depicts certain details of the apparatus of FIGS. 8 and 9.

5. DETAILED DESCRIPTION OF THE INVENTION

Figure 1:
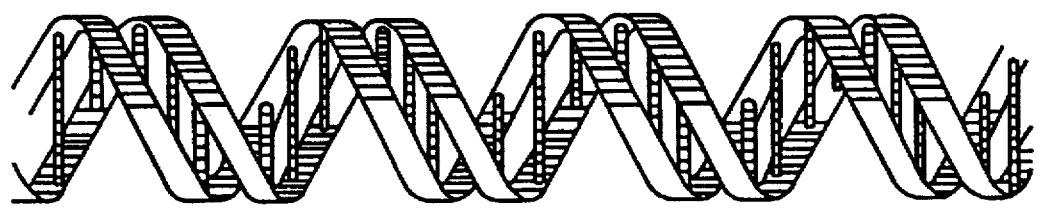
FIG. 1 is a schematic illustration of a double-strand of DNA.
Figure 2:
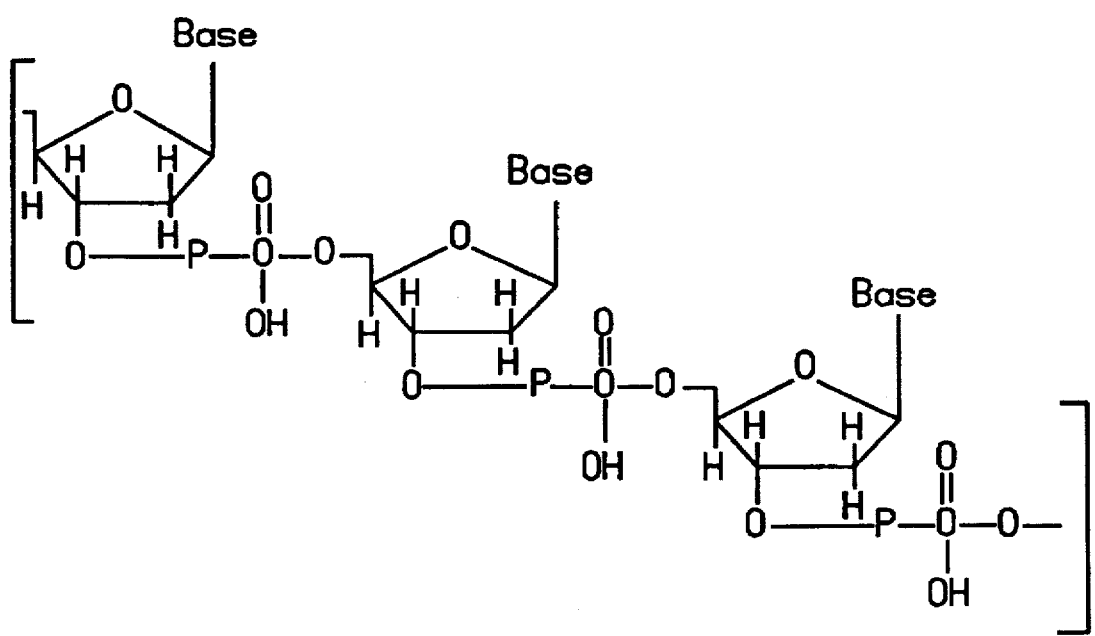
FIG. 2 is a schematic illustration of a segment of DNA.
Figure 3:
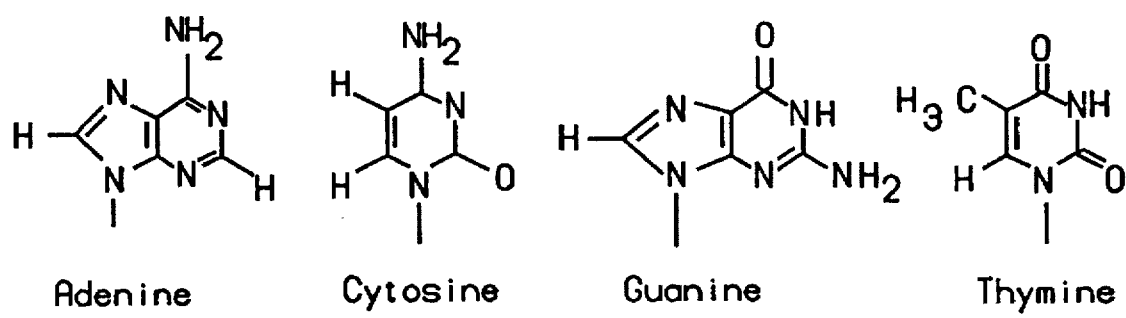
FIG. 3 is a schematic illustration of the chemical structure of the nucleotides.
Figure 4:
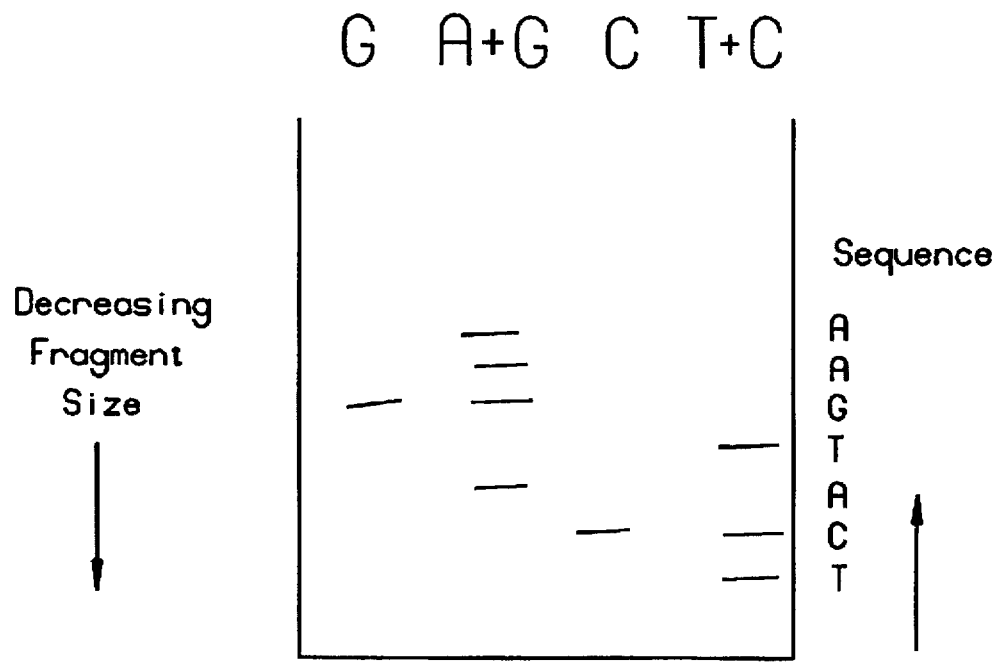
FIGS. 4 and 5 illustrate prior art sequencing methods.
Figure 5:
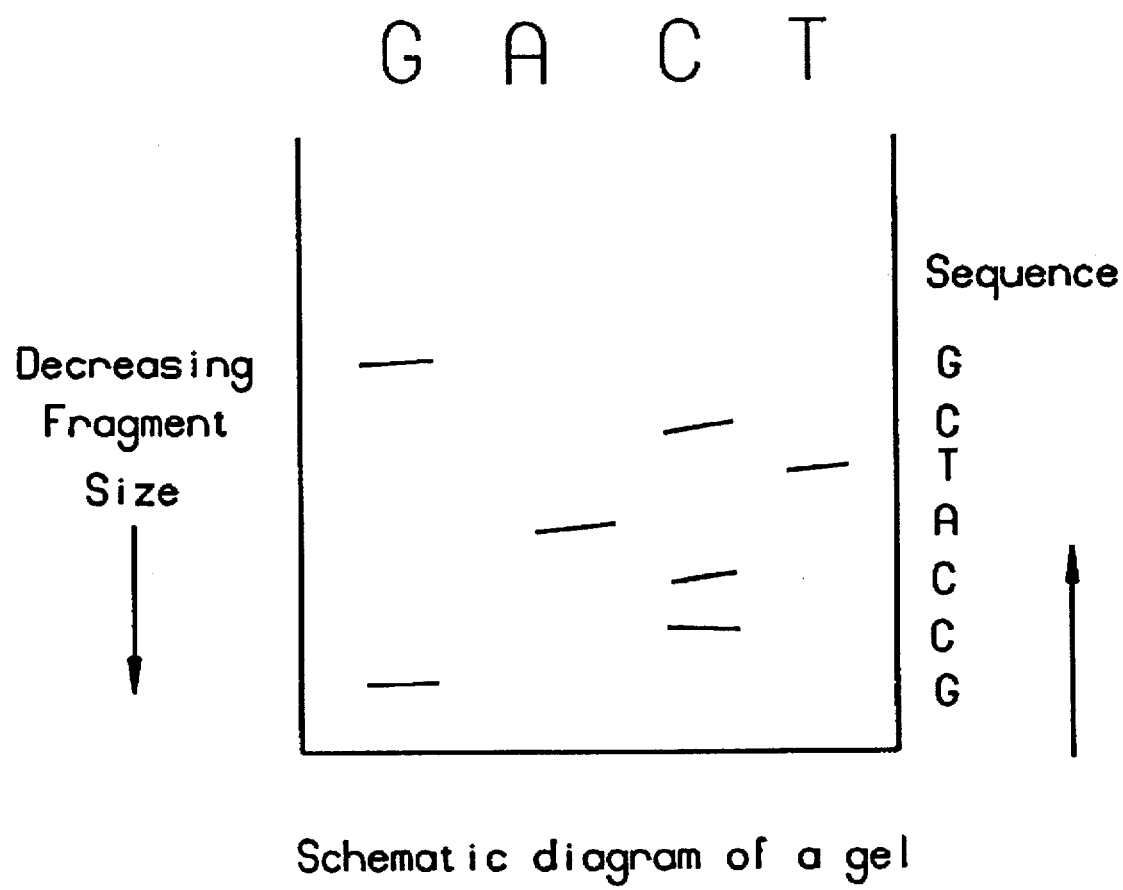
Figure 6:
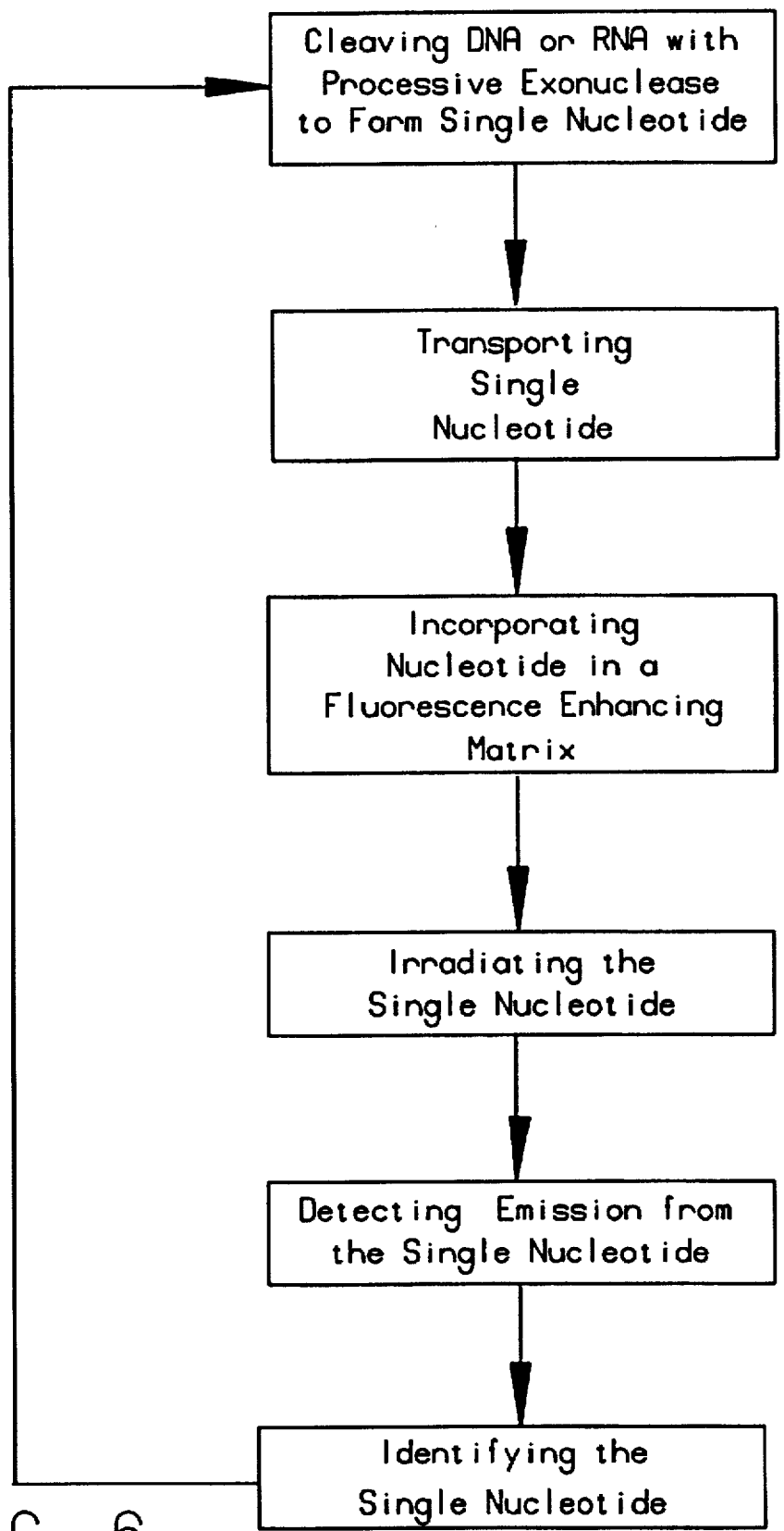
FIG. 6 is a flow chart depicting an illustrative embodiment of the method of the present invention.

In general, the method of the invention comprises the steps of cleaving from a single DNA strand the next available single nucleotide on the strand, transporting the single nucleotide away from the DNA strand and identifying the single cleaved nucleotide. As shown in FIG. 6, a preferred embodiment of the method of the present invention comprises the steps of:

a) using a processive exonuclease to cleave from a single DNA strand the next available single nucleotide;

b) transporting the single nucleotide away from the DNA strand;

c) incorporating the single nucleotide in a fluorescence-enhancing matrix;

d) irradiating the single nucleotide in said matrix to cause the single nucleotide to fluoresce;

e) detecting the fluorescence;

f) identifying the single nucleotide by its fluorescence; and g) repeating steps a) to f) indefinitely.

Figure 7:
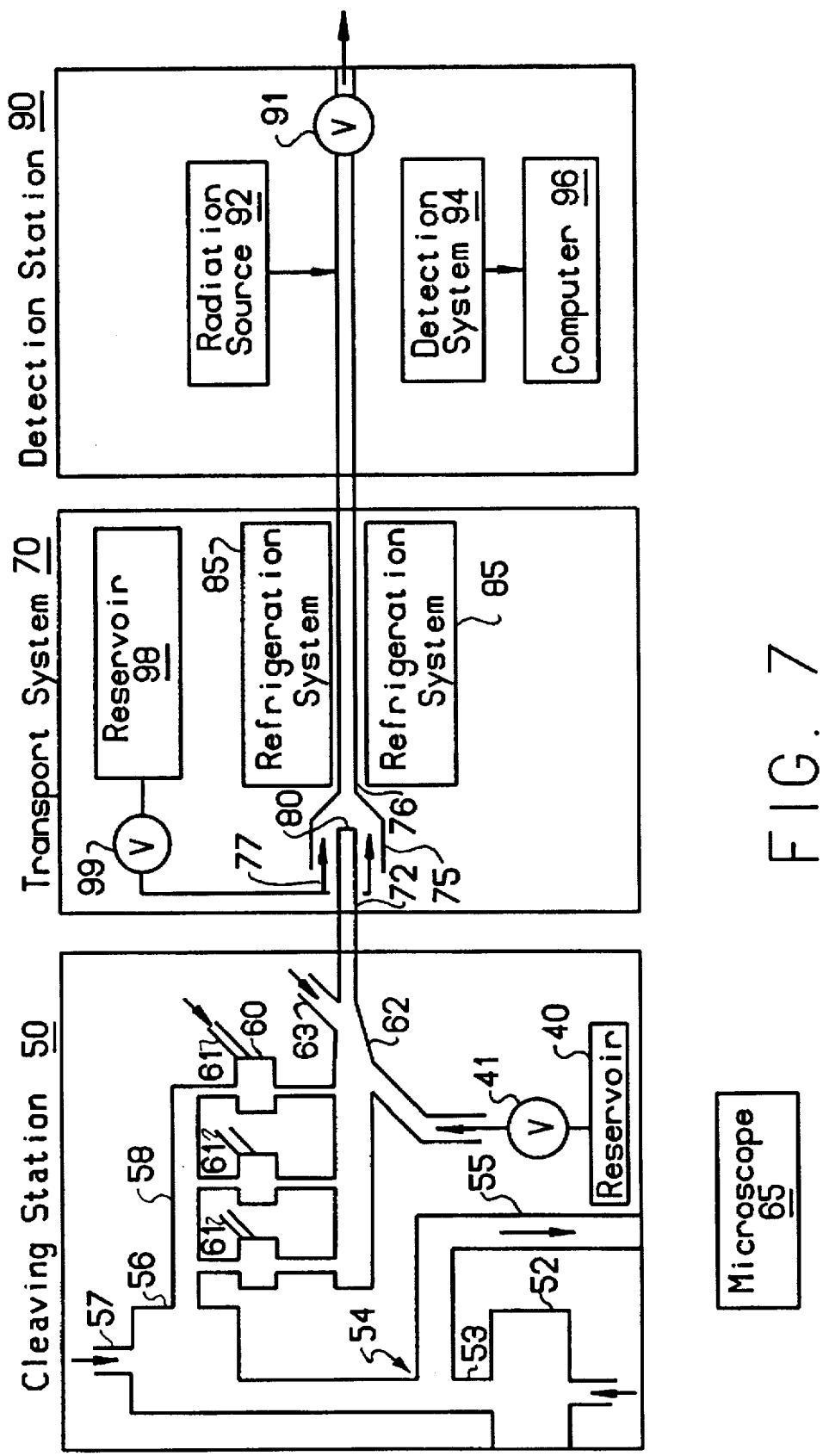
FIG. 7 is a block diagram of a preferred embodiment of the invention.

As shown in FIG. 7, apparatus for implementing this method preferably comprises a cleaving station 50, a transport system 70 and a detection station 90. The cleaving station illustratively comprises a sample chamber 52 for sorting and isolating cells, a culture chamber 56 and sample chambers 60 for sorting and isolating chromosomes. The cleaving station further comprises a progressively narrower channel 62 for immobilizing in a flowing aqueous solution the DNA strand that is to be sequenced and a microscope 65 for observing the preparation of cells, chromosomes and DNA molecules. The aqueous solution is supplied to channel 62 from a pressurized reservoir 40 and a metering valve 41, permitting independent adjustment of the flow rate of the aqueous solution. Further details of the cleaving station and its operation are discussed in Sections 5.1 through 5.2.4.

The cleaving station is fabricated from a variety of materials including, but not limited to, single crystal silicon, quartz, glass, metal, ceramic or plastic. The apparatus materials must be biocompatible with respect to the intended use. A further consideration is that materials or coatings for the channels are such that the DNA strand or the nucleotides do not adhere.

In a particular embodiment, the features of the micromachined body of the cleaving station are fashioned by a combination of lithographic techniques and selective etching. The lithographic methods include photolithography, electron beam lithography or direct ion beam or laser beam etching. Both isotropic and anisotropic etching are employable, and also microscopic abrasive etching. Electrodes are also fashioned in the base material by using standard semiconductor fabrication methods. Once the microchannel network is fabricated in the base material, an optically transparent cover material is hermetically sealed to the base by use of suitable adhesives (including UV-curable adhesives) or by silicon fusion or anodic bonding techniques in the case of silicon/glass bonding. In such an embodiment, the entire micromachined device is mounted on the stage of a microscope such that the cells, chromosomes and DNA molecules which are manipulated in the device are directly observed in real-time. A microscope such as the model MPM 800 Microscope Photometer from Carl Zeiss, Inc., Thornwood, N.Y., which employs quartz optics throughout is desirable. In one embodiment, the microscope uses low level epi-illumination to minimize photodamage to the sample materials, and therefore uses an intensified high sensitivity charged-coupled device (CCD) detector (e.g., Hamamatsu Photonics model C2400-87, Bridgewater, N.J.) with video display of the image.

Transport station 70 comprises a first microchannel 72 which is an extension of channel 62, a second surrounding microchannel 75, a nozzle 80 and a common exit microchannel 76. The first microchannel 72 guides the flowing aqueous solution to nozzle 80 from the point at which the nucleotides are cleaved from the DNA strand into the flowing solution. Nozzle 80 injects the nucleotide-bearing stream into the center of a coaxial sheath solution flowing in the same direction in a second surrounding microchannel 75. Preferably, the sheath solution is immiscible with the aqueous solution. Illustratively, the sheath solution is propane or propane mixed with ethane. The sheath solution is under sufficient pressure so as to be in the liquid state. All flows are laminar to prevent turbulence which would disrupt the sequential order of the nucleotides entrained in the aqueous sample stream. Careful attention is paid to the shape of all flow channels and to all transitions so as to maintain laminar flow throughout.

Advantageously, the aqueous solution exiting microchannel 72 is then hydrodynamically focused to a stream diameter of approximately one micron and the solutions are then rapidly chilled by a refrigeration system 85 to a temperature of about 170° to 85° K. thereby vitrifying the aqueous solution. The surrounding sheath solution remains liquid and non-viscous in this temperature range. As a result, the vitrified aqueous solution continues to be transported to the detection station 90 by the surrounding liquid sheath. Further details of the transport system and its operation are set forth in FIG. 8 below and are described in Section 5.3.

Detection station 90 comprises a source 92 of electromagnetic radiation, a detector system 94, and a computer 96. Source 92 is preferably, a high repetition rate pulsed laser such as a frequency-tripled, 76 MHz modelocked Ti:Sapphire laser. Detection system 94 is preferably a fast readout synchroscanned streak camera. Further details of the detection station are set forth, in FIGS. 9-11 below and are described in Section 5.4.

5.1. OBTAINING DNA FOR SEQUENCING

The DNA to be sequenced in the present invention can be obtained in purified form by any method known in the art. Any cell or virus can potentially serve as the nucleic acid source. The DNA may be obtained by standard procedures known in the art from cloned DNA, from amplified DNA, or directly from the desired cells or tissue samples (see, for example, Maniatis et al., 1982, Molecular Cloning, A Laboratory Manual, Cold Spring Harbor Laboratory, Cold Spring Harbor, New York, pp. 86–96 and 280–81, which is incorporated herein by reference). By way of example but not limitation, high molecular weight DNA can be isolated from eukaryotic cells by detergent lysis of cells followed by proteinase K digestion, phenol extraction, dialysis, density gradient centrifugation, and dialysis (see, e.g., id. at pp. 280–281). For the DNA thus obtained, the concentration of the DNA Should be determined (e.g., by $OD_{260}$ measurement), and the DNA should be appropriately diluted prior to introduction into the apparatus for sequencing so that only a single molecule (or no molecule, in which case introduction will be repeated) is introduced per each event.

If it is desired to amplify any of the isolated DNA or a specific portion thereof, prior to sequencing, polymerase chain reaction (PCR) can be employed (U.S. Pat. Nos. 4,683,202, 4,683,195 and 4,889,818; Gyllenstein et al., 1988, Proc. Natl. Acad. Sci. USA 85:7652–7656; Ochman et al., 1988, Genetics 120:621–623; Loh et al., 1989, Science 243:217–220, which are incorporated herein by reference).

In the processing of the DNA, care should be taken to avoid the introduction of nicks or breaks into the DNA molecule (e.g., by inadvertent exposure to endonucleases, undesirable shearing events, etc.). In addition, processing should be chosen so as to yield a DNA molecule compatible with the specific sequencing method employed according to the instant invention. For example, if a DNA molecule is to be immobilized (see Section 5.1.2, infra) by a method comprising linkage of the DNA molecule by reaction with its single-stranded 5' overhang, a single-stranded 3' overhang, or blunt-end, processing events can be chosen accordingly to produce such sites So they are available for reaction e.g., the DNA can be reacted with the appropriate enzyme (restriction enzyme, exonuclease, etc.) to produce such a reactive site. Furthermore, care should be taken to ensure the availability of the appropriate DNA terminus for binding with the exonuclease (see Section 5.2.1, infra) chosen for sequential liberation of nucleotides according to the instant invention.

In an alternative embodiment of the instant invention, an RNA molecule can be obtained and sequenced as provided herein. Procedures for isolation and purification of RNA are well known in the art (see e.g., Maniatis et al., supra, pp. 187–196). In such an embodiment, the exonuclease used for sequential liberation of nucleotides must have an RNA-dependent processive exonuclease activity. For purposes of convenience of description, the invention shall be described herein in terms of DNA but is to be construed as applicable to RNA, except where such is clearly or expressly made inapplicable.

In any of the specific embodiments of the invention wherein fluorescence is detected of sequentially cleaved nucleotide analogs and/or dye-tagged nucleotides, rather than that of solely standard nucleotides, the DNA is processed to incorporate such analogs and/or dye-tagged nucleotides prior to sequencing. This is accomplished, for example, by synthesizing a DNA copy of the DNA or RNA to be sequenced, using the appropriate DNA polymerase or reverse transcriptase, respectively, in the presence of the desired nucleotide analog(s) and/or dye-tagged nucleotide (s). Such nucleotide analogs, as used herein, are construed to mean analogs which are not labeled by covalent attachment of specific tags or dyes.

In one embodiment of the instant invention, DNA is isolated, purified, and processed manually prior to introduction into an apparatus for automated sequencing as described hereinafter. In an alternative embodiment, procedures for such isolation, purification and processing are automated. In this latter embodiment, for purposes of clarity but not limitation, the automated steps can be divided into those detailed in the subsections below. It should be understood that the specific procedures described in the subsections infra are exemplary, and are subject to modification in accordance with knowledge common in the art. In particular embodiments, all, none, or one or more of the steps described infra may be automated. For example, the sequencing apparatus may carry out an automated method commencing with the confinement and immobilization of DNA (see Section 5.1.2), or the microdissection of a chromosome, or chromosomal separation, or lysis of a single cell, or cell sorting, or cell culture, etc. Any of these procedures can also be performed manually, following procedures known to the skilled artisan.

5.1.1. OPTIONAL PROCEDURES FOR ISOLATION,

PURIFICATION AND PROCESSING OF DNA

Sources of Cells:

The DNA to be sequenced can be derived from any type of cell including bacterial cells, yeast cells, insect cells, plant cells or animal cells. Additionally, the DNA or RNA can be isolated from viruses. In a specific embodiment, the complete genome of an organism is sequenced according to the present invention. It is envisioned that the details of sample introduction and cell manipulation will vary from cell type to cell type, with the goal to provide a small sample of isolated single cells in suspension for further processing. In cases where the cells are already in suspension (e.g., blood or cells from suspension culture), further processing will likely be unnecessary. If the sample is a piece of solid tissue or contains aggregates of cells, preprocessing of the sample with enzymes (e.g., by slight trypsin digestion) and/or chemicals can be used to disrupt the intercellular matrix and release cells into suspension, which suspension can then be diluted to the appropriate cellular concentration.

In a preferred aspect, the cells are introduced into sample chamber 52 of FIG. 7 consisting of a small depression in a substrate at the edge of a transparent cover plate. The cells are typically suspended in a buffered physiological saline solution. The volume of the sample chamber is typically on the order of one microliter. Leading from the sample chamber under a transparent cover is a micromachined channel 53, the width of which is slightly larger than the typical diameter of the cells in the sample. Animal cells are typically 1–30 µ in diameter while plant cells are typically 10–100 µ in diameter.

The cells in the sample chamber can be viewed in real-time by the microscope system 65 which is outfitted with an infrared single-beam gradient optical trap (U.S. Pat. No. 4,893,886 by Ashkin and Dziedzic, which is incorporated herein by reference). Such a device permits the non-destructive selection, manipulation and transport of single cells and subcellular particles. As described in Buican et al., 1989, SPIE: New Technologies in Cytometry 1063:190–197 and Ashkin et al., 1987, Science 235:1517, which are incorporated herein by reference, a finely focused laser beam can exert sufficient radiation pressure upon a biological particle to suspend it against gravity and to move it laterally. To a good approximation, this can be explained by considering the particle as a transparent, spherical particle with an internal refractive index higher than the surrounding medium (see Bakker et al., 1991, Cytometry 12:479–485, which is incorporated herein by reference). Due to the change in the momentum of the incident photons at the point of refraction, a net radial force acts upon the particle in a direction toward the beam axis; thus, appearing to attract the particle toward the beam axis. Various alternative configurations that utilize counter-propagating laser beams may also be used to effectuate trapping. However, the net effect is to manipulate the particle by controlling the intensity and position of the laser beams that define the trapping region. Based on this approach, Buican et al. have demonstrated an instrument or micro-robot capable of analyzing, separating, and further processing selected biological particles.

In an alternative embodiment, the sample chamber can also incorporate an electrode (not shown), preferably provided with a micromachined guard screen to prevent direct contact of the cells with the electrode. Additional electrodes (not shown) incorporated further along the microchannels in the device allow for the application of an electric field to the sample fluid. Typical field strengths would be in the range of 1–10 volts/cm. Application of this field causes the cells to migrate single-file into the exit capillary channel 53.

Cell Sorting:

The target cell for sequencing is identified by visual inspection by a human operator using the microscope 65. Alternatively, real time computer image processing techniques similar to those used in high-resolution leukocyte analyzers (see Preston, K., Jr., 1987, Applied Optics 26:3258–3265, which is incorporated herein by reference) can be used to automate this step. The target cell is confined in the optical trap and translated along the exit channel 53 to the cell isolation chamber 56. Such techniques are already known in the art (Buican et al., 1987, Applied Optics 26:5311–5316, which is incorporated herein by reference).

In an alternative embodiment, a bifurcation 54 in the capillary channel allows for the sorting or selection of specific cells for sequencing. As a cell migrates toward the bifurcation under the influence of an applied electric field, it can be identified in the microscope. At the bifurcation, the cell is selectively diverted into one branch or the other of the capillary channel by applying an electric field along only the selected branch. This low speed fluidic sorting of single cells permits the direct isolation of one or more specific target cells for sequencing from the small initial sample. Such devices are known in the art (see e.g., U.S. Pat. No. 4,676,274 by J. F. Brown, which is incorporated herein by reference).

In yet another alternative embodiment, the cell sorting step can be eliminated by using a micropipette to select a single target cell and introducing it into the cell isolation chamber 56 directly.

Cell Culture Chamber:

Once the desired target cell has been isolated in chamber 56, an appropriate culture medium is introduced into the chamber through another microchannel 57 (see e.g., U.S. Pat. No. 4,676,274 by J. F. Brown, which is incorporated herein by reference). The culture medium is designed to cause the cell to undergo DNA replication, but to arrest the cell cycle in metaphase once the chromosomes have condensed. This is accomplished by standard methods (see e.g., Gasser and Laemmli, 1987, Exp. Cell Res. 173:85–98, which is incorporated herein by reference) that incorporate drugs such as colcemid into the culture medium. For example, in a specific embodiment, cells at a concentration of no more than 2 or $3\times10^5$/ml culture medium are exposed to demecolcine (0.06–0.15 µg/ml) (Colcemid, Sigma, St. Louis, Mo.) for 12–16 hours, in order to arrest them in metaphase. The process of metaphase arrest can be directly monitored with the microscope system 65.

Alternatively, cells can be cultured and arrested in bulk, and then either sorted within the instrument or micropipetted as above.

Cell Disruption:

Once the cell has been arrested in metaphase, the cell membrane is disrupted. A number of methods can be employed to effect membrane disruption including chemical and physical techniques or their combination. For example, solutions formulated to lyse the cell can be introduced through a microchannel. Such solutions can be hypoosmotic to cause swelling of the cell, and might include enzymes, detergents, solvents and other cofactors to promote gentle disruption of the cell membrane. These lysing solutions can also include various enzyme inhibitors (e.g., for nucleases or proteases, such as Trasylol (FBA Pharmaceuticals), phenylmethyl sulfonylfluoride, EDTA) to preserve the intact state of the chromosomes once the cells have been disrupted. For example, such a lysing solution can consist of 1% Triton X-100, 10% glycerol, 2% Trasylol (FBA Pharmaceuticals), and 20 mM EDTA in phosphate-buffered saline.

Physical means of cell disruption which can be used include but are not limited to a highly focused laser pulse which can be provided by using the microscope system 65 to focus the laser beam (see Tao et al., 1987, Proc. Natl. Acad. Sci. USA 84:4180–4184; Steubing et al., 1991, Cytometry 12:505–510, which are incorporated herein by reference). Another simple method which can be used is to incorporate a pair of electrodes in the culture chamber and to use a short, high voltage pulse (typically ~1 kV/cm and −1 msec duration) to disrupt the membrane as is done in the technique of electropermeabilization (see e.g., Zimmerman, 1986, Rev. Physiol. Biochem. Pharmacol. 105:175–256, which is incorporated herein by reference).

Separation of Chromosomes:

Once the cell has been disrupted and the chromosomes released, the chromosomes are separated into individual compartments. A microchannel 58 leading from the cell culture chamber has a cross section slightly larger than the diameter of a chromosome. Using the single-beam gradient optical trap, individual chromosomes are captured and transported via microchannel 58 to a chromosome isolation chamber 60. Such techniques are already known in the art (Buican et al., 1989, SPIE: New Technologies in Cytometry 1063:190–197, which is incorporated herein by reference).

In an alternative embodiment, an electric field is applied (~1–10 V/cm) via suitably incorporated electrodes (not shown), to induce the chromosomes to migrate into microchannel 58 single-file, much as is done in the initial step of cell sorting. The individual chromosomes are visualized by the microscope system as they proceed along the microchannel. This step can also be automated by using computer image analysis for the identification of chromosomes (see Zeidler, 1988, Nature 334:635, which is incorporated herein by reference). Bifurcations in the channel are similarly used in conjunction with selectively applied electric fields to divert the individual chromosomes into small isolation chambers 60. Once individual chromosomes have been isolated, the sister chromatids are separated by either a focused laser microbeam and optical tweezers, or mechanical microdissection to provide two "identical" copies for sequencing.

Alternatively, chromosomes are prepared in bulk, and then either sorted within the instrument or micropipetted into individual chambers.

Chromosome Fragmentation:

If desired, the DNA in the individual chromosomes (especially the larger ones) can be fragmented to allow for parallel sequencing of individual chromosome fragments or to sequence a smaller portion of the DNA or merely to simplify the handling of large DNA molecules. Such fragmentation is accomplished by methods known in the art, e.g. by restriction endonuclease digestion or cleavage by sequence-specific reagents or, in preferred aspects, by laser microbeam irradiation (see, e.g., Monajembashi et al., 1986, Exp. Cell Res. 167:262–265, which is incorporated herein by reference) or mechanical microdissection (see, e.g., Ludecke et al., 1989, Nature 338:348–350, which is incorporated herein by reference).

MicrodisSected fragments from individual chromosomes can then be separated into individual chambers 60 using a single-beam gradient optical trap, as has been demonstrated by those skilled in the art (Seeger et al., 1991, Cytometry 12:497–504, which is incorporated herein by reference).

Chromosome Unfolding:

After each chromosome or chromosome fragment has been isolated in a separate chamber 60 of the device, the chromatin structure is then unfolded by removing the chromosomal proteins. This is accomplished by methods known in the art. For example, solutions containing (2 mg/ml) dextran sulfate (or 2 M NaCl) and (0.2 mg/ml) heparin have been shown to selectively remove the histones, leaving extended loops of DNA attached to the nuclear scaffold (see Paulson and Laemmli, 1977, Cell 12:817–828; Adolph et al., 1977, Cell 12:805–816, which are incorporated herein by reference). The nuclear scaffold is then disrupted to release the chromosomal DNA molecule, e.g., by exposure to thiol reagents or by chelating copper ions from the metalloprotein which stabilizes the scaffold (see, Lewis and Laemmli, 1982, Cell 29:171–181, which is incorporated herein by reference). For example, the thiol reagents β-mercaptoethanol (1 mM–140 mM), dithiothreitol, OP (3 mM), or neocuproine (3 mM) can be used to dissociate histone-depleted chromosomes (id.). High salt concentrations (e.g., 1 M NaCl) can also be used to disrupt the folded chromosome structure (see, Yanagida et al., 1986, in Applications of Fluorescence in the Biomedical Sciences, Taylor, L. et al. (eds.), Alan R. Liss, Inc., New York, pp. 321–345, which is incorporated herein by reference). Illustratively, such solutions are introduced into chambers 60 via microchannels 61.

In order to avoid mechanical breakage of the DNA during protein extraction and subsequent manipulation, especially for very high molecular weight DNA, the DNA can be condensed into compact aggregates known as ψ (psi) DNA by incubation with threshold concentrations of polymers such as polyethylene glycol (Laemmli, 1975, Proc. Natl. Acad. Sci. USA 72:4288–4292, which is incorporated herein by reference). Dilution of the polymer below the critical concentration restores the extended DNA strand for subsequent sequencing.

The process of chromosomal unfolding is monitored by the microscope system 65 (see, e.g., Hiraoka et al., 1987, Science 238:36–41; Yanagida et al., 1986, in Applications of Fluorescence in the Biomedical Sciences, Taylor, D. L., et al. (eds.), Alan R. Liss, Inc., New York, pp. 321–345; Richards, 1989, Nature 338:461–462; Smith et al., 1989, Science 243:203–206; Schwartz et al., 1989, Nature 338:520–522; Morikawa et al., 1981, J. Biochem. 89:693–696; Matsumoto et al., 1981, J. Mol. Biol. 152:501–516; Yanagida et al., 1983, C.S.H. Symp. Quant. Biol. 47:177–187; Hirschfeld, 1976, Applied Optics 15:2965–2966). In one specific embodiment, this is accomplished by use of a fluorescent dye that is noncovalently (e.g., by intercalation, 1992 Glazer and Rye, Nature 359:859–861, which is incorporated herein by reference) bound to the DNA. Care, however, must be taken to ensure that the absorption spectrum of the fluorescent dye does not overlap with either the absorption or emission spectra of the native nucleotides which would thus interfere with nucleotide identification during sequencing. Furthermore, the dye used must be bound in such a way so as not to interfere with or prevent the processive exonuclease reaction during sequencing (see Section 7.2, infra). Alternatively, the fluorescent dye is removed from the DNA prior to sequencing by passing an appropriate solvent or competitive binding agent over the DNA once positioned.

5.1.2. IMMOBILIZATION AND MANIPULATION OF DNA

In a preferred embodiment, to facilitate separation of the DNA substrate from the exonucleolytically released nucleotides, the DNA is confined in an extended conformation in a progressively narrower capillary channel 62 and the terminus of the DNA distal from the exonuclease binding site is immobilized. This is carried out by various methods known in the art. However, whatever the specific method used, care must be taken to leave available the appropriate binding site for exonuclease binding (depending on the specificity of the exonuclease) and to ensure that the method does not interfere with exonuclease digestion or disrupt the sequential order of the released nucleotides.

For example, in a preferred embodiment, a strand of DNA 66 is immobilized by linkage to a microsphere 68 which is manipulated by a single-beam gradient optical trap 69 shown in FIG. 8 (see U.S. Pat. No. 5,079,169 by Chu and Kron, which is incorporated herein by reference). Numerous methods exist in the art for attaching the DNA to a microscopic bead. Covalent chemical attachment of the DNA to the Dead can be accomplished by using standard coupling agents, such as water-soluble carbodiimide, to link the 5'-phosphate on the DNA to amine-coated microspheres through a phosphoamidate bond. Another alternative is to first couple specific oligonucleotide linkers to the bead using similar chemistry, and to then use DNA ligase to link the DNA to the linker on the bead. Oligonucleotide linkers can be employed which specifically hybridize to unique sequences at the end of the DNA fragment, such as the overlapping end from a restriction enzyme site or the "sticky ends" of bacteriophage lambda based cloning vectors, but blunt-end ligations can also be used beneficially. Homopolymer linkers may also find utility in certain applications. By employing oligod-dT coupled to the bead, it will be possible to hybridize to the poly-A tail found in mRNA as a means for directly sequencing mRNA isolated from cells (supra). Yet another method for coupling DNA to beads would employ specific ligands attached to the end of the DNA to link to ligand-binding molecules attached to the bead. For example, a terminal transferase can be used to incorporate such a ligand onto the end of the DNA, oligonucleotide linkers already containing an appropriate ligand can be ligated to the DNA, or oligonucleotides capable of forming a stable triple-helix with a target duplex DNA can be synthesized to incorporate an appropriate ligand. Possible ligand-binding partner pairs include but are not limited to biotin-avidin/streptavidin, or various antibody/antigen pairs such as digoxygenin-anti digoxygenin antibody (1992 Smith et al., "Direct Mechanical Measurements of the Elasticity of Single DNA Molecules by Using Magnetic Beads," Science 258:1122–1126, which is incorporated herein by reference). In one particular embodiment in which the DNA contains the appropriate single-stranded telomeric recognition site, telomere terminal transferase (Greider et al., 1987, Cell 51:887–898, which is incorporated herein by reference) can be used to incorporate a biotinylated nucleotide at the 3' end of the DNA which can then be bound to avidin immobilized on the bead. (In this embodiment, a 5' to 3' exonuclease would then be used for sequencing, since the 3' end would be the "tethered" end.) In another embodiment, calf thymus terminal transferase (Kato et al., 1967, J. Biol. Chem. 242:2780, which is incorporated herein by reference) can be used to incorporate a ligand-linked nucleotide onto the 3' end of any DNA molecule with a free 3' hydroxyl group. In still another approach, a DNA-binding protein can be coupled to the bead by chemistries well known in the art and in such a fashion that the DNA-binding site is unperturbed. DNA containing the recognition sequence for the DNA-binding protein can thereby be coupled to the bead.

As an alternative to coupling to preexisting microscopic beads, bead-like structures, herein referred to as "optical handles," can be chemically synthesized at the end of a DNA molecule in order to provide a particle with dimensions and refractive properties appropriate for manipulation by an optical trap. Such particles can be as small as 10 nm and will have a refractive index as high as possible, but at least greater than the surrounding solvent. It will be recognized by those skilled in the art that the ability to target the synthesis of an optical handle to a specific nucleotide sequence provides a means for identifying and purifying a unique DNA fragment for sequencing from a complex mixture. For example, the total genomic DNA from a single cell can be prepared as described supra while under observation by the microscope system 65. An optical handle is then synthesized in situ at a unique DNA sequence, such as a single copy gene, by methods described infra. Alternatively, an optical handle can be synthesized at the site of a repetitive element in the DNA (e.g., an ALU sequence) which will provide predictable sites distributed throughout the genome. Upon completion of the synthesis of the optical handle, the handle will become visible in the microscope 65, and the unique fragment with the attached handle can be isolated from the remaining DNA by means of the single beam gradient optical trap 69 for subsequent sequencing. Such a process is extremely difficult to accomplish using pre-formed beads and linking technology, due to the very low diffusivity of both the bead and the high molecular weight DNA, and therefore the very low probability of successfully coupling a bead to the unique target. Synthesis of such particle-like structures at the end of a DNA molecule can be accomplished by methods known in the art, including the sequential addition of branched oligonucleotides (Urdea et al., WO 90/13667 which is incorporated herein by reference) or by modification of the techniques for the synthesis of starburst dendrimers (Tomalia and Wilson, EP 247629 A2, which is incorporated herein by reference).

In general, the first step in the synthesis of an "optical handle" at a specific target sequence requires the binding of a bifunctional binding agent to the target sequence. The first functionality of the binding agent is to provide a means for uniquely recognizing and binding to the target DNA sequence. Target sequence recognition can be accomplished by means such as hybridization of a region of single-stranded DNA to a complementary oligonucleotide, hybridization of a duplex region of DNA with an oligonucleotide capable of forming a triple helix with the target sequence, complexing with a DNA binding protein which specifically recognizes and binds to the target sequence, or other means known in the art. Further means for covalently linking the DNA binding oligonucleotide or protein to its target sequence can then be employed as an additional step to prevent dissociation of the target sequence. Such methods might include photochemical crosslinking (1987 LeDoan et al., Nucleic Acids Res. 15:7749–7760, which is incorporated herein by reference). The second functionality of the binding agent is to provide a means for binding or linkage to initiate the first cycle of growth of the optical handle. Such functionality, for example, can be provided by a biotin group attached to the DNA recognition and binding functionality in such a fashion as to be capable of binding to streptavidin. Adding streptavidin to the bifunctional binding agent already complexed with its target DNA sequence then results in a unique ternary complex composed of one molecule each of target DNA, bifunctional linker-biotin, and streptavidin. Streptavidin contains four binding sites for biotin with two each on opposite sides of the streptavidin protein molecule (1989 Weber et al., Science 243:85–88; 1989 Hendrickson et al., Proc. Natl. Acad. Sci. USA 86:2190–2194, which are incorporated herein by reference). Only one of these sites will be occupied by binding to the biotin group of the bifunctional linker, leaving the three other sites available for binding.

The next step in the growth of the optical handle is to introduce a second linker comprised of two biotin molecules joined by a spacer (1989 Ahlers et al., Thin Solid Films 180:93–99, which is incorporated herein by reference). The spacer couples the two biotin groups in such a manner that each biotin is fully capable of binding to streptavidin, but the length and rigidity of the spacer is selected so that both biotin groups cannot bind to the same streptavidin molecule. Addition of biotin-spacerbiotin to the complex will result in the binding of one, two or three such molecules to the previously unoccupied sites in the single streptavidin molecule, providing one, two or three exposed biotin groups for subsequent binding to additional streptavidin molecules. By alternating the addition of streptavidin and biotin-spacer-biotin with washing steps in between to remove any unbound reagents, the optical handle is synthesized as an exponentially growing complex of cross-linked streptavidin molecules. A sufficient number of cycles is carried out to provide an optical handle of sufficient size and optical properties for manipulation by optical tweezers. The properties of streptavidin can be modified using genetic engineering techniques in order to improve its properties for the formation of such optical handles (1990 Sano and Cantor, Proc. Natl. Acad. Sci. USA 87:142–146; 1991 Sano and Cantor, Bio/Technology 9:1378–1381, which are incorporated herein by reference). It will also be apparent to those skilled in the art that many other chemistries can be employed to achieve similar results.

It will also be recognized by those skilled in the art that methods similar to those described supra for the synthesis of "optical handles" can be adapted for the in situ synthesis of "magnetic handles" to produce microscopic magnetic particles attached to the end of a specific target DNA molecule for manipulation by magnetic rather than optical forces (1992 Smith et al., Science 258:1122–1126, which is incorporated herein by reference).

For the sequencing of an initially double-stranded DNA molecule, several approaches are possible. In one method shown in FIG. 14, single beads 401, 402 are coupled or synthesized on both ends of the duplex molecule, one per single strand 411, 412. Two independent optical traps 421, 422 are then used to capture the beads, one per trap. The chemical conditions in the microchamber can then be adjusted to denature the duplex by methods well known in the art, and the individual single strands can be separated by manipulation of the optical traps and transported into separate microchambers for subsequent independent sequencing. Alternatively, the duplex DNA molecule can be extended to its full contour length by separation of the optical traps and positioned orthogonal to the flow axis of the microchannel 62. A double-strand specific exonuclease which recognizes the unlinked free end of the duplex DNA is then used to cleave nucleotides from one strand of the duplex. The orthogonal flow or the application of an electric field will transport the single nucleotides away from the DNA without interference from the growing single-stranded region on the opposite strand. Upon completion of the digestion of the first strand, an appropriate single-strand specific exonuclease can be employed to cleave the individual nucleotides from the remaining single strand which is now extended from the bead colinear with the flow axis in the microchannel either by bulk liquid flow or by the application of an electric field.

Multiple-beam gradient optical traps can be similarly employed for the manipulation and positioning of microspheres with DNA attached as described supra.

In yet another specific embodiment, the DNA molecule is immobilized by linkage using any of the methods described supra to a microscopic mechanical support such as a glass microneedle which can be positioned in the flow stream. Kishino and Yanagida (1988, Nature 334:74–76, which is incorporated herein by reference) have demonstrated similar methods for the attachment of single actin filaments to glass microneedles. Another specific variation on this approach is to attach the DNA by any of the methods described supra directly to the wall of the microchannel 62.

Yet another means for immobilizing the DNA molecule for sequencing would be to confine it to a microchannel which has a small enough cross section to retard the mobility of the DNA under the influence of flow or an electric field, without appreciably reducing the mobility of a single, released nucleotide (i.e., comparable to adjusting the effective pore size in a gel matrix). As the chromosome is progressively unfolded, an applied electric field is used both to separate the extracted proteins from the DNA, and to extend and confine the DNA molecule in a progressively narrower capillary channel 62 (see Holzwarth et al., 1987, Nucl. Acids Res. 15:10031–10044; Richards, 1989, Nature 338:461–462; Smith et al., 1989, Science 243:203–206; Schwartz et al., 1989, Nature 338:520–522; Bustamante, 1991, Annu. Rev. Biophys. Biophys. Chem. 20:415–446, which are incorporated herein by reference). The walls of the microchannel will be made of appropriate materials or chemically modified to eliminate both electroendosmosis and nucleotide adsorption by methods known in the art, such as coating with a monolayer of non-cross-linked polyacrylamide (Hjertén, 1985, J. Chromatog. 347:191–198, which is incorporated herein by reference).

The purpose of this stage of the process is to fully extend the linear chromosomal DNA molecule and to confine it physically to a narrow microchannel to prevent the DNA from becoming "tangled". At this point the single isolated DNA molecule from the chromosome is ready for sequencing.

5.2. EXONUCLEASE DIGESTION

Exonuclease digestion of the isolated single DNA molecule is then carried out by use of a DNA-specific exonuclease (dexyribonuclease) to generate from the DNA single nucleotides in sequential order. These nucleotides are then identified as described infra.

5.2.1. PROCESSIVE EXONUCLEASES FOR USE IN THE INVENTION

Once the DNA molecule has been fully extended and confined in a narrow capillary channel, a highly processive exonuclease is introduced, preferably through a side channel 63 near one end of the DNA molecule. Such an exonuclease preferably exhibits the following properties:

The enzyme is strictly exonucleolytic, with no endonucleolytic activity.

The enzyme is highly processire (i.e., once a single exonuclease molecule has bound to the terminus of a single DNA molecule, it can completely hydrolyze that strand without dissociating from the DNA).

The enzyme removes only mononucleotides, not dinucleotides or oligonucleotides.

The enzyme has a high turnover number to maximize the sequencing rate.

The enzyme is highly stable to facilitate handling, improve processivity and allow digestion at elevated temperatures to increase the turnover number.

The rate of phosphodiester bond cleavage by the enzyme is independent of which nucleotide is being removed or the sequence adjacent to that nucleotide. This results in more uniform generation of nucleotides for detection.

The enzyme does not require nucleotide cofactors or an energy source.

The activity of the enzyme is controllable by a simple ion cofactor such as $Mg^{++}$ to allow for controlled initiation of hydrolysis.

In addition, the enzyme chosen must have a specificity (e.g., 5' to 3' or 3' to 5', singlestranded or double-stranded) that is compatible with the DNA substrate being sequenced.

Processive exonucleases suitable for use in the present invention include but are not limited to the following:

Exonuclease I from *E. coli* (Brody et al., 1986, J. Biol. Chem. 261:7136–7143), which is a 3' to 5' singlestranded DNA exonuclease.

Lambda (λ) exonuclease (Little, 1967, J. Biol. Chem. 242:679–686; Carter et al., 1971, J. Biol. Chem. 246:2502–2512; Little, 1981, in Gene Amplification and Analysis, Vol. 2., Chirikjian and Papas (eds.), Elsevier/North-Holland, New York, pp. 135—145), which is a 5' to 3' double-stranded DNA exonuclease.

Exonuclease VIII from *E. coli* (Joseph and Kolodner, 1983, J. Biol. Chem. 258:10418–10424, which is incorporated herein by reference), which is a 5' to 3' double-stranded DNA exonuctease.

In addition to any other processive exonucleases identified in the art, processive exonucleases for use in the present invention can be obtained by genetic engineering so as to modify known exonucleases to optimize desirable properties.

The level of processivity of an enzyme needed for use in the present invention will depend on the size of the DNA desired to be sequenced, but generally, the greater the processivity, the more preferred is the enzyme, all other properties being equal. For example, if a DNA molecule is 100 nucleotides in size, the exonuclease need only have a processivity of 100 bases (i.e., not dissociate until 100 bases have been hydrolyzed). However, since the method and apparatus of the present invention are generally more efficient the longer the DNA strand being sequenced, an exonuclease of much greater processivity (e.g., one which remains bound for at least thousands of bases) is preferred. Any method known in the art (see, e.g., Thomas and Olivera, 1978, J. Biol. Chem. 253(2):424–429; Das and Fujimara, 1980, Nucl. Acids Res. 8:657–671; Becerra and Wilson, 1984, Biochem. 23:908–914; Joannes et al., 1985, Biochem. 24:8043–8049, which are incorporated herein by reference) can be used to determine whether an exonuclease is processive or not processive (i.e., distributive) or to determine the degree of processing.

Suitable reaction conditions for exonuclease digestion are known in the art. For example, suitable reaction conditions for Exonuclease I are as follows (Brody et al., 1986, J. Biol. Chem 261:7136, which is incorporated herein by reference): 67 mM Tris buffer (pH 8.5 at room temperature), 6.7 mM $MgCl_2$, 10 mM 2-mercaptoethanol, at 37° C. Suitable reactions conditions for λ exonuclease are as follows (Thomas and Olivera, 1978, J. Biol. Chem. 253:424–429, which is incorporated herein by reference): 67 mM glycine/KOH (pH 9.6), 3 mM $MgCl_2$, at 37° C. Suitable reaction conditions for Exonuclease VIII are as follows (Joseph and Kolodner, 1983, J. Biol. Chem. 258:10411–10417, which is incorporated herein by reference): 20 mM Tris-HCl(pH 8.0), 10 mM MgCl2, 10 mM 2-mercaptoethanol, at 37° C.

The reaction conditions employed to carry out exonuclease digestion in the method of the present invention can vary widely from those set forth above, in accordance with knowledge common in the art.

In an embodiment of the.invention in which the sample of DNA is known to contain or may contain modified bases such as methylated bases (e.g. 5-methylcytosine), the processire exonuclease chosen for use should not be inhibited in its activity by such modified bases.

In yet other embodiments of the invention in which fluorescent nucleotide analogs or dye-tagged nucleotides are incorporated into the DNA molecule to be sequenced, the processire exonuclease chosen for use should not be inhibited in its activity by such modified bases, including possible combinations of native nucleotides, fluorescent nucleotide analogs and dye-tagged nucleotides in the same DNA molecule.

While highly processire exonucleases are preferred for use in the present invention, distributive exonucleases can also be utilized with less efficiency. In the worst case, without enzyme recycling, one molecule of exonuclease will be consumed for each nucleotide sequenced, adding significantly to the cost of sequencing. The speed of sequencing will also be reduced because of the time required for each successive exonuclease binding event. In addition, the dissociated exonuclease must either be removed from the flow stream without disturbing the sequential order of those single nucleotides already released, or have optical properties (e.g., absorption, fluorescence, etc.) such that the presence of nuclease molecules does not interfere with the detection and discrimination of individual nucleotides.

In an aspect of the invention involving the sequencing of RNA, a processive exoribonuclease is employed (McLaren et al., 1991 J. Mol. Biol. 221:81–95, which is incorporated herein by reference). Processive exoribonucleases suitable for use in the present invention include but are not limited to the following:

Polynucleotide phosphorylase from Micrococcus lysodeikticus (Klee and Singer, 1968, J. Biol. Chem. 243:923–927, which is incorporated herein by reference) which is a 3'–5' exoribonuclease.

Ribonuclease II from *E. coli* (Nossal and Singer, 1968, J. Biol. Chem. 243:913–922, which is incorporated herein by reference) which is also a 3'–5' exoribonuclease.

Suitable reaction conditions for exonuclease digestion are known in the art. For example, suitable reaction conditions for polynucleotide phosphorylase are as follows (McLaren et al., 1991, J. Mol. Biol. 221:81–95, which is incorporated herein, by reference): 50 mMTris-HCl (pH 7.4), 10 mM $K_2HPO_4$, 7 mM $MgCl_2$ at 37° C. Suitable reaction conditions for ribonuclease II are as follows ((McLaren et al., 1991, J. Mol. Biol. 221:81–95, which is incorporated herein by reference): 20 mM Tris-HCl (pH 7.9), 100 mM KCl, 4 mM $MgCl_2$, 100 µM dithiothreitol (prepared in situ) at 37° C.

In a preferred aspect of the invention, after confinement and immobilization of the substrate DNA, the following steps are carried out in the stated order: appropriate reaction components, with the exception of a required cofactor, are introduced to achieve the desired reaction conditions; exonuclease is introduced and allowed to bind to the DNA; excess unbound enzyme is then removed; and the required cofactor is then introduced to initiate digestion. These steps are described more fully infra.

Temperature and pH of the reaction can be varied in order to optimize the reaction rate for sequencing efficiency. In order to slow the rate of nucleotide cleavage in certain applications, the temperature at nozzle 80 may be as low as 0° C., or just above the freezing point of sample solution 71. In yet other applications where the highest possible rate of nucleotide cleavage is.desired or when thermostable exonuclease is employed, the temperature at nozzle 80 may be as high as 100° C., or just below the boiling point of sample solution 71. A suitable temperature control element 73 (FIG. 8) is used to achieve the appropriate temperature.

5.2.2. BINDING OF ENZYME

After confinement and immobilization of DNA as discussed supra, a suitable amount of exonuclease is introduced, e.g. via a capillary channel, and allowed to bind to the substrate DNA by incubation for an appropriate time period. For example, such incubation can be carried out for one minute at 37° C., or such other time and temperature as may readily be determined by one skilled in the art. In a preferred embodiment, excess unbound enzyme is then removed so as to minimize interference of residual unbound enzyme with the flow and detection of the sequentially released nucleotides. In a preferred aspect, the excess enzyme is removed by flowing buffer solution over the immobilized DNA-exonuclease complex, or in another embodiment, electrophoretically removing the excess unbound exonuclease, by applying an electric field across the reaction chamber containing the immobilized DNA-exonuclease complex.

In an alternative embodiment, a single exonuclease molecule can be bound to the DNA under appropriate conditions prior to introduction of such a stable DNA-exonuclease complex into microchannel 72.

5.2.3. COFACTOR "TRIGGERING" OF REACTION

In a preferred aspect of the invention, exonuclease digestion commences after removal of residual enzyme by introduction of a required enzyme cofactor into the reaction sample. Such a cofactor is preferably a divalent cation such as magnesium. Thus, for example, an amount of $MgCl_2$ necessary for exonuclease activity is withheld during the binding of enzyme and removal of excess enzyme (e.g., by chelation with EDTA), but is then introduced in order to start exonuclease digestion and resultant sequential release of nucleotides.

It will also be recognized by those skilled in the art that exonucleases whose catalytic activity cannot be completely regulated as described supra can also be utilized in the present invention. In such cases, the exonuclease is bound to the DNA under conditions of minimal catalytic activity (e.g. low temperature or non-optimal pH) and the resulting DNA-exonuclease complex is prepared and positioned for sequencing as rapidly as possible so as to minimize the number of nucleotides which are cleaved during these steps. Once positioned, the DNA-exonuclease complex is then exposed to optimal conditions for exonuclease activity by increasing the temperature using heater 73 or by altering chemical conditions of the sample stream 71.

5.2.4. RESTARTING EXONUCLEASE DIGESTION

In a preferred aspect, care is taken during the processing of DNA prior to exonuclease digestion so as to avoid defects in the DNA such as breaks, nicks, apurinic or apyrimidinic sites, or chemical modifications that may interfere with enzyme activity and/or the uniform sequential release of nucleotides. However, since such defects can sometimes be unavoidable, in the event that nucleotide release halts prematurely, either due to the presence of such a defect or due to dissociation of the enzyme or loss of activity, exonuclease digestion can be restarted by carrying out the following steps: a washing/removal step (to remove interfering impurities, the cofactor "trigger", etc.) (which can be accomplished, e.g. electrophoretically), introduction of reaction components (i.e., the appropriate buffer, reducing agent) minus cofactor, introduction and binding to the DNA of a fresh sample of exonuclease, removal of excess unbound enzyme, and re-introduction of the necessary cofactor (e.g., $MgCl_2$). The exonuclease reaction should then commence, but if the DNA defect is such as to prevent such "restarting", sequencing should be attempted on a fresh molecule of substrate DNA.

5.3. TRANSPORT SYSTEM & MATRIX ENTRAINMENT

In general, there are two distinct classes of transport system which can be used with the present invention. The preferred embodiment is a transport system which provides a continuous transport of single nucleotides for detection by the detection station 90. A second class of transport system allows for the discontinuous transport and detection of single nucleotides. In both classes of transport system, means are provided for incorporating the single transported nucleotides in a fluorescence-enhancing matrix.

5.3.1. CONTINUOUS TRANSPORT & DETECTION

FIG. 8 depicts in schematic form an enlarged cross-section of a preferred embodiment of the continuous transport system 70 of the present invention. As indicated previously, the transport system comprises first microchannel 72, second microchannel 76 and nozzle 80. A single molecule of DNA 66 is attached to a microscopic bead 68 which is held in a single-beam gradient optical trap 69 and positioned along the central axis of microchannel 62 in such a manner that.the other end of the DNA molecule with a single bound molecule of exonuclease 67 is positioned at the mouth of microchannel 72 at the nozzle 80 as indicated. Nucleotides 64 are cleaved from DNA strand 66 at the nozzle 80 in microchannel 72; and the nucleotides are detected by detection station 90.

Within the first microchannel 72, each nucleotide is processively removed from the DNA molecule and is separated from the DNA. Separation is conveniently and advantageously accomplished by reliance on laminar flow of aqueous solution 71 in microchannel 72. In an alternative embodiment, separation can be achieved by the application of an electric field along the first microchannel 72. The position of the site of exonuclease action can be maintained constant with respect to the nozzle 80 by moving the optically-trapped bead 68 toward the nozzle at a rate equal to the rate of decrease in the length of the extended DNA molecule 66 due to exonuclease action.

After exiting the nozzle 80 of first microchannel 72, the flowing aqueous solution 71 carrying the nucleotides is introduced along the central axis of a laminar sheath fluid 77 flowing in the same direction. The sheath fluid is immiscible with the aqueous solution and provides a barrier between the aqueous solution and the walls of the second microchannel 76 to prevent absorption or adsorption of the entrained nucleotides 64. The desirable properties for a sheath fluid for use in the present invention are as follows:

Non-polar;

Immiscible and chemically inert with the aqueous, nucleotide-containing sample stream, including any polymer-forming, fluorescence-enhancing, or stability-enhancing agents as described infra;

Optically transparent and non-fluorescent in the ultraviolet (~240–300 nm) and near ultraviolet (~300–450) regions where nucleotides absorb and fluoresce respectively;

Pure with respect to contaminants which might degrade or interfere with the fluorescence of the nucleotides;

Liquid and non-viscous at the point of introduction of the nucleotide-containing sample stream under only slight or moderate pressure;

For those embodiments involving cooling of the nucleotides, the sheath must remain liquid and non-viscous at the low temperature at which fluorescence is detected; and Ideally, the composition of the sheath is selected so as to match the refractive index of the sample stream in order to avoid scattering at their interface.

Typical compounds useful as the sheath fluid are propane (B. P. −44.5° C., M. P. −189.9° C.), a mixture of propane and ethane (B. P. −88.6° C., M. P. −182.8° C.), or other similar hydrocarbons. Ultrapure propane for use in the present invention can be obtained in 99.99% purity from Specialty Products & Equipment, Houston, Tex. Residual impurities are principally n-butane/isobutane (<30 ppm), methane (<20 ppm) and propylene (<10 ppm). Such sheath fluids are inserted into the microchannel 76 at port 78 under sufficient pressure to be in the liquid state. For example, pure propane is liquid at approximately 10 atmospheres (~130 PSIG) at room temperature. As schematically illustrated in FIG. 7, sheath fluid 77 is provided from a pressurized reservoir 98 by means of a metering valve 99 which is used to adjust the rate of flow of sheath fluid 77 into inlet port 78 of microchannel 75. Advantageously, throughout this system the pressure and temperature of the sheath solution are maintained in the range where the sheath solution is a liquid.

Illustratively, the microchannels are cylindrical in cross section and formed in a suitable substrate. Other cross sections are permissible, so long as all flows are laminar. Methods for fabricating such microchannels and nozzles are known to those skilled in the art, including but not limited to the methods of Ohki et al. (U.S. Pat. No. 4,983,038), and Little (1984, Rev. Sci. Instrum. 55:661–680, which are incorporated herein by reference).

The stream of sheath fluid 77 is inserted into microchannel 76 at port 78 at a constant laminar flow rate. Cleaved nucleotides 64 are entrained in the aqueous solution 71 at the point of exonuclease 67 and inserted by nozzle 80 at a constant laminar flow rate along the central axis of the stream of sheath fluid in such a manner that the combined flow 82 is also laminar. The combined laminar flow 82 is regulatedby a third metering valve 91 at the downstream end of the detection station 90.

In the preferred embodiment shown in FIGS. 7 and 8 the flow rate of the sheath fluid is greater than the flow rate of the aqueous solution. As a result, hydrodynamic pressure reduces the stream of aqueous solution from a cross-section 84 to a cross-section 85. This phenomenon is conventionally called hydrodynamic focusing. Since the aqueous solution is essentially incompressible, the effect of the hydrodynamic pressure is to increase the flow rate of the aqueous solution until it matches that of the sheath fluid (see, for example, F. Zarrin et al., 1985, Anal. Chem. 57:2690–2692; Howard M. Shapiro, 1988, Practical Flow Cytometry, Alan R. Liss, Inc., Chap. 4; Van Dilla et al. (eds.), 1985, Flow Cytometry: Instrumentation and Data Analysis, Chap. 3, Academic Press, which are incorporated herein by reference). Illustratively, hydrodynamic focusing achieves a 10-to-1 reduction in diameter of the aqueous solution with a 100-to-1 increase in the speed of flow of the aqueous solution relative to the sheath fluid (see, for example, H. B. Steen, 1990, "Characteristics and Flow Cytometers," in Flow Cytometry and Sorting, M. R. Melamed et al. (eds.), pp. 11–25, which is incorporated herein by reference). With reference to FIG. 8, hydrodynamic focusing takes place in the region between lines 86 and 87. Downstream of line 87 the flow rates of the aqueous solution and the sheath solution are the same.

In the embodiment where the cleaved nucleotides are separated from the DNA by application of an electric field (supra), the interaction of the sheath flow 77 with the aqueous nucleotide-containing flow is as described by Cheng et al. (1990, Anal. Chem. 62:496–503, which is incorporated herein by reference).

5.3.2 FLUORESCENCE ENHANCING MATRIX

After the aqueous solution 71 is focused and before the point at which nucleotide detection occurs, it is solidified into a solid, fluorescence-enhancing matrix 88 by, for example, vitrification, polymerization or polymerization and cooling. In addition, the nucleotides may also be oriented in the stream to enhance detection of their fluorescence (infra). As will be apparent, orientation must be accomplished before the aqueous solution solidifies. Typically an electrostatic field is used to orient the nucleotides. Illustrative apparatus for applying such an electric field comprises an array of electrodes 89 surrounding the microchannel in the region where hydrodynamic focusing occurs.

Illustrative apparatus for solidifying the aqueous solution is a microminiature cryogenic refrigeration system 85 which comprises a countercurrent heat exchanger, an expansion nozzle, and a reservoir for the liquified refrigerant gas. Cooling is obtained through the Joule-Thomson effect from the expansion of high-pressure gas. For example, when nitrogen or argon is used at 200 to 400 atm, the refrigeration system 85 can attain temperatures, between 77° and 87° K. See, for example, W. A. Little, 1984, "Microminiature Refrigeration," Rev. Sci. Instrum. 55:661–680; and W. A. Little, 1990, Advances in Cryogenic Engineering, Vol. 35, R. W. Fast (ed.), Plenum Press, New York, pp. 1305–1314, which are incorporated herein by reference. The refrigeration system 85 is arranged with respect to the flow channels so as to establish a very steep temperature gradient between the nozzle 80 and the point of fluorescence excitation in the detection station 90. The temperature at the nozzle 80 is the temperature desired for the exonuclease reaction. Typically this temperature is 37° C. The temperature at the point of fluorescence detection is the temperature of maximum enhancement of native nucleotide fluorescence which will typically be in the range of 85°–170° K. In the preferred embodiment, the distance between the nozzle 80 and the point of fluorescence excitation is the minimum distance achievable, and typically is in the range of 1–3 cm, preferably 1 cm. Refrigerator designs which can provide such steep temperature gradients are known in the art (see Little supra).

FIG. 15 depicts an exploded view of an illustrative embodiment of a flow cell 500 which incorporates the foregoing elements of transport system 70 and provides access to the nucleotide-containing matrix 88 for purposes of detection and identification at detection station 90. The flow cell is made by joining together sheets of material in which are defined the various channels of the transport system 70, the refrigeration system 85 and other elements. Advantageously, these features are defined in the sheets using conventional photolithographic, techniques such as are used in the manufacture of integrated circuits. Details concerning the use of such techniques to fabricate a refrigeration system in semiconductor materials such as silicon and non-conducting materials such as glass are set forth in the W. A. Little papers cited immediately above. Details concerning the use of such techniques to fabricate a flow cell in semiconductors or in non-conductors are set forth in Sobek et al., U.S. patent application filed concurrently herewith.

Flow cell 500 comprises three sheets 510, 520, 530, illustratively made of glass. Refrigeration system 85 is implemented in the upper sheet 510. As shown in the case of sheet 510, the refrigeration system comprises a gas inlet 511, a gas outlet 512, a countercurrent heat exchanger 514, an expansion capillary 516 and a reservoir 518. For purposes of illustration, no attempt has been made to illustrate the depth of the channels in the heat exchanger or expansion capillary. Cooling is effected by supplying a high pressure gas to inlet 511 which passes through the countercurrent heat exchanger to the expansion capillary where it expands and cools. It then enters reservoir 518 and the cooled vapor passes back up the heat exchanger to outlet 512, precooling the incoming gas. A temperature gradient is thereby established between the cooled reservoir and the warm gas inlet and outlet. For simplicity the refrigeration system is operated in an open cycle with the pressurized gas being supplied from a high pressure tank.

Microchannel 76 is implemented in sheets 520, 530. The upper half of the channel is defined in sheet 520 and the lower half in sheet 530.

Also shown in FIG. 15 are nozzle 72 and heating element 73 which have been withdrawn from the opening of microchannel 75 for purposes of illustration, lines 86 and 87 which identify the region where hydrodynamic focusing takes place, and electrodes 89 which are used to orient the nucleotides be in matrix 88. Additional electrodes (not shown) may also be used across the top and bottom sheets.

Radiation from radiation source 92 is directed to matrix 88 in microchannel 76 through the bottom of sheet 530 by an appropriate external lens (not shown). Similarly, the fluorescent emission from individual nucleotides 64 in matrix 88 is collected by the same external lens. Optical access to matrix 88 in the detection station may also be provided on the opposite side of flow cell 500 by imaging through the glass refrigerator 510 and the upper sheet of the flow channel 520. Optical access to matrix 88 in the detection station may also be provided through sheets 520, 530 by means of one or more waveguides 95 defined in the sheets.

The entire flow cell 500 is contained within a stainless steel vacuum dewar in order to thermally isolate the flow cell from the ambient environment (1982 Yakushi et al., Rev. Sci. Instrum. 53:1291–1293, which is incorporated herein by reference). The dewar is provided with optical windows positioned over the flow cell so as to provide optical access to the device for purposes of fluorescence detection of the nucleotides 64 and manipulation of the DNA molecule 66 by means of the optical trap 69 operating on the optical handle 68. In order to maximize the light collection efficiency of the objective lens, a high numerical aperture is desired. A high numerical aperture is also desired to form the optical trap 69. It is therefore desirable to minimize the working distance between the objective lens and the matrix 88. This can be achieved by using a minimal thickness window in the vacuum dewar, minimizing the vacuum gap between the inside surface of the window and the surface of the flow cell 500, and minimizing the thickness of the sheet 530 in which microchannels 75 and 76 are formed, and minimizing the depth of microchannel 76 itself. In an alternative embodiment of the invention, the flow cell 500 and the vacuum dewar are both fashioned from glass as a single monolithic structure.

By using photolithographic techniques it is possible to make the flow cell with microminiature dimensions. For example, microchannel 76 may have a cross-section on the order of 100 micrometers or less and a length of only a few centimeters. Similarly the channels of the heat exchanger may have cross-sections of 250 micrometers or less and the entire longitudinal length of the refrigeration system along microchannel 76 may be one or two centimeters.

In those embodiments where the individual nucleotides are vitrified into a solid, glassy matrix by rapid cooling, the sample stream may include various chemical agents to facilitate vitrification by raising the glass transition temperature above that for pure water and/or to provide a more rigid and cohesive matrix for incorporation of the nucleotides and fluorescence enhancement. The glass transitions and other phase and mechanical properties of such glass forming solutions are well known in the art for agents including methanol, glycerol, ethylene glycol, polyethylene glycol, propylene glycol, polyvinyl-pyrrolidone, sucrose, glucose, and dimethylsulfoxide (Luyet and Kroener, 1966, Biodynamica 10:33–40; Kroener and Luyet, 1966, Biodynamica 10:41–45; Kroener and Luyet, 1966, Biodynamica 10:47–52; Luyet and Rasmussen, 1967, Biodynamica 10:137–147; Luyet and Rasmussen, 1968, Biodynamica 10:167–191; Rasmussen and MacKenzie, 1968, Nature 220:1316–1317; Rasmussen and MacKenzie, 1971, J. Phys. Chem. 75:967–973; and MacFarlane et al., 1986, Cryo-Letters 7:73–80, which are incorporated herein by reference).

Figure 12:
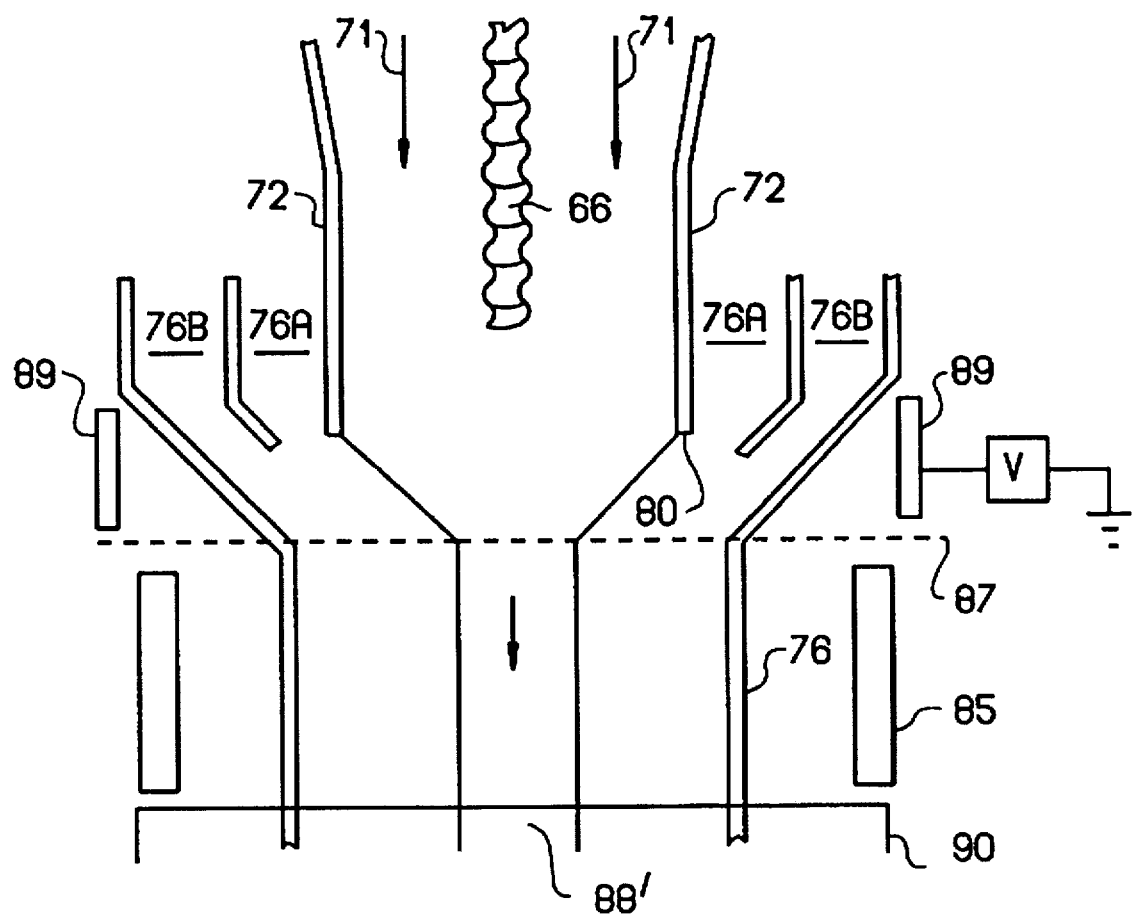
FIG. 12 depicts an alternative to the apparatus of FIG. 8.

Another manner of solidifying the aqueous solution is by polymerization. Polymerization may be accomplished in two main ways. First, the polymerizing compounds may be incorporated in the aqueous solution if they do not interfere with the action of the exonuclease. Polymerization can then be initiated either by irradiation of the aqueous polymer-containing solution upon exiting the nozzle 80 (1993 Misawa et al., Macromolec. in press, which is incorporated herein by reference), or by incorporation in the sheath liquid 77, of a chemical initiator which can diffuse into the hydrodynamically-focused sample stream. Second, a modified transport system 70 can be employed which incorporates a second sheath flow as depicted in FIG. 12. Multiple sheath flow devices are already known in the art (Fox and Coulter, 1980, Cytometry 1:21–25; Steinkamp et al., 1973, Rev. Sci. Instrum. 44:1301–1310, which are incorporated herein by reference). With such a dual-sheath transport system, it is possible to employ polymerizing compounds which are incompatible with the exonuclease. Such compounds are dissolved in an appropriate solvent which is miscible with the aqueous sample stream 71 and introduced under laminar flow in an inner sheath microchannel 76A. During a first stage of hydrodynamic focusing, the polymerizing compounds diffuse into the nucleotide-containing sample stream. An immiscible outer sheath is then introduced through an outer microchannel 76B to provide a second stage of hydrodynamic focusing. Polymerization can be initiated as described supra. In both cases, the polymerization conditions are selected to accomplish two goals. The first goal is to ensure that lo insufficient polymerization occurs in the region upstream of line 87 so as not to interfere with hydrodynamic focusing. The second goal is to ensure that sufficient polymerization has occurred by detection station 90 to solidify the nucleotide in the solid matrix 88'.

Representative compounds useful in polymerizing the aqueous solution include, for example, polyvinyl alcohol, polymethylmethacrylate (PMMA), polyacrylamide, or silica glass (1988 S. Luo and K. Tian, "Low Temperature Synthesis of Monolithic Silica Glass from the System Si(OC$_2$H$_5$)$_4$—H$_2$O—HCl—HOCH$_2$CH$_2$OH by the Sol-Gel Method," J. Non-Crystalline Solids 100:254–262, which is incorporated herein by reference).

In yet another embodiment of the present invention, the fluorescence-enhancing matrix is achieved in two steps, by first polymerizing the nucleotide containing sample stream as described supra, and then subsequently cooling the polymerized sample stream with a temperature gradient as also described supra.

In any of the possible methods which might be utilized to solidify the nucleotide-containing sample stream, the outer sheath will remain fluid and non-viscous while the viscosity of the core will increase substantially during cooling and/or polymerization. It is well known in the art that when immiscible liquids with different viscosities are forced to flow through a channel, the more viscous liquid tends to concentrate in the center (Stockman et al., 1990, Nature 348:523–525; Karagiannis et al., 1988, Polymer Engineering and Science 28:982–988; 1991 Brauner, Int. J. Multiphase Flow 17:59–76, which are incorporated herein by reference). The flow properties of the instant invention are therefore known to be stable (1992 Brauner and Maron, Int. J. Multiphase Flow, 18:123–140, which is incorporated herein by reference).

The incorporation of the individual nucleotides into a solid matrix provides a number of distinct and important advantages for the subsequent steps of rapidly and accurately detecting and identifying each individual nucleotide. Hydrodynamically-focused flow cells known in the prior art have employed miscible sheath and sample solutions wherein the sample analyte is soluble in both liquids. Typically the outer sheath liquid is either water or the same aqueous buffer solution that is used to introduce the sample. Even though it is possible to hydrodynamically focus the sample stream to a cross-section on the order of ~1 micrometer or less (i.e., the flow lines for the inner stream are reduced to that dimension), analyte molecules entrained in the flow are not restricted in their diffusion and therefore increase the effective diameter of the actual sample stream over the theoretically predicted diameter. The magnitude of this diffusional broadening of the sample stream is dependent on the diffusion constant of the analyte molecule, the temperature and viscosity of the solution, and the residence time in the flow from the point of mixing of the sample and sheath streams. Such diffusional broadening can substantially limit the effectiveness of hydrodynamic focusing and requires the excitation of a significantly larger volume in order to insure that a single analyte molecule is contained within that volume, as has been observed in the prior art by Nguyen et al. (1987, J. Opt. Soc. Am. B 4:138–143, which is incorporated herein by reference). As a consequence, Rayleigh and Raman scattering as well as background emission from any fluorescent impurities are increased, degrading the performance of the detection system.

In the novel design of the present invention, the sample and sheath liquids are immiscible and the single nucleotides are insoluble in the sheath (e.g., charged nucleotides are insoluble in a non-polar propane sheath). As a consequence, the nucleotide is limited in its lateral diffusion to remain within the sample liquid, and hydrodynamic focusing can therefore achieve theoretically predicted cross sections.

The solidification by cooling and/or polymerization of the hydrodynamically-focused, nucleotide-containing sample stream confers yet additional advantages. A single analyte molecule in solution undergoes rotational diffusion which constantly changes the orientation of the molecule. As a consequence, for a molecule which is undergoing repeated cycles of fluorescence, the photons are emitted into 4π stearadians. Efficient collection of emitted photons is crucial for detection and discrimination of single nucleotides. A single, high numerical aperature objective lens of the type typically used to collect the fluorescent emission from sheath flow cuvettes might have a collection efficiency of only ~10% (Wu and Dovichi, 1989, J. Chromatog. 480:141–155, which is incorporated herein by reference). Nine out of ten photons are simply missed. More elaborate optical collection schemes have been devised, including the incorporation of a concave retroreflective mirror to effectively double the collection efficiency of a single objective lens (Nguyen et al., 1987, J. Opt. Soc. Am. B 4:138–143), the addition of a planoconvex lens to the flow cell (Fox and Coulter, 1980, Cytometry 1:21–25), ellipsoidal flow chambers (Skogen-Hagenson et al., 1977, J. Histochem. Cytochem. 25:784–789), spherico-ellipsoidal flow chambers (Watson, 1989, Cytometry 10:681-688), as well as other methods (Watson, 1985, Br. J. Cancer 51:433–435; Leif and Wells, 1987, Applied Optics 26:3244–3248, which are incorporated herein by reference), but none of them have proved practical.

In the novel design of the present invention, the single nucleotides are oriented by electrodes 89 and incorporated into a solid matrix as described supra, which limits the diffusion of an individual nucleotide such that it can be considered to be in a fixed and known orientation during the time required for fluorescent detection and identification (infra). A molecule can only absorb a photon if the instantaneous electric field vector of the incident light is parallel to the internal molecular dipole. For a molecule with a fixed and known orientation, it is therefore possible to choose the alignment and polarization of the incident beam for maximal efficiency of excitation.

Similarly, a molecule with a fixed and known orientation in the excited state will emit a fluorescent photon in a particular vector direction with respect to its internal dipole, allowing one to position a collecting lens with a sufficiently large angle of acceptance in such a position and orientation with respect to the molecule so as to efficiently collect all of the emitted photons. Essentially the fluorescence is restricted to a cone of emission rather than a sphere, greatly enhancing the efficiency of photon collection, which in turn results in superior photon counting statistics (infra) and increased speed and accuracy of sequencing.

Another major factor which affects the photon counting statistics is the photostability of the nucleotides. Fluorescent organic compounds such as nucleotides have finite photobleaching half-lives, and cannot undergo an infinite number of cycles of fluorescent excitation and emission. In order to maximize the number of detected photons per nucleotide and thereby the accuracy of the nucleotide identification, conditions which provide the maximum photostability are desired. The instant invention provides such conditions by incorporating the nucleotide in a rigid, solid matrix which greatly restricts the translational, rotational and vibrational degrees of freedom of the molecule and provides isolation from other nucleotides, impurities, and photodecomposition products. Such solid matrices are known in the prior art to enhance the quantum yield of fluorescence while at the same time reducing the quantum yield of photobleaching for organic dyes (Avnir et al., 1984, J. Phys. Chem. 88:5956–5959; Gromov et al., 1985, J. Opt. Soc. Am. B 2:1028–1031; Rodchenkova et al., 1986, Opt. Spectrosc. (USSR) 60:35–37; Bondar et al., 1987, Opt. Spectrosc.

(USSR) 62:798–800; Reisfeld, 1987, Journal de Physique 48:C7-423–426; Reisfeld et al., 1988, SPIE: French-Israeli Workshop on Solid State Lasers 1182:230–239, which are incorporated herein by reference). Cooling of the nucleotide-containing matrix provides other advantages for photostability by further reducing the translational, rotational and vibrational degrees of freedom of the nucleotide and greatly reducing or eliminating any thermal processes which might contribute to photoinstability.

In certain embodiments, it will be advantageous to introduce other chemical compounds in the nucleotide-containing sample flow to yet further enhance both florescence and photostability, and to enable the discrimination of the different nucleotides by virtue of their fluorescence properties. Such compounds might include acids or bases which will alter the pH to produce protonated or deprotonated forms of the nucleotides, or triplet state quenching compounds to reduce or eliminate the time a nucleotide might spend in the triplet state, thereby improving the speed of sequencing. It will also generally be advantageous to deoxygenate all solutions and reagents which come in contact with the individual nucleotides, to further reduce possible sources of photooxidation. Compounds which can scavenge free radicals can similarly be added to the nucleotide-containing sample stream to reduce radical-initiated photoinstability. In those cases where any of these chemical additives (supra) are incompatible with the desired activity of the nuclease, they can be introduced by means of a dual-sheath flow cell (FIG. 12) as described for incompatible polymerizing agents (supra). In another embodiment of the present invention, chemical agents are included in the sample flow which cause the chemical and/or photochemical conversion of individual nucleotides entrained in the flow into compounds with superior fluorescence properties for detection and discrimination. An example of such photochemical conversion would include but not be limited to the conversion of guanines in the presence of diols when irradiated at wavelengths below 300 nm at temperatures between 140°–190° K. (1979 J. P. Morgan and P. R. Callis, "Photochemistry and Photophysics of Guanine-Containing Dinucleotides," Photochem. Photobiol. 29:1107–1113, which is incorporated herein by reference.) It will be recognized by those skilled in the art that any chemical additive described supra must also be compatible with the fluorescent detection of the nucleotides.

5.3.3. DISCONTINUOUS TRANSPORT & DETECTION

Figure 13:
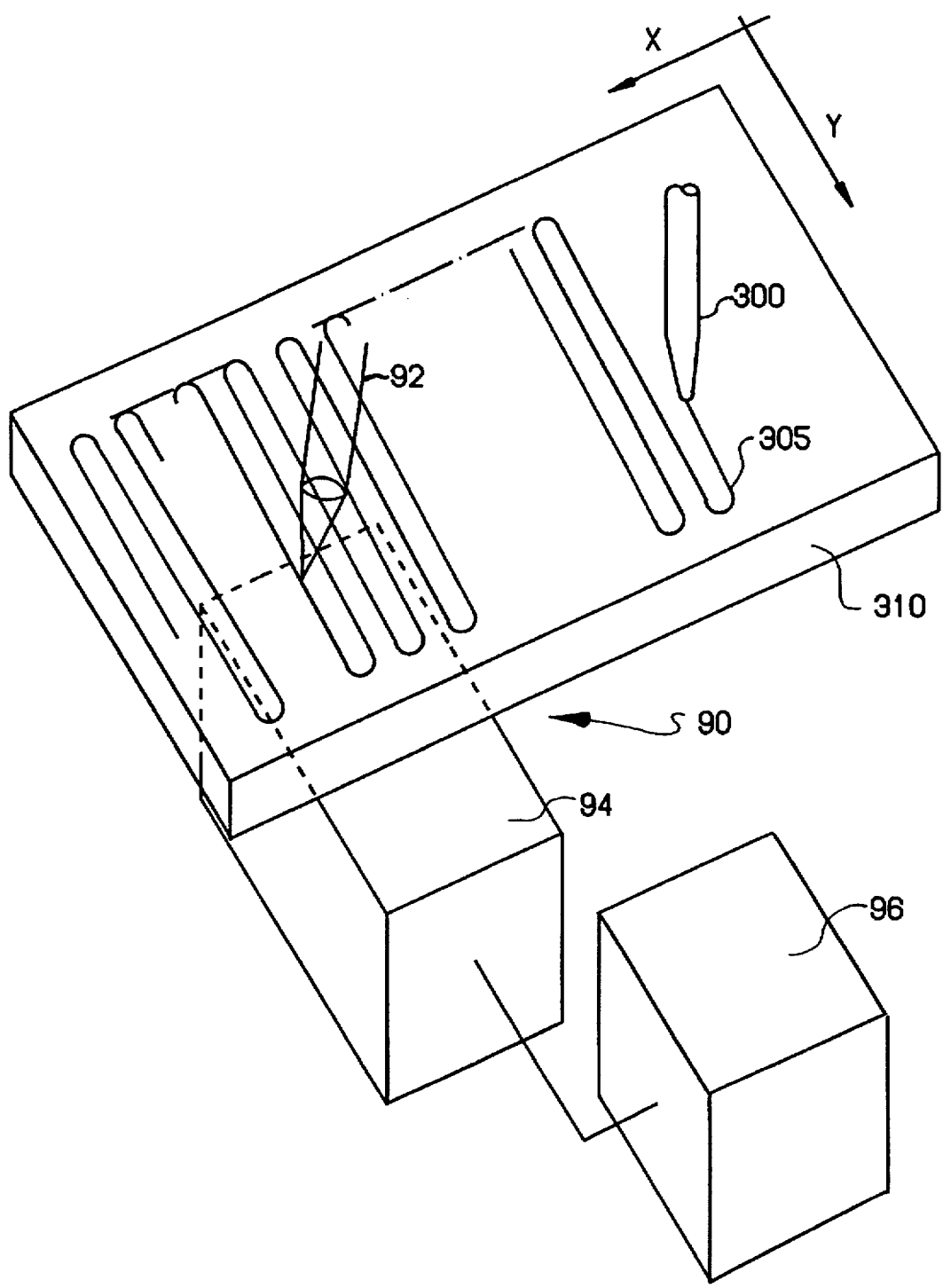
FIG. 13 depicts an alternative to the apparatus of FIGS. 8 and 9.

The second class of transport system provides for the discontinuous transport and detection of individual nucleotides as illustrated in FIG. 13. In such transport systems, the individual nucleotides generated by the processive exonuclease are entrained in a hydrodynamically focused flow by any of the methods described supra, and are then deposited by a nozzle 300 in a thin continuous liquid film 305 or as discrete droplets on a transparent support 310. The liquid film or droplets are then solidified on the solid support by cooling the support and/or polymerization to provide the fluorescence-enhancing matrix as described supra. Finally, the film is transported by movement of support 310 through a detection station 90 where it is irradiated by a radiation source 92; and the resulting fluorescence is detected by detection system 94 and identified by computer 96 as described in more detail below.

The support can take the form of any surface geometry which can be moved with respect to the output nozzle 300 so as to allow for the deposit of the nucleotide containing liquid stream in such a manner that the position of deposit of each nucleotide 308 is both unique and known (Merrill et al., 1979, J. Histochem. Cytochem. 27:280–283, which is incorporated herein by reference). Uniqueness requires that individual nucleotides are deposited on the surface with sufficient distance between each nucleotide and any other nucleotide so as to be isolated in an optically-resolvable volume element during the subsequent step of nucleotide detection and identification infra. The sequential position of deposit of each nucleotide 308 must be known with sufficient accuracy so as to be able to position the volume element containing each nucleotide with respect to the excitation volume of the detection system infra. Although a random pattern of nucleotide deposition on a surface of arbitrary geometry is possible, preferred embodiments employ regular patterns of deposition on simple surface geometries. Examples include linear deposition on a moving tape (Schildkraut et al., 1979, J. Histochem. Cytochem. 27:289–292), deposition in a spiral pattern or concentric circles on a rotating disk, deposition by translational movement in a two-dimensional grid on a rectilinear surface (Stovel and Sweet, 1979, J. Histochem. Cytochem. 27:284–288, which are incorporated herein by reference), or by deposition in spiral or circumferential tracks on the cylindrical surface of a rotating drum.

5.4. DETECTION STATION

In accordance with the invention, individual nucleotides in solid, fluorescence-enhancing matrix are identified at detection station 90 by stimulating and detecting their natural fluorescence. At room temperature in aqueous solution, individual native nucleotides found in DNA have intrinsic fluorescence quantum yields less than $10^{-3}$ making detection of a single nucleotide inherently difficult if not impossible. Low quantum yields are largely due to efficient non-radiative deexcitation pathways for a nucleotide Under these conditions. Upon exciting the nucleotide with an appropriate wavelength of light, it is more probable that the nucleotide will return to the ground state by such a non-radiative internal conversion process, accounting for the weak fluorescence observed and reported in the literature. Accordingly, other proposed fluorescence techniques for the rapid sequencing of single large fragments of DNA are typically based upon the prior labeling of each nucleotide with specific tags or fluorescent dyes that have large fluorescence quantum yields, typically ~0.9. See, for example, U.S. Pat. No. 4,962,037 issued to Jett et al., which is incorporated herein by reference.

In accordance with the present invention, the nucleotides are contained in a solid matrix 88 that enhances the fluorescence of the nucleotides to levels near or comparable to those of fluorescent dyes used for tagging. For example, Børresen reported a quantum yield of fluorescence for guanosine in 1:9 v/v water:methanol 0.01 N $H_2SO_4$ at 147° K. of 0.93 (1967, Acta Chemica Scand. 21:920–936, which is incorporated herein by reference). Placing the individual nucleotides in an appropriate solid matrix has the effect of limiting the internal degrees of freedom of motion of the nucleotide, increasing the probability of fluorescent emission and therefore quantum yield. Advantageously, the composition and temperature of the nucleotide-containing matrix is selected to both maximize the fluorescence of the nucleotides and to facilitate the differentiation of one type of nucleotide from another as described infra.

The four native nucleotide found in DNA have first excited singlet states which may be populated by irradiation with ultraviolet light, typically between 240–300 nanometers. In accordance with the invention, the wavelength of an irradiating laser beam is matched to the maximum in the nucleotide excitation spectrum that yields the strongest fluorescence or highest quantum yield. For example, adenine at 77° K. has a quantum yield at an excitation wavelength of 282 nm that is twice the value for a wavelength of 270 nm. Fluorescent emission from the first singlet state to the ground state results in fluorescence in a wavelength band of 300–450 nm for native nucleotides (see, for example, Gueron et al., 1974, "Excited States of Nucleic Acids" in Basic . Principles in Nucleic Acid Chemistry, Vol. 1, Academic Press, New York, pp. 311–98, which is incorporated herein by reference).

In operation, a laser beam optically excites each nucleotide that has been cleaved from the DNA strand. In a preferred embodiment, each nucleotide is excited repeatedly during its transit time through the laser beam by using temporally short excitation pulses from a mode-locked laser. The fluorescence or transition from the excited state to the ground state is then detected by a suitable detector. Advantageously, the spectroscopic emission has a characteristic fluorescence band and decay half-life that may be used to identify each type of nucleotide. Various detectors such as streak cameras or multichannel time-correlated single-photon counting systems and the like are used to detect the time-resolved fluorescent emission spectrum.

As shown in FIG. 9, solid matrix 88 is carried by sheath fluid 77 into an excitation region 100 in detection station 90. There, a highly focused laser beam 105 intersects the solid matrix at right angles. More particularly, the waist of laser beam 105 is centered on the axis of the solid matrix. In this manner, a probe volume of about a few tenths of a picoliter to as little as one femtoliter results. The extremely small probe volume is desirable to maximize the ratio of the fluorescence signal from the nucleotide to the background Rayleigh and Raman scattering or fluorescence from contaminant molecules in the probe volume. Since the background signal scales linearly with probe volume, the background signal can be decreased by decreasing the probe volume while the fluorescence signal of a single nucleotide contained in the probe volume remains constant.

The detection of nucleotides in a continuous film 305 or in discrete droplets on a support 310 is similar to the detection of nucleotides in matrix 88. As indicated in FIG. 13, film 305 (or droplets) is moved through a beam of radiation from a radiation source 92 and fluorescence is detected by a detector system 94. However, in this case the cross-sectional dimension of film 305 (or of the droplets) is almost certain to be much greater than the one micron diameter of matrix 88. In such case it will be advantageous to scan the laser beam transversely to the direction of motion of the film (or droplet) through the detection station. Such scanning motion can readily be implemented by directing the laser beam at a rotating mirror such that the reflected beam sweeps across the path of the moving film.

The intensity of each laser pulse is appropriately chosen so as to insure saturation of the fluorescence excitation as individual nucleotides traverse laser beam 105. Excitation intensity which exceeds that required for saturation of fluorescence is undesirable from the standpoint of minimizing photobleaching and avoiding 2-photon processes. Laser power is adjusted by varying the angle of a half-wave plate 113 with respect to polarizer 112, or by other appropriate means. Advantageously, the laser polarization is also chosen so as to minimize Rayleigh and Raman scattering into the detector field of view. This is accomplished by appropriately rotating polarizer 112.

The shape and dimensions of excitation region 100 are chosen so as to provide uniform irradiation of solid matrix 88 as it passes through laser beam 105. It is desirable to avoid or minimize any irradiation of the nucleotide-containing matrix 88 upstream of the point of fluorescence detection so as to avoid or minimize undesirable photobleaching of those nucleotides which are next to be detected. For a simple Gaussian focused beam, the $1/e^2$ intensity occurs at a beam waist $w_o$ and the intensity as a function of the radius from the central beam axis is given by $I(r)=I(0)\exp(-2r^2 w_o^2)$. For example, if solid matrix 88 is approximately 1 µm in diameter and laser beam 105 is focused by lens 125 to a waist diameter of approximately 5 µm, then the matrix will be within the >90% intensity region of the beam. In more complex geometries, lens 125 is a cylindrical lens which focuses laser beam 105 to an ellipsoid whose major axis is coaxial with the central axis of solid matrix 88.

Lens 125 may be a refracting microscope objective or a reflecting objective such as those made by Ealing Electro-Optics, Holliston Mass.

Laser beam 105 is generated by radiation source 92 which preferably is a mode-locked laser 110. In a preferred embodiment, laser 110 comprises an argon ion pumped, mode-locked Ti:sapphire laser whose output is frequency tripled to provide tunable femto-or picosecond pulses over the wavelength range of 240–300 nm at a mode-locked rate of 76 MHz. Suitable argon and mode-locked Ti:sapphire lasers are available as models INNOVA 420 and MIRA 900 respectively from the Laser Products Division of Coherent, Inc., Palo Alto, Calif. Devices suitable for generating second and third harmonic output from the Ti:sapphire laser are available using appropriate thickness beta barium borate (BBO) crystals (typically 1.0–2.0 mm) in two Model Ti:Sapphire Autotracker II units with a Model BC-BH1000/TS polarization rotation assembly between them, which are available from INRAD in Northvale, N.J. In an alternative embodiment, laser 110 comprises a mode-locked Nd:YAG laser ($\lambda$=1064 nm) whose output is frequency-tripled to pump a laser dye such as Coumarin 500 in a dye laser whose output is frequency-doubled to produce tunable picosecond, ultraviolet excitation pulses in the wavelength range of 240–300 nm and at a repetition rate of 76 MHz. Preferably, mode-locked laser 110 is tuned at a wavelength of ~260 nm, with an average power of 1–2 mW and a pulse width of about 1 psec. Suitable Nd:YAG lasers, mode-lockers, third harmonic generation devices, Coumarin 500 tunable dye lasers, and second harmonic generation devices are available as models ANTARES 76-S, 468-ASE, 7950, 701, and 7049 respectively, from the Laser Products Division of Coherent, Inc., Palo Alto, Calif.

In those alternative embodiments of the present invention described supra in which fluorescent nucleotide analogs, dye-tagged nucleotides or various combinations of native nucleotides, fluorescent nucleotide analogs, and/or dye-tagged nucleotides are incorporated into the DNA to be sequenced, it will be obvious to one skilled in the art that the laser excitation source will need to be modified from that described supra so as to provide optimal excitation wavelengths for the types of nucleotides employed. Fluorescent nucleotide analogs and dye-tagged nucleotides typically have excitation maxima in the near UV or visible range, unlike native nucleotides. In general, such wavelengths are easier to generate with available laser technology than the deeper UV. In the most complex situation, four discrete laser sources may be required to provide optimal excitation for four different types of nucleotides.

Time-correlated single photon counting (TCSPC) is used to detect the individual nucleotides (see, for example, O'connor et al., 1984, Time-Correlated Single Photon Counting, Academic Press, New York; Rigler et al., 1984, "Picosecond Single Photon Fluorescence Spectroscopy of Nucleic Acids," in Springer Series in Chemical Physics, Vol. 38, pp. 472–476, which are incorporated herein by reference). With time-correlated single photon counting, the delay in the arrival time of a single fluorescent photon after a very short laser pulse is measured. By repeating this process many times in rapid succession, it is possible to accumulate a large statistical sample of single fluorescent photon events from which the fluorescent half-life of the nucleotide can be determined. Those skilled in the art will realize that single photon counting inherently provides greater noise immunity than other detection techniques (1972 H. V. Malmstadt, M. L. Franklin, G. Horlick, "Photon Counting for Spectrophotometry," Anal. Chem. 44:63A–76A, which is incorporated herein by reference).

In a preferred embodiment, the full time-resolved emission spectrum of each individual nucleotide is recorded by employing a streak camera 150. This arrangement provides a measurement of the 3-D contour of the fluorescence intensity versus time and wavelength. At the time solid matrix 88 is irradiated by laser beam 105, a signal 137 is generated-indicating the onset of a laser pulse. Illustratively, signal 137 is generated by inserting a beam-splitter 115 into the path of laser beam 105 so as to split off an auxiliary laser beam 107. Beam 107 is incident on a fast photodiode 120 which produces an output signal that is supplied to discriminator 122. Discriminator 122 is set to generate an output signal 137 representing the occurrence of an excitation pulse from laser 110 only when the number of photoelectrons incident on photodiode 120 exceeds a threshold value, thereby eliminating false detection.

Fluorescence emission 130 from the nucleotide is collected by a high numerical aperture lens 145, spatially and spectrally filtered, directed through a prism 170, or other dispersive element such as a monochromator, and focused onto a photocathode 175. It will be recognized that lenses 145 and 125 can be a common lens which both focuses the exciting laser beam 105 and collects fluorescent emission 130 as is commonly practiced in epifluorescence microscopy. If such a common lens is used, an additional dichroic beam splitter (not shown) must be included to combine and separate the two optical paths. Prism 170 disperses incident photons, deviating the path of the photons along the x-axis according to their wavelength. Wavelengths outside of the fluorescent emission band of the nucleotides are excluded by such means.

Signal 137 is used to synchronize the modelocked frequency of the laser with a sinusoidal voltage generator 180 to trigger high voltage sweeps across orthogonal electrode pairs, one pair of which is shown as electrodes 182A and B in FIG. 9 and the other pair of which is at right angles thereto. Advantageously, the sweep frequency is such that only a single sweep takes place between successive laser pulses. The single photo-electron emitted when the single fluorescent photon strikes photo-cathode 175 is accelerated in the high vacuum inside the streak tube by extraction grid 177 and experiences a unique electrical field that is a function of the time of emission of the single photon after the laser pulse. As a result, the single photo-electron strikes microchannel plate 185 at a point along the y-axis proportional to its emission time. Accordingly, the spatial coordinates of the photoelectron incident on micro-channel plate 185 are representative of the delay time and wavelength of each detected photon. These coordinates are digitized by digitizer 190 and provided to computer 96.

As long as the nucleotide remains within excitation region 100, the nucleotide goes through repeated cycles of excitation and emission. For each fluorescent photon that is detected, the time of detection is converted to a spatial coordinate along the y-axis and the wavelength is converted to a spatial coordinate along the x-axis. These spatial coordinates are digitized by digitizer 190 and provided to computer 96. As a result, for a large number of detections, a histogram is developed which records the number of photons detected in appropriate time intervals after irradiation and appropriate wavelengths. For each of the four nucleotides, these histograms are characteristic.

Accordingly, to identify each nucleotide, the histogram that is generated for each detected nucleotide is compared with the previously recorded reference histograms of each of the four nucleotides. To this end, the previously recorded reference histograms are stored in computer 96; and as each histogram of a detected nucleotide is generated, it is compared by computer 96 with the stored histograms.

More particularly, when the nucleotide has completed the transit of the laser beam, as evidenced by a reduction below a predetermined threshold in the rate of total photon counting indicative of the nucleotide-free matrix between successive nucleotides, the histogram that has just been recorded in memory is processed by computer 96 while a second bank of memory is used to record the next histogram. Various computer algorithms, including neural networks, may be employed to identify the best match of the sampled single nucleotide histogram to the reference histograms. In addition, the recorded histogram of the single nucleotide may be archived for off-line analysis by transferring the data to a high capacity disk drive, such as a write-once read many (WORM) optical drive. In making comparisons of the recorded single nucleotide histogram with reference histograms of the different native and modified nucleotides (e.g., 5-methylcytosine), it will also be possible to perform a comparison with reference histograms for known fluorescent contaminants which are present in the system. Such histograms can be previously obtained by recording the transit of single fluorescent contaminant molecules through the excitation volume when no nucleotides are present in the system. By recording histograms on the blank solid matrix and sheath it is possible to develop fingerprints for contaminants which are characteristic of the system, and to thereby increase the accuracy of nucleotide identification. Such information about fluorescent contaminants in the blank solid matrix and sheath can also be utilized to refine purification schemes designed to further reduce or eliminate such contaminants from the system. For certain fluorescent contaminants, an alternative means of eliminating their contribution to the background will be to irradiate the sample and/or sheath liquids with ultraviolet light of sufficient intensity and duration to bleach the contaminants upstream of their point of introduction into microchannels 62 or 77. Such bleaching of fluorescent contaminants may be accomplished by using the 254 nm line of a mercury lamp or other similar sources.

For optimal use in the present application, the streak camera has several features. The streak camera window 152 must be highly transmissive in the near ultraviolet region of fluorescent emission by native nucleotides between 300–450 nm. Windows of $MgF_2$ provide ideal transmission characteristics, but windows of sapphire, fused silica or UV-transmitting glass may also be employed. Alternatively, a windowless streak tube may be employed, requiring a vacuum to be maintained between the photocathode 175 and at least the next preceding optical element in the collection system such as prism 170.

The photocathode 175 should have the highest possible quantum efficiency for photons in the range of 300–450 nm. Bialkali photocathodes with quantum efficiencies exceeding 25% are available commercially (Hamamatsu Photonics, Bridgewater, N.J.). Even higher quantum efficiencies are possible using specifically designed super lattice photocathodes (Howorth et al., 1989, SPIE: New Methods in Microscopy and Low Light Imaging 1161:189–196, which is incorporated herein by reference), in those embodiments of the present invention which employ fluorescent nucleotide analogs and/or dye-tagged nucleotides, it will be obvious to those skilled in the art that the specific properties of the streak camera described supra will need to be modified to accomodate the fluorescent emission properties of these nucleotides. In general, the emission bands for such nucleotides will be in the visible range.

As indicated above, it is desirable to synchronize the mode-locked laser with the sweep frequency of the streak tube, such that a single sweep is recorded between successive laser pulses. It is also desirable that the return sweep be deflected by an orthogonal synchronous sweep to provide blanking. Such synchroscan streak cameras with synchronous blanking have been developed (Tsuchiya et al., 1986, SPIE: High Speed Photography, Videography, and Photonics IV 693:125–133, which is incorporated herein by reference) and commercial units which can be synchronized to the 76 MHz mode-locked frequency of the Ti:sapphire laser are available from Hamamatsu Photonics, Bridgewater, N.J. as Model C1587 Universal Streak Camera with M1955 Synchroscan Unit and M2567 SynChronous Blanking Unit.

Since single photoelectrons are being recorded by the streak camera, a microchannel plate electron amplifier 187 is incorporated in the streak tube to provide for single photon counting. Such photon-counting streak cameras have been developed (Urakami et al., 1986, SPIE: High Speed Photography, Videography, and Photonics IV 693:98–104, which is incorporated herein by reference), and will preferably employ a two-stage, proximity-focused microchannel plate with 6 micrometer diameter channels.

The coordinates of the amplified electron pulse must be rapidly digitized at the output anode of the microchannel plate. In conventional streak cameras, a phosphorescent screen is typically employed to convert the electrons back to photons which can then be recorded by photographic film or by a charge-coupled device (CCD) or other video camera. For use in the current invention, the streak camera preferably is able to record the time-resolved fluorescent emission spectrum of a single nucleotide, digitize the spectrum and transfer it to a computer for identification of the nucleotide, and record the spectrum of the next nucleotide in sequence. At a sequencing rate of 100 nucleotides per second, each nucleotide will spend 10 msec transiting the excitation volume of the focused laser beam. At a 76 MHz repetition rate for the mode-locked Ti:sapphire laser, each single nucleotide will be excited 760,000 times. When the single nucleotide has completed the transit of the excitation volume, the accumulated time-resolved spectrum is compared to reference spectra to identify the nucleotide. Accordingly, the computer has 10 msec to perform this identification, during the collection of the spectrum of the next sequential nucleotide, if the sequencing is to be done in real time.

Two methods for high-speed readout and digitization of the streak camera output are possible. In one embodiment, the output phosphor screen of the microchannel plate of the streak tube is replaced with a two-dimensional array of discrete output anodes. Each anode is in turn connected to a pulse discriminator and pulse counter which are capable of operating at the data rates required. The output of the pulse counter is used to increment the content of the appropriate address in fast solid-state memory corresponding to the delay time and wavelength of that anode, thereby accumulating the digitized time-resolved spectrum. Ultrafast, two-dimensional, multianode microchannel plate devices have been developed (Kume et al., 1988, Applied Optics 27:1170–1178, which is incorporated herein by reference) and can be incorporated into streak tubes. An alternative method for high-speed readout of the streak tube is to directly replace the output phosphor with a two-dimensional charge-coupled device (CCD) which can be read out at appropriate rates. Such streak cameras have also been developed (Cheng et al., 1978, J. Appl. Phys. 49:5421–5426; 1991 J. M. Bernet, G. Eumurian, C. Imhoff, "Streak cameras applied to spatial chronometry," SPIE Vol. 1539 *Ultrahigh- and High-Speed Photography, Videography, and Photonics,* pp. 89–99, which are incorporated herein by reference).

Figure 10:
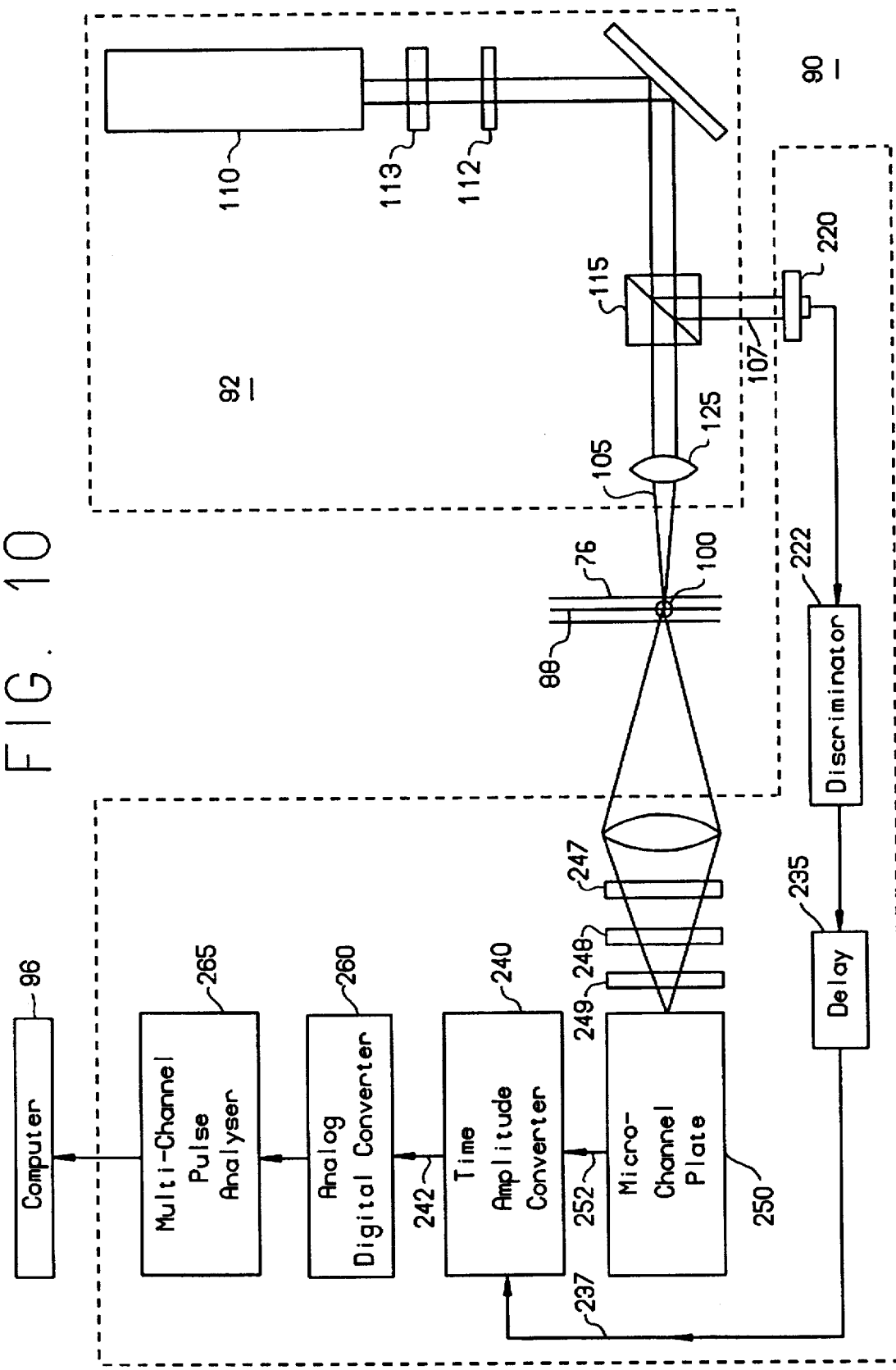
FIGS. 10 and 11 depict alternatives to various aspects of the apparatus of FIG. 9.

In an alternative embodiment shown in FIG. 10, the delay in arrival time of the fluorescent photon is measured directly. The excitation system is the same as that of FIG. 9. During a single excitation cycle, a single nucleotide absorbs a photon and undergoes a transition to the first excited singlet state. Simultaneously, photodiode 220 which monitors the excitation pulses, of laser beam 105 by monitoring laser beam 107 is triggered. The output from photodiode 220 is fed to a discriminator 222 which is set to record the occurrence of an excitation pulse from mode-locked laser 110 only when the number of photoelectrons incident on photodiode 220 exceeds a threshold value, eliminating false detection. Upon the detection of an excitation pulse, the output of discriminator 222 is provided to delay means 235, and the output of delay means 235 is provided as a start signal 237 to trigger a time-to-amplitude converter (TAC) 240. Converter 240 is essentially a ramp generator.

Radiation from the irradiated matrix 88 is collected by a lens 245 and directed through a filter 247 and a polarizer 248, and a vertical slit to a microchannel plate (MCP) 250. Filter 247 has a transmissive peak centered near the wavelengths of fluorescence of the nucleotides. Scattered light, both, Rayleigh and Raman, which are instantaneous and present only while laser beam 105 irradiates the sample, is collected by lens 245. Most of these scattered photons are filtered by wavelength filter 247 since the wavelengths of most of these photons differ from those of fluorescence from the nucleotides. Emitted fluorescence photons collected by lens 245 are spatially filtered by vertical slit 249 and detected by micro-channel plate 250.

Scattered photons not blocked by filter 247 may be discriminated from the longer lived fluorescence photons by techniques such as time-gated detection and polarization filtering. Time gating exploits the temporal difference between Rayleigh and Raman scattering and the fluorescence signal. Employing a fast MCP detector, such as MCP 250, it is possible to determine whether detected photons are coincident or delayed with respect to excitation pulses from laser beam 105. Photons that are coincident with the excitation pulses are due mainly to Rayleigh and Raman scattering while florescent photons are delayed due to the longer half-lives of the nucleotides. By gatingor time-gating a window to observe and measure only those photons which are delayed with respect to the excitation pulses from laser beam 105, the scattered light can be completely rejected.

If the nucleotides are oriented in solid matrix 88 in substantially the same direction, scattered radiation may also be reduced by polarization filtering since the fluorescence photons from the nucleotides are polarized along one substantially fixed direction while the scattered light is randomly polarized. Polarizer 248 is aligned with the polarization of the fluorescence from the nucleotides. As a result, it passes the fluorescence photons but blocks that portion of the scattered light which is not polarized in the direction of the polarizer.

Depending on the quantum efficiency of MCP 250, some fraction of photons collected by MCP 250 will emit a photoelectron and cause a signal 252 to be generated. Signal 252 is passed through a constant fraction discriminator (CFD) to eliminate background counts, and the output of the CFD is applied to TAC 240 to terminate its time-to-amplitude conversion. As a result, TAC 240 outputs a signal 242 proportional to the time delay between the moment of excitation and the moment of emission of the fluorescent photon from the excited nucleotide. Signal 242 is then digitized by an analog-to-digital (A/D) converter 260 and stored in the appropriate time channel of a multichannel analyzer (MCA) 265.

In an alternative mode of operation, it is possible to take advantage of the regular timing of the pulses from laser 110 and use signal 252 to initiate the time-to-amplitude conversion and signal 137 to terminate the conversion. In this case, signal 242 is inversely proportional to the time delay between emission and excitation. Advantageously, by operating TAC 240 in this inverted mode, the dead time associated with resetting the electronics is minimized, providing the maximum counting rate (G. R. Haugen, B. W. Wallin and F. E. Lytle (1979) Rev. Sci. Instrum. 50:64–72, which is incorporated herein by reference).

Identification of the nucleotides is similar to the procedures followed in the embodiment of FIG. 9. As long as the nucleotide remains within excitation region 100, the nucleotide goes through repeated cycles of excitation and emission. For each fluorescent photon that is detected, the time of detection is recorded in MCA 265. As a result, for a large number of detections, a histogram is developed which records the number of photons detected in appropriate time intervals after irradiation. For each of the four nucleotides, these histograms have characteristic decay times. Accordingly, to identify each nucleotide, the histogram developed by MCA 165 is compared by computer 96 with previously recorded reference histograms of each of the four nucleotides.

During each excitation cycle (about 13 nsec) of mode-locked laser 110, a single nucleotide will only be capable of emitting a single fluorescent photon. For a sample flow velocity of about 0.5 mm/sec, the transit time through a 5 μm excitation region is 10 msec. For a pulse repetition rate of 76 MHz, in 10 msec, a nucleotide will be excited a total of approximately 760,000 times.

Advantageously, the transit time is determined in combination with the repetition rate of the mode-locked laser and the fluorescent lifetimes of the nucleotides under the conditions of measurement to be approximately twice the photobleaching half-life of the single nucleotides under those same conditions. This provides, on average, the maximum possible number of collected photons per nucleotide, thereby providing the maximum statistical accuracy for nucleotide identification. Other flow rates and repetition rates may be also be used if fewer collected fluorescent photons are desired, resulting in an increase in the speed of sequencing and a reduction in the accuracy. Such a high-speed scanning mode of sequencing may prove useful in searching for genes in anonymous regions of genomic DNA. Considerable sequence error can be tolerated in some classes of sequence analysis (1991 States and Botstein, Proc. Natl. Acad. Sci. USA, 88:5518–5522, which is incorporated herein by reference).

The average number of photons that can be obtained by repeatedly exciting the nucleotide is the quantum yield (Q) x the total number of excitations per nucleotide, limited by the quantum yield of photobleaching. The photostability of the nucleotides is generally A>G>>T>C. The purines are generally, much more stable than the pyrimidines. The primary photoproducts which will result in the loss of fluorescence from the pyrimidines under the conditions of excitation employed in the present invention are reversible photohydrates (1976 Fisher and Johns, In:*Photochemistry and Photobleaching of Nucleic Acids*, S. Y. Wang (ed.) Academic Press, New York, Vol. 1, p. 169–224, which is incorporated herein by reference). For expected quantum yields of photobleaching for the four native nucleotides, it is anticipated on average that between $5 \times 10^4$ and $8 \times 10^5$ photons will be emitted by each nucleotide during a 10 msec transit time through laser beam 105. The statistical variation in the number of emitted photons will of course be the Poisson distribution $P(n,\bar{n}) = (\bar{n})^n e^{-\bar{n}}/n!$, where $\bar{n}$ is the average photon count expected, and $P(n,\bar{n})$ the probability that n photons are emitted by the nucleotide.

For an estimated collection efficiency of 10%, between 5,000 and 80,000 photons should be detected for each nucleotide. As with any detection system, the sensitivity is ultimately limited by the signal-to-noise ratio. Based on experience with similar time-correlated fluorescence detection systems, it is anticipated that fewer than one photon from background emission will be detected during the 10 msec transit time. Such a low background count is attributed to the utilization of pulsed laser excitation, time-gating and single photon counting.

For each laser excitation pulse, the delay time for each photon is measured by correlating the arrival of the photon to signal 137 which is locked to the repetition rate of mode-locked laser 110. The time resolution is ultimately limited by the pulse width of laser beam 105 as well as the transit time spread of MCP 150 and jitter time of TAC 140. Typical jitter times are on the order of a few psec. With micro-channel plates having a transit time spread of approximately tens of psec, it is contemplated that the photon delay time can be measured to within 50 psec. Those skilled in the art will readily note that the pulse width of laser beam 105 (about 1 psec) does not affect the resolution because it is substantially less than the transit time spread and jitter time.

Figure 11:
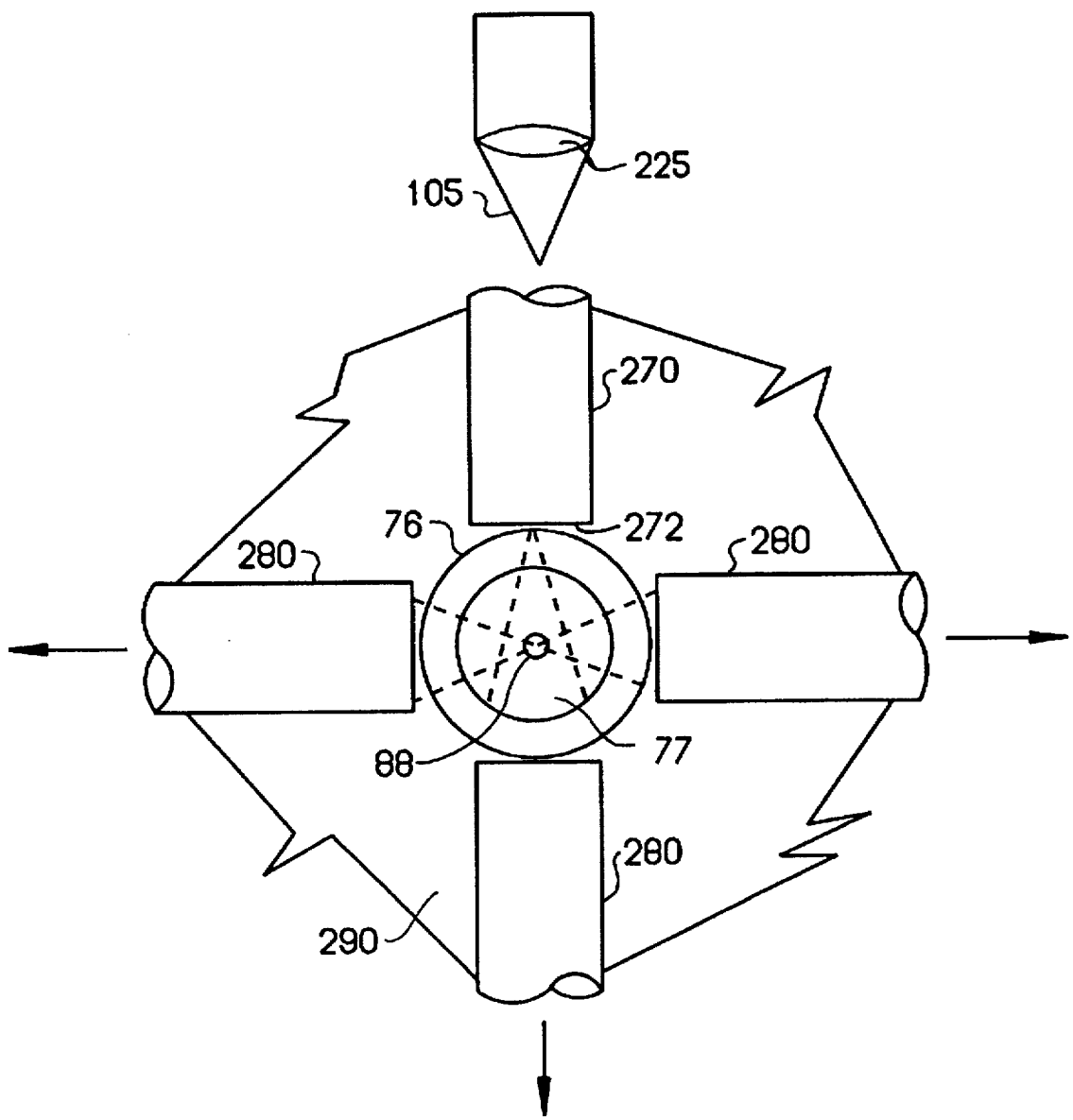

In an alternative embodiment, detection station 90 may employ fiber optics or other optical waveguides in place of lenses to illuminate and collect emitted photons from solid matrix 88. As illustrated in FIG. 11, excitation pulses from laser beam 105 are coupled by a lens 225 into a single mode optical fiber 270 that is optimized for transmission near a wavelength of 260 nm. End 272 of optical fiber 270 is disposed orthogonal to sheath flow stream 77 such that laser beam 105 uniformly illuminates solid matrix 88. Similarly, multi-mode optical fibers 280 are positioned around sheath flow stream 77 in order to maximize the collection solid angle of the fluorescence emission. Appropriate lenses such as self-focusing (SELFOC) or gradient refractive index (GRIN) lenses (not shown) may also be used to improve the collection efficiency of fibers 280.

Fibers 270 and 280 are fixed into a plate 290 having perpendicular grooves fashioned into the surface of the plate. With a hole of the appropriate diameter drilled through plate 290 at the point of intersection of the grooves, microchannel 76 is inserted through the hole. In this manner, each nucleotide may be observed during its transit in the microchannel as it traverses through the intersection point of fibers 280 and 290.

Alternatively, the function of one or more of fibers 270, 280 may be achieved using optical waveguides fabricated in the flow cell through which sheath flow stream 77 and solid matrix 88 flow. See Sobek et al., U.S. patent application filed concurrently herewith, which is incorporated herein by reference.

When employing fibers, each fiber preferably terminates in either a multiple-anode, micro-channel plate or a fast photodiode. It is anticipated that collection efficiency as high as 50% may be realized with the above design. Note that fibers 280 may be judiciously selected, such as by the appropriate selection of fiber material, to spectrally block Raman scattering from reaching the micro-channel plate.

The choice of fiber for the fluorescence collection is not affected by any requirement that the fibers preserve the modal structure of the collected light. High numerical aperture fibers may therefore be used for this purpose so long as their ends are close enough to the point of observation to subtend a solid angle equal to or larger than its corresponding numerical aperture.

In another embodiment, multichannel TCSPC is used to record the full time-resolved emission spectrum in a manner analogous to the streak camera supra. In a similar manner as above, dispersive elements such as prisms, gratings, holograms and the like, redirect the emitted photons to a linear array of fibers according to their wavelength. Each fiber is coupled to a micro-channel plate which generates fast timing pulses using a constant fraction discriminator. Each discriminator provides two coincident timing pulses, one to serve as a multiplexed stop signal and one to route the time-amplitude conversion to the appropriate memory segment of the multi-channel analyzer. Accordingly, the fluorescence decay rate for the discrete wavelengths are acquired simultaneously in separate segments of the MCA memory on a statistical time-sharing basis.

Other methods of multichannel TCSPC are known in the art and may be employed to measure the emission spectra. of each nucleotide. (D. J. S. Birch, A. S, Holmes, R. E Imhof and J. Cooper (1988) Chem. Phys. Lett. 148:435–444; D. J. S. Birch, A. S. Holmes, R. E. Imhof, B. Z. Nadolski (1988) "Multiplexed time-correlated single photon counting," SPIE Vol. 909 *Time-Resolved Laser Spectroscopy in Biochemistry*, pp. 8–14; J. R. Knutson (1988) "Fluorescence Detection: Schemes to Combine Speed, Sensitivity and Spatial Resolution," SPIE Vol. 909 *Time-Resolved Laser Spectroscopy in Biochemistry*, pp. 51–60: and J. M. Beechem, E. James, L. Brand (1990) "Time-resolved fluorescence studies of the protein folding process: New instrumentation, analysis, and experimental approaches," SPIE Vol. 1204 *Time-Resolved Laser Spectroscopy in Biochemistry II*, pp. 686–698; 1991 Courtney and Wilson, Rev. Sci. Instrum., 62:2100–2104, which are incorporated herein by reference).

In conventional time-correlated single photon counting, multiple photons are emitted during each excitation pulse, with only the first photon emitted by the sample detected and timed. Because of the inherent "dead time" required to reset the electronics, there results a bias in the counting statistics for photons emitted at short times after excitation when operating at high counting rates. Typically to avoid this problem, which is commonly known as "pulse pile-up", single photon counting instruments operate only at a fraction of the maximum data collection rate. For example, it is not uncommon that the ratio of the number of detected photons to the number of excitation cycles to be as low as 0.001.

In the present invention, there is only one nucleotide present in the detection region at any given instant. As such, a maximum of one photon is emitted for each excitation pulse or cycle, completely eliminating pulse pile-up. It is therefore possible to operate at the limit set by the counting rate of the electronics. For excitation rates that exceed the capabilities of the electronics, it will be necessary, however, to employ some type of rate reduction scheme, such as described in W. R. Laws et al., 1984, Rev. Sci. Instrum. 55:1564–1568, which is incorporated herein by reference.

It is known in the art that under certain physical and chemical conditions, native nucleotides have a significant intersystem crossing rate. This means that a nucleotide which has been excited to the first singlet state by absorption of a photon of appropriate wavelength will cross to the spin-forbidden triplet state with some frequency. The lifetime of the triplet state is significantly longer than the lifetime of the singlet state. Relaxation from the triplet state can occur by both radiative (phosphorescence) and non-radiative mechanisms. If a nucleotide is in the triplet state, it is not able to undergo repeated cycles of fluorescence until it has returned to the ground state, which slows the rate of accumulation of photon counts, thereby reducing the sequencing rate.

In the current invention, it is highly desirable to reduce the frequency of intersystem crossing in order to obtain the highest possible sequencing rate. Chemical and physical conditions for fluorescence measurement in the solid matrix are therefore selected with this feature in mind. In addition, methods can be employed to reduce the time spent in the triplet state by incorporation of suitable chemical quenching agents, or by active optical quenching.

Chemical quenching of phosphorescence is well known in the art. Suitable quenching agents may be selected based on the known photophysical properties of the nucleotides. Such a quenching agent will have a first singlet energy level which is equal to the first triplet energy level of the nucleotide. It is thereby possible for the energy of the triplet state nucleotide to be transferred by a non-radiative mechanism to the first singlet state of the quencher, thereby returning the nucleotide to the ground state. The quenching agent is further chosen such that it rapidly undergoes a non-radiative deexcitation from the first singlet state to the ground state. Other desirable properties of the chemical quenching agent are that it be chemically inert with respect to reaction with the nucleotide, photostable, non-fluorescent and non-absorbing in the wavelength region for nucleotide excitation and fluorescent emission.

An alternative means for quenching the triplet state of the nucleotide is to employ an optical quenching mechanism. In optical quenching, each laser excitation pulse is followed immediately by a second pulse of similar duration and at a wavelength which corresponds to the energy level of the first triplet state. If the single nucleotide is excited by the first pulse to the first singlet state, the second pulse will not be absorbed and the fluorescent emission of the nucleotide will not be disturbed. If, however, the nucleotide has crossed to the triplet state, the second pulse which is matched in energy to the triplet state will cause stimulated emission from the triplet state, returning the nucleotide to the ground state. No fluorescent photon will be recorded during that excitation cycle, but the nucleotide will be available for excitation by the next pulse. In effect, every time the nucleotide crosses to the triplet state, it is stimulated back to the ground state by the secondary pulse.

While the various embodiments described above have been based on irradiating the nucleotide with pulses having a photon energy equivalent to the energy of the first singlet energy state, other means of excitation are contemplated. For example, it is expected that two photon excitation may be utilized as described in S. A. Williams, 1989, "Polarized One- and Two-Photon Fluorescence Excitation Spectroscopy On Selected Nucleic Acid Bases", Doctoral Thesis, Montana State University, which is incorporated herein reference. Rather than exciting the nucleotide with a single photon having an energy equal to the first singlet energy state, two photons coincident in time and each having half the singlet state energy may be used to excite the nucleotide. Desirably, this means of excitation requires photons in the wavelength range of 480–600 nm rather than the 240–300 nm range, which because of the wavelength dependence reduces the background from fluorescent impurities and Raman and Rayleigh scattering. Suitable laser sources are available by frequency doubling the output of a femtosecond or picosecond Ti:sapphire laser (Nebel and Beigang, 1991, Optics Lett. 16:1729–1731, which is incorporated herein by reference) such as the MIRA 900 Dual Femto and Picosecond Modelocked laser with Model 4500 Frequency-doubling assembly from Coherent Laser Group, Palo Alto, Calif.

In considering the accuracy of the current sequencing method, it is necessary to analyze the photon counting statistics. In the simplified case where discrimination of nucleotides is based solely on the difference in measured fluorescent half-life, the precision in lifetime measurement is approximated by $1/\sqrt{N}$ where N is the number of detected photons. Therefore 100 detected photons are required for a ~10% precision in lifetime. Similar estimates are obtained from a Monte Carlo simulation of the sampling of the emitted photons. For two nucleotides which differ in fluorescent half-life by only 0.4 nsec, (e.g., 1.1 vs. 1.5 nsec), recording of only 50 photons results in a ~2% error in identification, whereas 100 recorded photons produces no errors in 200 trials (<0.5% error).

It will be recognized by one skilled in the art that a critical requirement for base-at-a-time single-molecule DNA sequencing is the ability to detect and discriminate individual nucleotides. This is best accomplished by recording the time-resolved fluorescence emission spectra of each successive nucleotide, and comparing it with previously measured reference spectra for each of the nucleotides. The accuracy with which a nucleotide can be detected and discriminated will depend on the number of fluorescent photons which can be recorded from that nucleotide. The upper limit on the number of possible photons which can be recorded will be dependent on the time integrated fluorescent emission under the conditions of measurement (1976 Hirschfeld, Applied Optics 15:3135–3139, which is incorporated herein by reference). For purposes of the present invention it will therefore be desirable to provide measurement conditions which maximize both photostability and the quantum yield of fluorescence for each of the nucleotides which will affect the rate and efficiency of photon detection.

6. ALTERNATIVES

In the preferred embodiment of the present invention, operating parameters are provided which allow for the accurate detection and discrimination of each of the native nucleotides. It will be recognized that there are many alternative embodiments where, for various reasons (e.g., increasing the rate of sequencing or simplifying the instrumentation), these ideal conditions cannot be achieved. Nonetheless, it is possible to practice numerous variations of the present invention which still allow practical sequencing.

In general, there are three categories of nucleotides which can be employed in the practice of the present invention. Native nucleotides are the preferred form, which provide the only opportunity for direct genomic sequencing and further eliminate possible sources of error, time and expense involved in the incorporation of non-native nucleotides into synthetic templates for sequencing. The second class of nucleotides are the fluorescent nucleotide analogs as described supra (Section 2.7), while the third class involves covalent attachment of fluorescent chromophores to nucleotides by means of linkers as explored by Jett et al., (U.S. Pat. No. 4,962,037). It must be recognized that in the latter two cases, it is necessary to first synthesize a copy of the DNA to be sequenced using an appropriate polymerase which is able to incorporate the nucleotide analogs or the dye-tagged nucleotides. Furthermore, it is necessary to employ an exonuclease which can cleave such synthetic templates containing nucleotide analogs or dye-tagged nucleotides.

In addition to methods which utilize only native nucleotides, nucleotide analogs, or dye-tagged nucleotides, there are four general possibilities for using combinations of these nucleotides: native nucleotides plus nucleotide analogs, native nucleotides plus dye-tagged nucleotides, nucleotide analogs plus dye-tagged nucleotides, and native nucleotides plus nucleotide analogs plus dye-tagged nucleotides. Within each of these four categories, all possible combinations are possible (e.g., 3 native plus 1 analog, 2 native plus 2 analogs, 1 native plus 3 analogs, etc.). The ability to combine various classes of nucleotides overcomes many of the difficulties encountered by others in attempting to incorporate dye-tagged nucleotides exclusively (1992 Harding and Keller, Trends in Biotechnology 10:55–57, which is incorporated herein by reference).

Further possibilities are provided by multi-pass sequencing, wherein the sequence is derived by sequencing the same strand multiple times. In each separate pass, information is obtained about one or more nucleotides by changing the operating parameters of the instrument and/or by employing different combinations of detectable nucleotides. The final sequence is obtained by combining information from such multiple passes. This method is further enhanced and extended by including the sequence of the complementary DNA strand. The exact combinations required for multi-pass sequencing will depend on whether: (a) the nucleotide can be uniquely discriminated from the other three nucleotides, (b) the nucleotide can be discriminated as either a purine or pyrimidine, (c) the nucleotide can be detected as a nucleotide, or (d) the nucleotide cannot be detected at all. It will be obvious to those skilled in the art that there are many combinations of these conditions for detection and discrimination which will allow sequencing to be carried out by the present invention. Several general examples are provided below for illustration, but they are not meant to limit the scope of possible combinations.

For example, if only one of each of the complementary pairs of the nucleotides can be discriminated (e.g., A and C) and their complements (e.g., G and T) can be detected as nucleotides but cannot be discriminated, then sequencing of both complementary strands will provide sufficient information to reconstruct the full sequence as illustrated below. This is independent of whether the nucleotides are native, analogs, dye-tagged or any combination thereof.
5'-ACGTTCAG-3'
3'-TGCAAGTC-5'
5'-ACXXXCAX-3'
3'-XXCAAXXC-5'

In a case where only one nucleotide can be discriminated and the other three are detectable as nucleotides, at least three and preferably four separate sequences will need to be combined to reconstruct the final sequence. The ability to discriminate a different nucleotide in each separate pass can be accomplished by adjusting the operating parameters of the nucleotide-containing matrix 71 and/or the operating parameters of the detection station 90 and/or by incorporating a different discriminateable nucleotide into a separate copy of the DNA template for each separate pass.

Even in cases where one or more nucleotides cannot be detected, it will be possible to sequence if the rate of cleavage of the exonuclease employed is sufficiently uniform. With a uniform generation of single nucleotides, the arrival time of the next nucleotide in the excitation region 100 can be predicted. Nucleotides which are not detectable will therefore show up as gaps in the sequence. Such gaps can then be filled in either by sequencing the complementary strand, if the nucleotide which is complementary to the undetectable nucleotide is itself detectable and discriminateable, or if the undetectable nucleotide can be made detectable and discriminateable in a subsequent pass by any of the methods indicated supra.

It is apparent that many modifications and variations of this invention as hereinabove set forth may be made without departing from the spirit and scope thereof. The specific embodiments described are given by way of example only and the invention is limited only by the terms of the appended claims. As used in the claims, the term "DNA" or "deoxyribonucleic acid" shall be construed as collectively including DNA containing native nucleotides, DNA containing one or more modified nucleotides (e.g., dye-tagged nucleotides containing a chemically or enzymatically modified base, sugar, and/or phosphate), DNA containing one or more nucleotide analogs, and combinations of the above unless expressly stated otherwise. As used in the claims, the term "nucleotide" shall be construed as collectively including native nucleotides, nucleotide analogs, modified nucleotides (e.g., dye-tagged nucleotides containing a chemically or enzymatically modified base, sugar and/or phosphate), and combinations of the above, unless stated otherwise.

What is claimed is:

1. A genome sequencer comprising:
    means for sequentially separating single nucleotides from a strand of DNA;
    means for confining the separated nucleotides in their original sequence in a solid matrix;
    means for exciting each separated nucleotide;
    means for detecting the spectroscopic emission of each separated nucleotide; and
    means for identifying each separated nucleotide according to its spectroscopic emission.

2. The genome sequencer according to claim 1 wherein means for exciting each separated nucleotide includes a laser system.

3. The genome sequencer according to claim 2 wherein the laser system includes a mode-locked laser.

4. The genome sequencer according to claim 3 wherein the mode-locked laser operates in tunable wavelength region from approximately 240 nm to 300 nm.

5. The genome sequencer method according to claim 4 wherein the mode-locked laser operates at a repetition rate of 76 MHz.

6. The genome sequencer according to claim 5 wherein the mode-locked laser operates with a pulse width of approximately one picosecond.

7. The genome sequencer according to claim 1 wherein means for detecting the spectroscopic emission of each separated nucleotide includes means for measuring by single photon counting the fluorescence spectrum of each separated nucleotide.

8. The genome sequencer according to claim 7 wherein means for measuring by single photon counting the fluorescence spectrum of each separated nucleotide includes a monochromator.

9. The genome sequencer according to claim 7 further comprising means for time gating the single photon counting.

10. The genome sequencer according to claim 1 wherein means for detecting the spectroscopic emission of each separated nucleotide includes means for measuring by single photon counting the fluorescence lifetime of each separated nucleotide.

11. The genome sequencer according to claim 10 further comprising means for time correlating the single photon counting.

12. The genome sequencer according to claim 11 wherein means for time correlating includes a time-to-amplitude converter.

13. The genome sequencer according to claim 12 wherein means for time correlating further includes a multi-channel analyzer.

14. The genome sequencer according to claim 1 wherein means for detecting includes a micro-channel plate photomultiplier.

15. The genome sequencer according to claim 1 wherein means for detecting includes a single-photon avalanche diode.

16. The genome sequencer according to claim 1 10 wherein means for detecting includes a streak camera.

17. The genome sequencer according to claim 1 further comprising optical fibers for collecting the spectroscopic emission.

18. A genome sequencer comprising:
    (a) means for sequentially separating single nucleotides from a strand of DNA in the order of the original sequence of said nucleotides in said strand; and
    (b) a refrigeration system capable of cooling a solution containing said separated nucleotides to a temperature sufficient to vitrify the solution containing said separated nucleotides.

19. The genome sequencer according to claim 18 wherein the means for separating includes an optical trap suitable for positioning a microsphere to which said strand of DNA is affixed.

20. The genome sequencer according to claim 18 wherein the means for separating includes means for depositing said separated nucleotides on a solid support.

21. The genome sequencer according to claim 18 wherein the means for separating includes (i) an optical trap suitable for positioning a microsphere to which said strand of DNA is affixed; and (ii) means for depositing said separated nucleotides on a transparent support in a thin continuous liquid film or as discrete droplets; said sequencer further comprising a radiation source for irradiating said nucleotides so as to cause said nucleotides to fluoresce, and means for moving said support from a first position where said nucleotides are cooled by said refrigeration system to a second position where said nucleotides are irradiated by said radiation source.

22. The genome sequencer according to claim 21 further comprising means for detecting fluorescence of said nucleotides.

23. The genome sequencer according to claim 18 further comprising a radiation source for irradiating the nucleotides so as to cause said nucleotides to fluoresce.

24. The genome sequencer according to claim 23 further comprising means for detecting fluorescence of said nucleotides.

25. A genome sequencer comprising:
(a) a sheath, laminar flow microchannel;
(b) means for regulating flow through the microchannel so as to achieve hydrodynamic focusing; and
(c) a refrigeration system capable of imposing a temperature gradient over the microchannel, sufficient to vitrify an aqueous solution within said microchannel.

26. The genome sequencer of claim 1 wherein the means for separating includes an optical trap suitable for positioning a microsphere to which said strand of DNA is affixed.

27. The genome sequencer according to claim 1 wherein the means for separating includes means for fixing said separated nucleotides in a solid support.

* * * * *